(12) United States Patent
McLean

(10) Patent No.: US 12,201,523 B2
(45) Date of Patent: Jan. 21, 2025

(54) HYDRAULIC SYSTEMS FOR DELIVERING PROSTHETIC HEART VALVE DEVICES AND ASSOCIATED METHODS

(71) Applicant: Twelve, Inc., Redwood City, CA (US)

(72) Inventor: Matthew McLean, San Francisco, CA (US)

(73) Assignee: Twelve, Inc., Redwood City, CA (US)

( * ) Notice: Subject to any disclaimer, the term of this patent is extended or adjusted under 35 U.S.C. 154(b) by 0 days.

(21) Appl. No.: 18/351,728

(22) Filed: Jul. 13, 2023

(65) Prior Publication Data

US 2023/0346553 A1    Nov. 2, 2023

Related U.S. Application Data

(60) Continuation of application No. 16/752,137, filed on Jan. 24, 2020, now Pat. No. 11,737,873, which is a
(Continued)

(51) Int. Cl.
*A61F 2/24* (2006.01)
*A61F 2/966* (2013.01)
*A61F 2/95* (2013.01)

(52) U.S. Cl.
CPC ............ *A61F 2/243* (2013.01); *A61F 2/2433* (2013.01); *A61F 2/2436* (2013.01); *A61F 2/9517* (2020.05);
(Continued)

(58) Field of Classification Search
CPC ...... A61F 2/2427; A61F 2/243; A61F 2/2433; A61F 2/2436
See application file for complete search history.

(56) References Cited

U.S. PATENT DOCUMENTS 3,526,219 A    9/1970    Balamuth
3,565,062 A    2/1971    Kurtis
(Continued)

FOREIGN PATENT DOCUMENTS

CN        1440261      9/2003
CN      101076290     11/2007
(Continued)

OTHER PUBLICATIONS

US 9,265,606 B2, 02/2016, Buchbinder et al. (withdrawn)
(Continued)

*Primary Examiner* — Katherine H Schwiker
(74) *Attorney, Agent, or Firm* — Medler Ferro Woodhouse & Mills PLLC

(57) ABSTRACT

Systems for delivering prosthetic heart valve devices and associated methods are disclosed herein. A delivery system configured in accordance with embodiments of the present technology can include, for example, an elongated catheter body, a delivery capsule carried by the elongated catheter body, and two fluid chambers within the delivery capsule. The delivery capsule can be hydraulically driven between a containment configuration for holding the prosthetic heart valve device and a deployment configuration for at least partially deploying the prosthetic heart valve device. For example, the delivery capsule can be urged towards the deployment configuration when fluid is removed from the first chamber and fluid is delivered into the second chamber, whereas the delivery capsule can be urged towards the containment configuration to resheathe the prosthetic heart valve device when fluid is removed from the second chamber and delivered into the first chamber.

18 Claims, 21 Drawing Sheets

Related U.S. Application Data division of application No. 15/490,008, filed on Apr. 18, 2017, now Pat. No. 10,575,950.

(52) U.S. Cl.
CPC ............... *A61F 2002/9534* (2013.01); *A61F 2002/9665* (2013.01)

(56) References Cited

U.S. PATENT DOCUMENTS

| | | |
|---|---|---|
| 3,589,363 A | 6/1971 | Banko et al. |
| 3,667,474 A | 6/1972 | Lapkin et al. |
| 3,823,717 A | 7/1974 | Pohlman et al. |
| 3,861,391 A | 1/1975 | Antonevich et al. |
| 3,896,811 A | 7/1975 | Storz |
| 4,042,979 A | 8/1977 | Angell |
| 4,188,952 A | 2/1980 | Loschilov et al. |
| 4,282,882 A | 8/1981 | Langham |
| 4,431,006 A | 2/1984 | Trimmer et al. |
| 4,445,509 A | 5/1984 | Auth |
| 4,484,579 A | 11/1984 | Meno et al. |
| 4,490,859 A | 1/1985 | Black et al. |
| 4,587,958 A | 5/1986 | Noguchi et al. |
| 4,589,419 A | 5/1986 | Laughlin et al. |
| 4,602,911 A | 7/1986 | Ahmadi et al. |
| 4,646,736 A | 3/1987 | Auth |
| 4,649,922 A | 3/1987 | Wiktor |
| 4,692,139 A | 9/1987 | Stiles |
| 4,747,821 A | 5/1988 | Kensey et al. |
| 4,750,902 A | 6/1988 | Wuchinich et al. |
| 4,777,951 A | 10/1988 | Cribier et al. |
| 4,787,388 A | 11/1988 | Hofmann |
| 4,796,629 A | 1/1989 | Grayzel |
| 4,808,153 A | 2/1989 | Parisi |
| 4,819,751 A | 4/1989 | Shimada et al. |
| 4,841,977 A | 6/1989 | Griffith et al. |
| 4,870,953 A | 10/1989 | DonMicheal et al. |
| 4,878,495 A | 11/1989 | Grayzel |
| 4,898,575 A | 2/1990 | Fischell et al. |
| 4,909,252 A | 3/1990 | Goldberger |
| 4,919,133 A | 4/1990 | Chiang |
| 4,920,954 A | 5/1990 | Alliger et al. |
| 4,936,281 A | 6/1990 | Stasz |
| 4,960,411 A | 10/1990 | Buchbinder |
| 4,986,830 A | 1/1991 | Owens et al. |
| 4,990,134 A | 2/1991 | Auth |
| 5,058,570 A | 10/1991 | Idemoto et al. |
| 5,069,664 A | 12/1991 | Guess et al. |
| 5,076,276 A | 12/1991 | Sakurai et al. |
| 5,106,302 A | 4/1992 | Farzin-Nia et al. |
| 5,248,296 A | 9/1993 | Alliger |
| 5,267,954 A | 12/1993 | Nita |
| 5,269,291 A | 12/1993 | Carter |
| 5,295,958 A | 3/1994 | Shturman |
| 5,304,115 A | 4/1994 | Pflueger et al. |
| 5,314,407 A | 5/1994 | Auth et al. |
| 5,318,014 A | 6/1994 | Carter |
| 5,332,402 A | 7/1994 | Teitelbaum |
| 5,344,426 A | 9/1994 | Lau et al. |
| 5,352,199 A | 10/1994 | Tower |
| 5,356,418 A | 10/1994 | Shturman |
| 5,397,293 A | 3/1995 | Alliger |
| 5,411,025 A | 5/1995 | Webster, Jr. |
| 5,411,552 A | 5/1995 | Andersen et al. |
| 5,443,446 A | 8/1995 | Shturman |
| 5,449,373 A | 9/1995 | Pinchasik et al. |
| 5,489,297 A | 2/1996 | Duran |
| 5,584,879 A | 12/1996 | Reimold et al. |
| 5,609,151 A | 3/1997 | Mulier et al. |
| 5,626,603 A | 5/1997 | Venturelli et al. |
| 5,656,036 A | 8/1997 | Palmaz |
| 5,662,671 A | 9/1997 | Barbut et al. |
| 5,681,336 A | 10/1997 | Clement et al. |
| 5,695,507 A | 12/1997 | Auth et al. |
| 5,725,494 A | 3/1998 | Brisken |
| 5,782,931 A | 7/1998 | Yang et al. |
| 5,817,101 A | 10/1998 | Fiedler |
| 5,827,229 A | 10/1998 | Auth et al. |
| 5,827,321 A | 10/1998 | Roubin et al. |
| 5,840,081 A | 11/1998 | Andersen et al. |
| 5,853,422 A | 12/1998 | Huebsch et al. |
| 5,855,601 A | 1/1999 | Bessler et al. |
| 5,868,781 A | 2/1999 | Killion |
| 5,873,811 A | 2/1999 | Wang et al. |
| 5,904,679 A | 5/1999 | Clayman |
| 5,910,129 A | 6/1999 | Koblish et al. |
| 5,957,882 A | 9/1999 | Nita et al. |
| 5,972,004 A | 10/1999 | Williamson, IV et al. |
| 5,989,208 A | 11/1999 | Nita |
| 5,989,280 A | 11/1999 | Euteneuer et al. |
| 6,047,700 A | 4/2000 | Eggers et al. |
| 6,056,759 A | 5/2000 | Fiedler |
| 6,085,754 A | 7/2000 | Alferness et al. |
| 6,113,608 A | 9/2000 | Monroe et al. |
| RE36,939 E | 10/2000 | Tachibana et al. |
| 6,129,734 A | 10/2000 | Shturman et al. |
| 6,132,444 A | 10/2000 | Shturman et al. |
| 6,159,139 A | 12/2000 | Chiu |
| 6,168,579 B1 | 1/2001 | Tsugita |
| 6,217,595 B1 | 4/2001 | Shturman et al. |
| 6,254,635 B1 | 7/2001 | Schroeder et al. |
| 6,295,712 B1 | 10/2001 | Shturman et al. |
| 6,306,414 B1 | 10/2001 | Koike |
| 6,321,109 B2 | 11/2001 | Ben-Haim et al. |
| 6,402,679 B1 | 6/2002 | Mortier et al. |
| 6,423,032 B2 | 7/2002 | Parodi |
| 6,425,916 B1 | 7/2002 | Garrison et al. |
| 6,440,164 B1 | 8/2002 | DiMatteo et al. |
| 6,454,737 B1 | 9/2002 | Nita et al. |
| 6,454,757 B1 | 9/2002 | Nita et al. |
| 6,454,799 B1 | 9/2002 | Schreck |
| 6,458,153 B1 | 10/2002 | Bailey et al. |
| 6,461,382 B1 | 10/2002 | Cao |
| 6,494,890 B1 | 12/2002 | Shturman et al. |
| 6,494,891 B1 | 12/2002 | Cornish et al. |
| 6,505,080 B1 | 1/2003 | Sutton |
| 6,514,261 B1 | 2/2003 | Randall et al. |
| 6,530,952 B2 | 3/2003 | Vesely |
| 6,540,782 B1 | 4/2003 | Snyders |
| 6,562,067 B2 | 5/2003 | Mathis |
| 6,565,588 B1 | 5/2003 | Clement et al. |
| 6,569,196 B1 | 5/2003 | Vesely |
| 6,579,308 B1 | 6/2003 | Jansen et al. |
| 6,582,460 B1 | 6/2003 | Cryer |
| 6,582,462 B1 | 6/2003 | Andersen et al. |
| 6,595,912 B2 | 7/2003 | Lau et al. |
| 6,605,109 B2 | 8/2003 | Fiedler |
| 6,616,689 B1 | 9/2003 | Ainsworth et al. |
| 6,623,452 B2 | 9/2003 | Chien et al. |
| 6,638,288 B1 | 10/2003 | Shturman et al. |
| 6,648,854 B1 | 11/2003 | Patterson et al. |
| 6,689,086 B1 | 2/2004 | Nita et al. |
| 6,702,748 B1 | 3/2004 | Nita et al. |
| 6,730,121 B2 | 5/2004 | Ortiz et al. |
| 6,746,463 B1 | 6/2004 | Schwartz |
| 6,811,801 B2 | 11/2004 | Nguyen et al. |
| 6,818,001 B2 | 11/2004 | Wulfman et al. |
| 6,843,797 B2 | 1/2005 | Nash et al. |
| 6,852,118 B2 | 2/2005 | Shturman et al. |
| 6,855,123 B2 | 2/2005 | Nita |
| 6,869,439 B2 | 3/2005 | White et al. |
| 6,951,571 B1 | 10/2005 | Srivastava |
| 6,986,775 B2 | 1/2006 | Morales et al. |
| 7,018,404 B2 | 3/2006 | Holmberg et al. |
| 7,052,487 B2 | 5/2006 | Cohn et al. |
| 7,077,861 B2 | 7/2006 | Spence |
| 7,125,420 B2 | 10/2006 | Rourke et al. |
| 7,163,552 B2 | 1/2007 | Diaz |
| 7,186,264 B2 | 3/2007 | Liddicoat et al. |
| 7,261,732 B2 | 8/2007 | Justino |
| 7,296,577 B2 | 11/2007 | Lashinski et al. |
| 7,381,218 B2 | 6/2008 | Schreck |
| 7,404,824 B1 | 7/2008 | Webler et al. |
| 7,442,204 B2 | 10/2008 | Schwammenthal et al. |

(56) References Cited

U.S. PATENT DOCUMENTS

| | | |
|---|---|---|
| 7,473,275 B2 | 1/2009 | Marquez |
| 7,510,575 B2 | 3/2009 | Spenser et al. |
| 7,585,321 B2 | 9/2009 | Cribier |
| 7,588,582 B2 | 9/2009 | Starksen et al. |
| 7,621,948 B2 | 11/2009 | Herrmann et al. |
| 7,708,775 B2 | 5/2010 | Rowe et al. |
| 7,748,389 B2 | 7/2010 | Salahieh et al. |
| 7,753,922 B2 | 7/2010 | Starksen |
| 7,753,949 B2 | 7/2010 | Lamphere et al. |
| 7,803,168 B2 | 9/2010 | Gifford et al. |
| 7,857,845 B2 | 12/2010 | Stacchino et al. |
| 7,896,915 B2 | 3/2011 | Guyenot et al. |
| 7,942,928 B2 | 5/2011 | Webler et al. |
| 7,985,238 B2 | 7/2011 | Balgobin et al. |
| 8,002,826 B2 | 8/2011 | Seguin |
| 8,052,750 B2 | 11/2011 | Tuval et al. |
| 8,062,355 B2 | 11/2011 | Figulla et al. |
| 8,109,996 B2 | 2/2012 | Stacchino et al. |
| 8,114,154 B2 | 2/2012 | Righini et al. |
| 8,252,051 B2 | 8/2012 | Chau et al. |
| 8,398,704 B2 | 3/2013 | Straubinger et al. |
| 8,403,981 B2 | 3/2013 | Forster et al. |
| 8,403,983 B2 | 3/2013 | Quadri et al. |
| 8,414,643 B2 | 4/2013 | Tuval et al. |
| 8,449,599 B2 | 5/2013 | Chau et al. |
| 8,496,671 B1 | 7/2013 | Hausen |
| 8,512,252 B2 | 8/2013 | Ludomirsky et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,540,767 B2 | 9/2013 | Zhang |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 | 12/2013 | Gross et al. |
| 8,623,077 B2 | 1/2014 | Cohn |
| 8,628,566 B2 | 1/2014 | Eberhardt et al. |
| 8,632,585 B2 | 1/2014 | Seguin et al. |
| 8,632,586 B2 | 1/2014 | Seguin et al. |
| 8,634,935 B2 | 1/2014 | Gaudiani |
| 8,647,254 B2 | 2/2014 | Callas et al. |
| 8,652,203 B2 | 2/2014 | Quadri et al. |
| 8,652,204 B2 | 2/2014 | Quill et al. |
| 8,657,872 B2 | 2/2014 | Seguin |
| 8,672,998 B2 | 3/2014 | Lichtenstein et al. |
| 8,673,001 B2 | 3/2014 | Cartledge et al. |
| 8,679,176 B2 | 3/2014 | Matheny |
| 8,685,086 B2 | 4/2014 | Navia et al. |
| 8,688,234 B2 | 4/2014 | Zhu et al. |
| 8,690,858 B2 | 4/2014 | Machold et al. |
| 8,709,074 B2 | 4/2014 | Solem et al. |
| 8,712,133 B2 | 4/2014 | Guehring et al. |
| 8,715,160 B2 | 5/2014 | Raman et al. |
| 8,721,665 B2 | 5/2014 | Oz et al. |
| 8,721,718 B2 | 5/2014 | Kassab |
| 8,740,918 B2 | 6/2014 | Seguin |
| 8,747,460 B2 | 6/2014 | Tuval et al. |
| 8,758,431 B2 | 6/2014 | Orlov et al. |
| 8,758,432 B2 | 6/2014 | Solem |
| 8,771,292 B2 | 7/2014 | Allen et al. |
| 8,771,345 B2 | 7/2014 | Tuval et al. |
| 8,771,346 B2 | 7/2014 | Tuval et al. |
| 8,777,991 B2 | 7/2014 | Zarbatany et al. |
| 8,778,016 B2 | 7/2014 | Janovsky et al. |
| 8,781,580 B2 | 7/2014 | Hedberg et al. |
| 8,784,482 B2 | 7/2014 | Rahdert et al. |
| 8,792,699 B2 | 7/2014 | Guetter et al. |
| 8,795,356 B2 | 8/2014 | Quadri et al. |
| 8,801,779 B2 | 8/2014 | Seguin et al. |
| 8,808,356 B2 | 8/2014 | Braido et al. |
| 8,808,366 B2 | 8/2014 | Braido et al. |
| 8,812,431 B2 | 8/2014 | Voigt et al. |
| 8,828,043 B2 | 9/2014 | Chambers |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 8,858,622 B2 | 10/2014 | Machold et al. |
| 8,859,514 B2 | 10/2014 | Crooke et al. |
| 8,859,724 B2 | 10/2014 | Meier et al. |
| 8,864,822 B2 | 10/2014 | Spence et al. |
| 8,870,936 B2 | 10/2014 | Rowe |
| 8,870,948 B1 | 10/2014 | Erzberger et al. |
| 8,870,949 B2 | 10/2014 | Rowe |
| 8,894,702 B2 | 11/2014 | Quadri et al. |
| 8,900,214 B2 | 12/2014 | Nance et al. |
| 8,900,295 B2 | 12/2014 | Migliazza et al. |
| 8,920,411 B2 | 12/2014 | Gelbart et al. |
| 8,926,694 B2 | 1/2015 | Costello |
| 8,932,348 B2 | 1/2015 | Solem et al. |
| 8,936,027 B2 | 1/2015 | Santamore et al. |
| 8,951,285 B2 | 2/2015 | Sugimoto et al. |
| 8,961,597 B2 | 2/2015 | Subramanian et al. |
| 8,968,393 B2 | 3/2015 | Rothstein |
| 8,968,395 B2 | 3/2015 | Hauser et al. |
| 8,974,445 B2 | 3/2015 | Warnking et al. |
| 8,979,922 B2 | 3/2015 | Jayasinghe et al. |
| 8,979,923 B2 | 3/2015 | Spence et al. |
| 8,986,370 B2 | 3/2015 | Annest |
| 8,986,376 B2 | 3/2015 | Solem |
| 8,992,604 B2 | 3/2015 | Gross et al. |
| 9,011,522 B2 | 4/2015 | Annest |
| 9,011,523 B2 | 4/2015 | Seguin |
| 9,017,399 B2 | 4/2015 | Gross et al. |
| 9,023,098 B2 | 5/2015 | Kuehn |
| 9,023,100 B2 | 5/2015 | Quadri et al. |
| 9,023,101 B2 | 5/2015 | Krahbichler |
| 9,050,188 B2 | 6/2015 | Schweich, Jr. et al. |
| 9,066,800 B2 | 6/2015 | Clague et al. |
| 9,084,676 B2 | 7/2015 | Chau et al. |
| 9,095,433 B2 | 8/2015 | Lutter et al. |
| 9,119,713 B2 | 9/2015 | Board et al. |
| 9,132,009 B2 | 9/2015 | Hacohen et al. |
| 9,138,312 B2 | 9/2015 | Tuval et al. |
| 9,138,313 B2 | 9/2015 | McGuckin, Jr. et al. |
| 9,180,005 B1 | 11/2015 | Lashinski et al. |
| 9,192,466 B2 | 11/2015 | Kowalsky et al. |
| 9,192,471 B2 | 11/2015 | Bolling |
| 9,226,825 B2 | 1/2016 | Starksen et al. |
| 9,232,942 B2 | 1/2016 | Seguin et al. |
| 9,232,998 B2 | 1/2016 | Wilson et al. |
| 9,232,999 B2 | 1/2016 | Maurer et al. |
| 9,241,790 B2 | 1/2016 | Lane et al. |
| 9,248,014 B2 | 2/2016 | Lane et al. |
| 9,254,192 B2 | 2/2016 | Lutter et al. |
| 9,259,317 B2 | 2/2016 | Wilson et al. |
| 9,271,833 B2 | 3/2016 | Kim et al. |
| 9,289,291 B2 | 3/2016 | Gorman, III et al. |
| 9,289,297 B2 | 3/2016 | Wilson et al. |
| 9,289,927 B2 | 3/2016 | Weber et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,326,852 B2 | 5/2016 | Spenser |
| 9,333,073 B2 | 5/2016 | Quadri et al. |
| 9,333,074 B2 | 5/2016 | Quadri et al. |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,358,108 B2 | 6/2016 | Boertlein et al. |
| 9,387,075 B2 | 7/2016 | Boertlein et al. |
| 9,387,078 B2 | 7/2016 | Gross et al. |
| 9,393,111 B2 | 7/2016 | Ma et al. |
| 9,425,916 B2 | 8/2016 | Nakao et al. |
| 9,579,198 B2 | 2/2017 | Deem et al. |
| 9,629,719 B2 | 4/2017 | Rothstein |
| 9,675,454 B2 | 6/2017 | Vidlund et al. |

(56) References Cited

U.S. PATENT DOCUMENTS

| | | |
|---|---|---|
| 9,681,951 B2 | 6/2017 | Ratz et al. |
| 9,687,342 B2 | 6/2017 | Figulla et al. |
| 9,687,343 B2 | 6/2017 | Boertlein et al. |
| 9,693,859 B2 | 7/2017 | Braido et al. |
| 9,693,862 B2 | 7/2017 | Campbell et al. |
| 9,694,121 B2 | 7/2017 | Alexander et al. |
| 9,700,409 B2 | 7/2017 | Braido et al. |
| 9,700,411 B2 | 7/2017 | Klima et al. |
| 9,730,791 B2 | 8/2017 | Ratz et al. |
| 9,730,794 B2 | 8/2017 | Carpentier et al. |
| 9,750,605 B2 | 9/2017 | Ganesan et al. |
| 9,750,606 B2 | 9/2017 | Ganesan et al. |
| 9,750,607 B2 | 9/2017 | Ganesan et al. |
| 9,763,657 B2 | 9/2017 | Hacohen et al. |
| 9,763,658 B2 | 9/2017 | Eigler et al. |
| 9,763,782 B2 | 9/2017 | Solem |
| 9,770,328 B2 | 9/2017 | Macoviak |
| 9,788,931 B2 | 10/2017 | Giordano et al. |
| 9,801,717 B2 | 10/2017 | Edquist et al. |
| 9,827,092 B2 | 11/2017 | Vidlund et al. |
| 9,827,101 B2 | 11/2017 | Solem et al. |
| 9,833,313 B2 | 12/2017 | Board et al. |
| 9,833,315 B2 | 12/2017 | Vidlund et al. |
| 9,839,511 B2 | 12/2017 | Ma et al. |
| 9,844,435 B2 | 12/2017 | Eidenschink |
| 9,848,880 B2 | 12/2017 | Coleman et al. |
| 9,848,983 B2 | 12/2017 | Lashinski et al. |
| 9,861,477 B2 | 1/2018 | Backus et al. |
| 9,861,480 B2 | 1/2018 | Zakai et al. |
| 9,968,453 B2 | 5/2018 | Vola et al. |
| 10,258,468 B2 | 4/2019 | Deem et al. |
| 10,433,961 B2 | 10/2019 | McLean |
| 10,575,950 B2 | 3/2020 | McLean |
| 10,646,338 B2 | 5/2020 | Mauch et al. |
| 11,559,398 B2 | 1/2023 | Mauch et al. |
| 2001/0021872 A1 | 9/2001 | Bailey et al. |
| 2001/0049492 A1 | 12/2001 | Frazier et al. |
| 2002/0007219 A1 | 1/2002 | Merrill et al. |
| 2002/0013571 A1 | 1/2002 | Goldfarb et al. |
| 2002/0072792 A1 | 6/2002 | Burgermeister et al. |
| 2002/0077627 A1 | 6/2002 | Johnson et al. |
| 2002/0082637 A1 | 6/2002 | Lumauig |
| 2002/0099439 A1 | 7/2002 | Schwartz et al. |
| 2002/0138138 A1 | 9/2002 | Yang |
| 2002/0151970 A1 | 10/2002 | Garrison et al. |
| 2002/0173841 A1 | 11/2002 | Ortiz et al. |
| 2003/0120340 A1 | 6/2003 | Liska et al. |
| 2003/0139689 A1 | 7/2003 | Shturman et al. |
| 2004/0006358 A1 | 1/2004 | Wulfman et al. |
| 2004/0039412 A1 | 2/2004 | Isshiki et al. |
| 2004/0044350 A1 | 3/2004 | Martin et al. |
| 2004/0057955 A1 | 3/2004 | O'Brien et al. |
| 2004/0082910 A1 | 4/2004 | Constantz et al. |
| 2004/0092858 A1 | 5/2004 | Wilson et al. |
| 2004/0092962 A1 | 5/2004 | Thornton et al. |
| 2004/0092989 A1 | 5/2004 | Wilson et al. |
| 2004/0106989 A1 | 6/2004 | Wilson et al. |
| 2004/0117009 A1 | 6/2004 | Cali et al. |
| 2004/0122510 A1 | 6/2004 | Sarac |
| 2004/0127979 A1 | 7/2004 | Wilson et al. |
| 2004/0127982 A1 | 7/2004 | Machold et al. |
| 2004/0186558 A1 | 9/2004 | Pavcnik et al. |
| 2004/0199191 A1 | 10/2004 | Schwartz |
| 2004/0230117 A1 | 11/2004 | Tosaya et al. |
| 2004/0230212 A1 | 11/2004 | Wulfman |
| 2004/0230213 A1 | 11/2004 | Wulfman et al. |
| 2004/0243162 A1 | 12/2004 | Wulfman et al. |
| 2005/0007219 A1 | 1/2005 | Ma et al. |
| 2005/0075662 A1 | 4/2005 | Pedersen et al. |
| 2005/0075720 A1 | 4/2005 | Nguyen et al. |
| 2005/0075727 A1 | 4/2005 | Wheatley |
| 2005/0096647 A1 | 5/2005 | Steinke et al. |
| 2005/0107661 A1 | 5/2005 | Lau et al. |
| 2005/0137682 A1 | 6/2005 | Justino |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137700 A1 | 6/2005 | Spence et al. |
| 2005/0137701 A1 | 6/2005 | Salahieh et al. |
| 2005/0137702 A1 | 6/2005 | Haug et al. |
| 2005/0267523 A1 | 12/2005 | Devellian et al. |
| 2006/0058872 A1 | 3/2006 | Salahieh et al. |
| 2006/0106456 A9 | 5/2006 | Machold et al. |
| 2006/0142833 A1 | 6/2006 | Von Oepen et al. |
| 2006/0149360 A1 | 7/2006 | Schwammenthal et al. |
| 2006/0167543 A1 | 7/2006 | Bailey et al. |
| 2006/0195183 A1 | 8/2006 | Navia et al. |
| 2006/0253191 A1 | 11/2006 | Salahieh et al. |
| 2006/0287719 A1 | 12/2006 | Rowe et al. |
| 2007/0056346 A1 | 3/2007 | Spenser et al. |
| 2007/0061010 A1 | 3/2007 | Hauser et al. |
| 2007/0073391 A1 | 3/2007 | Bourang et al. |
| 2007/0088431 A1 | 4/2007 | Bourang et al. |
| 2007/0135826 A1 | 6/2007 | Zaver et al. |
| 2007/0142906 A1 | 6/2007 | Figulla et al. |
| 2007/0173932 A1 | 7/2007 | Cali et al. |
| 2007/0203561 A1 | 8/2007 | Forster et al. |
| 2007/0293934 A1 | 12/2007 | Grewe |
| 2008/0071369 A1 | 3/2008 | Tuval et al. |
| 2008/0082166 A1 | 4/2008 | Styrc et al. |
| 2008/0103586 A1 | 5/2008 | Styrc et al. |
| 2008/0140189 A1 | 6/2008 | Nguyen et al. |
| 2008/0208332 A1 | 8/2008 | Lamphere et al. |
| 2008/0221672 A1 | 9/2008 | Lamphere et al. |
| 2008/0234728 A1 | 9/2008 | Starksen et al. |
| 2008/0243245 A1 | 10/2008 | Thambar et al. |
| 2008/0243246 A1 | 10/2008 | Ryan et al. |
| 2009/0024137 A1 | 1/2009 | Chuter et al. |
| 2009/0054969 A1 | 2/2009 | Salahieh et al. |
| 2009/0076586 A1 | 3/2009 | Hauser et al. |
| 2009/0076598 A1 | 3/2009 | Salahieh et al. |
| 2009/0093670 A1 | 4/2009 | Annest et al. |
| 2009/0157174 A1 | 6/2009 | Yoganathan et al. |
| 2009/0164006 A1 | 6/2009 | Seguin et al. |
| 2009/0198315 A1 | 8/2009 | Boudjemline |
| 2009/0216312 A1 | 8/2009 | Straubinger et al. |
| 2009/0240320 A1 | 9/2009 | Tuval et al. |
| 2009/0259292 A1 | 10/2009 | Bonhoeffer |
| 2009/0259306 A1 | 10/2009 | Rowe |
| 2009/0264997 A1 | 10/2009 | Salahieh et al. |
| 2009/0276040 A1 | 11/2009 | Rowe et al. |
| 2009/0281609 A1 | 11/2009 | Benichou et al. |
| 2009/0281618 A1 | 11/2009 | Hill et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2009/0319038 A1 | 12/2009 | Gurskis et al. |
| 2010/0016958 A1 | 1/2010 | St. Goar et al. |
| 2010/0023117 A1 | 1/2010 | Yoganathan et al. |
| 2010/0030330 A1 | 2/2010 | Bobo et al. |
| 2010/0035703 A1 | 2/2010 | Ishikawa et al. |
| 2010/0049313 A1 | 2/2010 | Alon et al. |
| 2010/0076548 A1 | 3/2010 | Konno |
| 2010/0082094 A1 | 4/2010 | Quadri et al. |
| 2010/0094411 A1 | 4/2010 | Tuval et al. |
| 2010/0121436 A1 | 5/2010 | Tuval et al. |
| 2010/0160931 A1 | 6/2010 | Karpiel et al. |
| 2010/0185275 A1 | 7/2010 | Richter et al. |
| 2010/0217382 A1 | 8/2010 | Chau et al. |
| 2010/0249915 A1 | 9/2010 | Zhang |
| 2010/0249923 A1 | 9/2010 | Alkhatib et al. |
| 2010/0286768 A1 | 11/2010 | Alkhatib et al. |
| 2010/0298929 A1 | 11/2010 | Thornton et al. |
| 2010/0298931 A1 | 11/2010 | Quadri et al. |
| 2010/0312333 A1 | 12/2010 | Navia et al. |
| 2010/0324554 A1 | 12/2010 | Gifford et al. |
| 2011/0004296 A1 | 1/2011 | Lutter et al. |
| 2011/0015722 A1 | 1/2011 | Hauser et al. |
| 2011/0022166 A1 | 1/2011 | Dahlgren et al. |
| 2011/0029071 A1 | 2/2011 | Zlotnick et al. |
| 2011/0029072 A1 | 2/2011 | Gabbay |
| 2011/0040374 A1 | 2/2011 | Goetz et al. |

(56) References Cited

U.S. PATENT DOCUMENTS

| | | |
|---|---|---|
| 2011/0040375 A1 | 2/2011 | Letac et al. |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0153008 A1 | 6/2011 | Marchand et al. |
| 2011/0172784 A1 | 7/2011 | Richter et al. |
| 2011/0184512 A1 | 7/2011 | Webler et al. |
| 2011/0201874 A1 | 8/2011 | Birk et al. |
| 2011/0208293 A1 | 8/2011 | Tabor |
| 2011/0224785 A1 | 9/2011 | Hacohen |
| 2011/0251681 A1 | 10/2011 | Shipley et al. |
| 2011/0319988 A1 | 12/2011 | Schankereli et al. |
| 2012/0022639 A1 | 1/2012 | Hacohen |
| 2012/0035703 A1 | 2/2012 | Lutter et al. |
| 2012/0035713 A1 | 2/2012 | Lutter et al. |
| 2012/0053680 A1 | 3/2012 | Bolling et al. |
| 2012/0053682 A1 | 3/2012 | Kowalsky et al. |
| 2012/0078347 A1 | 3/2012 | Braido et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0179239 A1 | 7/2012 | Quadri |
| 2012/0179244 A1 | 7/2012 | Schankereli et al. |
| 2012/0203336 A1 | 8/2012 | Annest |
| 2012/0283824 A1 | 11/2012 | Lutter et al. |
| 2013/0035628 A1 | 2/2013 | Garrison et al. |
| 2013/0138090 A1 | 5/2013 | Fargahi |
| 2013/0172978 A1 | 7/2013 | Vidlund et al. |
| 2013/0190860 A1 | 7/2013 | Sundt, III |
| 2013/0190861 A1 | 7/2013 | Chau et al. |
| 2013/0197354 A1 | 8/2013 | Maschke et al. |
| 2013/0197630 A1 | 8/2013 | Azarnoush |
| 2013/0204356 A1 | 8/2013 | Dwork et al. |
| 2013/0204358 A1 | 8/2013 | Matheny |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0238089 A1 | 9/2013 | Lichtenstein et al. |
| 2013/0244927 A1 | 9/2013 | Lal et al. |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0259337 A1 | 10/2013 | Guehring et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261741 A1 | 10/2013 | Accola |
| 2013/0268066 A1 | 10/2013 | Rowe |
| 2013/0274870 A1 | 10/2013 | Lombardi et al. |
| 2013/0282059 A1 | 10/2013 | Ketai et al. |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |
| 2013/0289717 A1 | 10/2013 | Solem |
| 2013/0289718 A1 | 10/2013 | Tsukashima et al. |
| 2013/0296851 A1 | 11/2013 | Boronyak et al. |
| 2013/0296999 A1 | 11/2013 | Burriesci et al. |
| 2013/0304180 A1 | 11/2013 | Green et al. |
| 2013/0304181 A1 | 11/2013 | Green et al. |
| 2013/0304197 A1 | 11/2013 | Buchbnder et al. |
| 2013/0304198 A1 | 11/2013 | Solem |
| 2013/0304200 A1 | 11/2013 | McLean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1 | 11/2013 | Morriss et al. |
| 2013/0317603 A1 | 11/2013 | McLean et al. |
| 2013/0325110 A1 | 12/2013 | Khalil et al. |
| 2013/0325114 A1 | 12/2013 | McLean et al. |
| 2013/0331864 A1 | 12/2013 | Jelich et al. |
| 2013/0338684 A1 | 12/2013 | Hausen |
| 2013/0338763 A1 | 12/2013 | Rowe et al. |
| 2013/0345715 A1 | 12/2013 | Gifford et al. |
| 2013/0345797 A1 | 12/2013 | Dahlgren et al. |
| 2013/0345803 A1 | 12/2013 | Bergheim, III |
| 2014/0005778 A1 | 1/2014 | Buchbnder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1 | 1/2014 | Murphy et al. |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0094906 A1 | 4/2014 | Spence et al. |
| 2014/0107775 A1 | 4/2014 | Hjelle et al. |
| 2014/0114404 A1 | 4/2014 | Gammie et al. |
| 2014/0114407 A1 | 4/2014 | Rajamannan |
| 2014/0121763 A1 | 5/2014 | Duffy et al. |
| 2014/0128965 A1 | 5/2014 | Rafiee |
| 2014/0135913 A1 | 5/2014 | Lichtenstein et al. |
| 2014/0163652 A1 | 6/2014 | Witzel et al. |
| 2014/0163668 A1 | 6/2014 | Rafiee |
| 2014/0172076 A1 | 6/2014 | Joensson et al. |
| 2014/0172084 A1 | 6/2014 | Callas et al. |
| 2014/0172085 A1 | 6/2014 | Quadri et al. |
| 2014/0172086 A1 | 6/2014 | Quadri et al. |
| 2014/0179993 A1 | 6/2014 | Alexander et al. |
| 2014/0180401 A1 | 6/2014 | Quill et al. |
| 2014/0188108 A1 | 7/2014 | Goodine et al. |
| 2014/0188215 A1 | 7/2014 | Hlavka et al. |
| 2014/0194920 A1 | 7/2014 | Krahbichler |
| 2014/0194969 A1 | 7/2014 | Headley |
| 2014/0194976 A1 | 7/2014 | Starksen et al. |
| 2014/0200397 A1 | 7/2014 | Raman et al. |
| 2014/0200649 A1 | 7/2014 | Essinger et al. |
| 2014/0200657 A1 | 7/2014 | Maurer et al. |
| 2014/0200662 A1 | 7/2014 | Eftel et al. |
| 2014/0214159 A1 | 7/2014 | Vidlund et al. |
| 2014/0219524 A1 | 8/2014 | Takeguchi et al. |
| 2014/0222040 A1 | 8/2014 | Park et al. |
| 2014/0222135 A1 | 8/2014 | Forster et al. |
| 2014/0222138 A1 | 8/2014 | Machold et al. |
| 2014/0225942 A1 | 8/2014 | Liu |
| 2014/0225946 A1 | 8/2014 | Quinn et al. |
| 2014/0228942 A1 | 8/2014 | Krahbichler et al. |
| 2014/0228946 A1 | 8/2014 | Chau et al. |
| 2014/0242056 A1 | 8/2014 | Karandikar et al. |
| 2014/0242086 A1 | 8/2014 | Lal et al. |
| 2014/0243560 A1 | 8/2014 | Lorenz et al. |
| 2014/0243860 A1 | 8/2014 | Morris et al. |
| 2014/0243954 A1 | 8/2014 | Shannon |
| 2014/0243964 A1 | 8/2014 | Venkatasubramanian |
| 2014/0249621 A1 | 9/2014 | Eidenschink |
| 2014/0257101 A1 | 9/2014 | Gaudiani |
| 2014/0257466 A1 | 9/2014 | Board et al. |
| 2014/0257467 A1 | 9/2014 | Lane et al. |
| 2014/0257473 A1 | 9/2014 | Rajamannan |
| 2014/0257475 A1 | 9/2014 | Gross et al. |
| 2014/0275757 A1 | 9/2014 | Goodwin et al. |
| 2014/0276395 A1 | 9/2014 | Wilson et al. |
| 2014/0276609 A1 | 9/2014 | Magee et al. |
| 2014/0276782 A1 | 9/2014 | Paskar |
| 2014/0276971 A1 | 9/2014 | Kovach |
| 2014/0277119 A1 | 9/2014 | Akpinar |
| 2014/0277390 A1 | 9/2014 | Ratz et al. |
| 2014/0277404 A1 | 9/2014 | Wilson et al. |
| 2014/0277405 A1 | 9/2014 | Wilson et al. |
| 2014/0277406 A1 | 9/2014 | Arcidi |
| 2014/0277407 A1 | 9/2014 | Dale et al. |
| 2014/0277408 A1 | 9/2014 | Folan |

(56) References Cited

U.S. PATENT DOCUMENTS

| | | |
|---|---|---|
| 2014/0277409 A1 | 9/2014 | Börtlein et al. |
| 2014/0277410 A1 | 9/2014 | Börtlein et al. |
| 2014/0277411 A1 | 9/2014 | Börtlein et al. |
| 2014/0277412 A1 | 9/2014 | Börtlein et al. |
| 2014/0277420 A1 | 9/2014 | Migliazza et al. |
| 2014/0277422 A1 | 9/2014 | Ratz et al. |
| 2014/0288480 A1 | 9/2014 | Zimmerman et al. |
| 2014/0296878 A1 | 10/2014 | Oz et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296975 A1 | 10/2014 | Tegels et al. |
| 2014/0303719 A1 | 10/2014 | Cox et al. |
| 2014/0303721 A1 | 10/2014 | Fung et al. |
| 2014/0309727 A1 | 10/2014 | Lamelas et al. |
| 2014/0309730 A1 | 10/2014 | Alon et al. |
| 2014/0309731 A1 | 10/2014 | Quadri et al. |
| 2014/0309732 A1 | 10/2014 | Solem |
| 2014/0316516 A1 | 10/2014 | Vidlund et al. |
| 2014/0323448 A1 | 10/2014 | Kim et al. |
| 2014/0324164 A1 | 10/2014 | Gross et al. |
| 2014/0330111 A1 | 11/2014 | Lichtenstein et al. |
| 2014/0358222 A1 | 12/2014 | Gorman, III et al. |
| 2014/0358224 A1 | 12/2014 | Tegels et al. |
| 2014/0364944 A1 | 12/2014 | Lutter et al. |
| 2014/0371843 A1 | 12/2014 | Wilson et al. |
| 2014/0371844 A1 | 12/2014 | Dale et al. |
| 2014/0371846 A1 | 12/2014 | Wilson et al. |
| 2014/0378464 A1 | 12/2014 | Oslob et al. |
| 2014/0378491 A1 | 12/2014 | Oslob et al. |
| 2014/0379074 A1 | 12/2014 | Spence et al. |
| 2014/0379076 A1 | 12/2014 | Vidlund et al. |
| 2015/0004165 A1 | 1/2015 | Yue et al. |
| 2015/0005874 A1 | 1/2015 | Vidlund et al. |
| 2015/0005875 A1 | 1/2015 | Tuval et al. |
| 2015/0012069 A1 | 1/2015 | Puskas |
| 2015/0018353 A1 | 1/2015 | Kim et al. |
| 2015/0018940 A1 | 1/2015 | Quill et al. |
| 2015/0025311 A1 | 1/2015 | Kadan et al. |
| 2015/0025623 A1 | 1/2015 | Granada et al. |
| 2015/0032127 A1 | 1/2015 | Gammie et al. |
| 2015/0032204 A1 | 1/2015 | Johansson |
| 2015/0045878 A1 | 2/2015 | Rowe |
| 2015/0057738 A1 | 2/2015 | Hepke et al. |
| 2015/0066138 A1 | 3/2015 | Alexander et al. |
| 2015/0066140 A1 | 3/2015 | Quadri et al. |
| 2015/0094802 A1 | 4/2015 | Buchbinder et al. |
| 2015/0094803 A1 | 4/2015 | Navia |
| 2015/0100116 A1 | 4/2015 | Mohl et al. |
| 2015/0112427 A1 | 4/2015 | Schweich, Jr. et al. |
| 2015/0112429 A1 | 4/2015 | Khairkhahan et al. |
| 2015/0112433 A1 | 4/2015 | Schweich, Jr. et al. |
| 2015/0119978 A1 | 4/2015 | Tegels et al. |
| 2015/0119981 A1 | 4/2015 | Khairkhahan et al. |
| 2015/0119982 A1 | 4/2015 | Quill et al. |
| 2015/0127091 A1 | 5/2015 | Cecere et al. |
| 2015/0127096 A1 | 5/2015 | Rowe et al. |
| 2015/0134055 A1 | 5/2015 | Spence et al. |
| 2015/0139911 A1 | 5/2015 | Santamore et al. |
| 2015/0141855 A1 | 5/2015 | Inoue |
| 2015/0142101 A1 | 5/2015 | Coleman et al. |
| 2015/0142103 A1 | 5/2015 | Vidlund |
| 2015/0142105 A1 | 5/2015 | Bolling et al. |
| 2015/0150678 A1 | 6/2015 | Brecker |
| 2015/0157458 A1 | 6/2015 | Thambar et al. |
| 2015/0157459 A1 | 6/2015 | Macoviak et al. |
| 2015/0164637 A1 | 6/2015 | Khairkhahan et al. |
| 2015/0164639 A1 | 6/2015 | Starksen et al. |
| 2015/0164641 A1 | 6/2015 | Annest |
| 2015/0173897 A1 | 6/2015 | Raanani et al. |
| 2015/0173898 A1 | 6/2015 | Drasler et al. |
| 2015/0173900 A1 | 6/2015 | Hauser et al. |
| 2015/0190229 A1 | 7/2015 | Seguin |
| 2015/0196390 A1 | 7/2015 | Ma et al. |
| 2015/0196393 A1 | 7/2015 | Vidlund et al. |
| 2015/0202043 A1 | 7/2015 | Zakai et al. |
| 2015/0209137 A1 | 7/2015 | Quadri et al. |
| 2015/0209139 A1 | 7/2015 | Granada et al. |
| 2015/0216655 A1 | 8/2015 | Lane et al. |
| 2015/0216661 A1 | 8/2015 | Hacohen et al. |
| 2015/0223802 A1 | 8/2015 | Tegzes |
| 2015/0223934 A1 | 8/2015 | Vidlund et al. |
| 2015/0223935 A1 | 8/2015 | Subramanian et al. |
| 2015/0230920 A1 | 8/2015 | Alfieri et al. |
| 2015/0230921 A1 | 8/2015 | Chau et al. |
| 2015/0238312 A1 | 8/2015 | Lashinski |
| 2015/0238313 A1 | 8/2015 | Spence et al. |
| 2015/0238314 A1 | 8/2015 | Börtlein et al. |
| 2015/0238729 A1 | 8/2015 | Jenson et al. |
| 2015/0250590 A1 | 9/2015 | Gries et al. |
| 2015/0257877 A1 | 9/2015 | Hernandez |
| 2015/0257878 A1 | 9/2015 | Lane et al. |
| 2015/0257879 A1 | 9/2015 | Börtlein et al. |
| 2015/0257881 A1 | 9/2015 | Börtlein et al. |
| 2015/0257882 A1 | 9/2015 | Börtlein et al. |
| 2015/0272734 A1 | 10/2015 | Sheps et al. |
| 2015/0272737 A1 | 10/2015 | Dale et al. |
| 2015/0305861 A1 | 10/2015 | Annest |
| 2015/0305864 A1 | 10/2015 | Quadri et al. |
| 2015/0313739 A1 | 11/2015 | Hummen et al. |
| 2015/0320553 A1 | 11/2015 | Chau et al. |
| 2015/0327999 A1 | 11/2015 | Board et al. |
| 2015/0328000 A1 | 11/2015 | Ratz et al. |
| 2015/0342733 A1 | 12/2015 | Alkhatib et al. |
| 2015/0351906 A1 | 12/2015 | Hammer et al. |
| 2015/0351908 A1 | 12/2015 | Keraenen et al. |
| 2015/0359628 A1 | 12/2015 | Keraenen |
| 2015/0359629 A1 | 12/2015 | Ganesan et al. |
| 2015/0359631 A1 | 12/2015 | Sheahan et al. |
| 2015/0366666 A1 | 12/2015 | Khairkhahan et al. |
| 2015/0374495 A1 | 12/2015 | Ruyra Baliarda et al. |
| 2016/0000562 A1 | 1/2016 | Siegel |
| 2016/0000564 A1 | 1/2016 | Buchbinder |
| 2016/0000983 A1 | 1/2016 | Mohl et al. |
| 2016/0008129 A1 | 1/2016 | Siegel |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0030171 A1 | 2/2016 | Quijano et al. |
| 2016/0038246 A1 | 2/2016 | Wang et al. |
| 2016/0038280 A1 | 2/2016 | Morriss et al. |
| 2016/0038283 A1 | 2/2016 | Divekar et al. |
| 2016/0038286 A1 | 2/2016 | Yellin et al. |
| 2016/0074160 A1 | 3/2016 | Christianson et al. |
| 2016/0106539 A1 | 4/2016 | Buchbinder et al. |
| 2016/0113764 A1 | 4/2016 | Sheahan et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120643 A1 | 5/2016 | Kupumbati |
| 2016/0143730 A1 | 5/2016 | Kheradvar |
| 2016/0151154 A1 | 6/2016 | Gorman, III et al. |
| 2016/0151156 A1 | 6/2016 | Seguin et al. |
| 2016/0151552 A1 | 6/2016 | Solem |
| 2016/0157999 A1 | 6/2016 | Lane et al. |
| 2016/0158000 A1 | 6/2016 | Granada et al. |
| 2016/0158001 A1 | 6/2016 | Wallace et al. |
| 2016/0158002 A1 | 6/2016 | Wallace et al. |
| 2016/0158003 A1 | 6/2016 | Wallace et al. |
| 2016/0184095 A1 | 6/2016 | Spence et al. |
| 2016/0206280 A1 | 7/2016 | Vidlund et al. |
| 2016/0206424 A1 | 7/2016 | Al-Jilaihawi et al. |
| 2016/0262881 A1 | 9/2016 | Schankereli et al. |
| 2016/0317290 A1 | 11/2016 | Chau et al. |
| 2017/0079790 A1 | 3/2017 | Vidlund et al. |
| 2017/0100248 A1 | 4/2017 | Tegels et al. |
| 2017/0100250 A1 | 4/2017 | Marsot et al. |
| 2017/0119526 A1 | 5/2017 | Luong et al. |
| 2017/0128198 A1 | 5/2017 | Cartledge et al. |
| 2017/0128205 A1 | 5/2017 | Tamir et al. |
| 2017/0128206 A1 | 5/2017 | Rafiee |
| 2017/0128208 A1 | 5/2017 | Christianson et al. |
| 2017/0156860 A1 | 6/2017 | Lashinski |
| 2017/0165054 A1 | 6/2017 | Benson et al. |

(56) References Cited

U.S. PATENT DOCUMENTS

| | | |
|---|---|---|
| 2017/0165055 A1 | 6/2017 | Hauser et al. |
| 2017/0165064 A1 | 6/2017 | Nyuli et al. |
| 2017/0172737 A1 | 6/2017 | Kuetting |
| 2017/0181851 A1 | 6/2017 | Annest |
| 2017/0189177 A1 | 7/2017 | Schweich, Jr. et al. |
| 2017/0189179 A1 | 7/2017 | Ratz et al. |
| 2017/0189180 A1 | 7/2017 | Alkhatib |
| 2017/0189181 A1 | 7/2017 | Alkhatib et al. |
| 2017/0196688 A1 | 7/2017 | Christianson et al. |
| 2017/0224977 A1* | 8/2017 | Shin .................. A61M 3/0262 |
| 2017/0231762 A1 | 8/2017 | Quadri et al. |
| 2017/0231763 A1 | 8/2017 | Yellin |
| 2017/0258585 A1 | 9/2017 | Marquez et al. |
| 2017/0266001 A1 | 9/2017 | Vidlund et al. |
| 2017/0281345 A1 | 10/2017 | Yang et al. |
| 2017/0290659 A1 | 10/2017 | Ulmer et al. |
| 2017/0296338 A1 | 10/2017 | Campbell et al. |
| 2017/0296339 A1 | 10/2017 | Thambar et al. |
| 2017/0319333 A1 | 11/2017 | Tegels et al. |
| 2017/0325842 A1 | 11/2017 | Siegel |
| 2017/0325941 A1 | 11/2017 | Wallace et al. |
| 2017/0325945 A1 | 11/2017 | Dale et al. |
| 2017/0325948 A1 | 11/2017 | Wallace et al. |
| 2017/0325949 A1 | 11/2017 | Rodgers et al. |
| 2017/0325953 A1 | 11/2017 | Klima et al. |
| 2017/0325954 A1 | 11/2017 | Perszyk |
| 2017/0333186 A1 | 11/2017 | Spargias |
| 2017/0333188 A1 | 11/2017 | Carpentier et al. |
| 2017/0340440 A1 | 11/2017 | Ratz et al. |
| 2017/0348097 A1 | 12/2017 | Taft et al. |
| 2017/0348098 A1 | 12/2017 | Rowe et al. |
| 2017/0348100 A1 | 12/2017 | Lane et al. |
| 2017/0354496 A1 | 12/2017 | Quadri et al. |
| 2017/0354497 A1 | 12/2017 | Quadri et al. |
| 2017/0354499 A1 | 12/2017 | Granada et al. |
| 2017/0360426 A1 | 12/2017 | Hacohen et al. |
| 2017/0360549 A1 | 12/2017 | Lashinski et al. |
| 2017/0360558 A1 | 12/2017 | Ma |
| 2017/0360585 A1 | 12/2017 | White |
| 2017/0361065 A1 | 12/2017 | Legaspi et al. |
| 2018/0071492 A1 | 3/2018 | Laby et al. |
| 2018/0296325 A1 | 10/2018 | McLean et al. |
| 2018/0344454 A1 | 12/2018 | Mauch et al. |
| 2019/0192286 A1 | 6/2019 | Deem et al. |

FOREIGN PATENT DOCUMENTS

| | | |
|---|---|---|
| CN | 101291637 | 10/2008 |
| CN | 102196784 A | 9/2011 |
| CN | 103491900 A | 1/2014 |
| DE | 19605042 | 1/1998 |
| DE | 102006052564 | 12/2007 |
| EP | 0875216 B1 | 7/2003 |
| EP | 1512383 | 3/2005 |
| EP | 1545371 | 6/2005 |
| EP | 1551274 | 7/2005 |
| EP | 1629794 | 3/2006 |
| EP | 1646332 | 4/2006 |
| EP | 1702247 | 9/2006 |
| EP | 1734903 | 12/2006 |
| EP | 186104 | 2/2008 |
| EP | 1891914 | 2/2008 |
| EP | 2010103 | 1/2009 |
| EP | 2026280 | 2/2009 |
| EP | 2037829 | 3/2009 |
| EP | 2081519 | 7/2009 |
| EP | 2111190 | 10/2009 |
| EP | 2142143 | 1/2010 |
| EP | 2167742 | 3/2010 |
| EP | 2203124 | 7/2010 |
| EP | 2278944 | 2/2011 |
| EP | 2306821 | 4/2011 |
| EP | 2327429 | 6/2011 |
| EP | 2400924 | 1/2012 |
| EP | 2400926 | 1/2012 |
| EP | 2410947 | 2/2012 |
| EP | 2416739 | 2/2012 |
| EP | 2419050 | 2/2012 |
| EP | 2444031 | 4/2012 |
| EP | 2470119 | 7/2012 |
| EP | 2488126 | 8/2012 |
| EP | 2509263 | 10/2012 |
| EP | 2509538 | 10/2012 |
| EP | 2510620 | 10/2012 |
| EP | 2522307 | 11/2012 |
| EP | 2549955 | 1/2013 |
| EP | 2549956 | 1/2013 |
| EP | 2566416 | 3/2013 |
| EP | 2586492 | 5/2013 |
| EP | 2611389 | 7/2013 |
| EP | 2618784 | 7/2013 |
| EP | 2623068 | 8/2013 |
| EP | 2626012 | 8/2013 |
| EP | 2626013 | 8/2013 |
| EP | 2629699 | 8/2013 |
| EP | 2633457 | 9/2013 |
| EP | 2637659 | 9/2013 |
| EP | 2641569 | 9/2013 |
| EP | 2644158 | 10/2013 |
| EP | 2654624 | 10/2013 |
| EP | 2656794 | 10/2013 |
| EP | 2656795 | 10/2013 |
| EP | 2656796 | 10/2013 |
| EP | 2667823 | 12/2013 |
| EP | 2670358 | 12/2013 |
| EP | 2676640 | 12/2013 |
| EP | 2688041 | 1/2014 |
| EP | 2693984 | 2/2014 |
| EP | 2697721 | 2/2014 |
| EP | 2713953 | 4/2014 |
| EP | 2714068 | 4/2014 |
| EP | 2717803 | 4/2014 |
| EP | 2723272 | 4/2014 |
| EP | 2723273 | 4/2014 |
| EP | 2723277 | 4/2014 |
| EP | 2739214 | 6/2014 |
| EP | 2741711 | 6/2014 |
| EP | 2750630 | 7/2014 |
| EP | 2750631 | 7/2014 |
| EP | 2755562 | 7/2014 |
| EP | 2755602 | 7/2014 |
| EP | 2757962 | 7/2014 |
| EP | 2760375 | 8/2014 |
| EP | 2777616 | 9/2014 |
| EP | 2777617 | 9/2014 |
| EP | 2782523 | 10/2014 |
| EP | 2785282 | 10/2014 |
| EP | 2786817 | 10/2014 |
| EP | 2790609 | 10/2014 |
| EP | 2793751 | 10/2014 |
| EP | 2797915 | 11/2014 |
| EP | 2800063 | 11/2014 |
| EP | 2809263 | 12/2014 |
| EP | 2810620 | 12/2014 |
| EP | 2811939 | 12/2014 |
| EP | 2814428 | 12/2014 |
| EP | 2814429 | 12/2014 |
| EP | 2819617 | 1/2015 |
| EP | 2819618 | 1/2015 |
| EP | 2819619 | 1/2015 |
| EP | 2822473 | 1/2015 |
| EP | 2833836 | 2/2015 |
| EP | 2838475 | 2/2015 |
| EP | 2839815 | 2/2015 |
| EP | 2844190 | 3/2015 |
| EP | 2849680 | 3/2015 |
| EP | 2849681 | 3/2015 |
| EP | 2852354 | 4/2015 |
| EP | 2854719 | 4/2015 |
| EP | 2870933 | 5/2015 |
| EP | 2873011 | 5/2015 |
| EP | 2875797 | 5/2015 |
| EP | 2882374 | 6/2015 |
| EP | 2886082 | 6/2015 |

(56) References Cited

FOREIGN PATENT DOCUMENTS

| | | |
|---|---|---|
| EP | 2886083 | 6/2015 |
| EP | 2886084 | 6/2015 |
| EP | 2895111 | 7/2015 |
| EP | 2901966 | 8/2015 |
| EP | 2907479 | 8/2015 |
| EP | 2911594 | 9/2015 |
| EP | 2945572 | 11/2015 |
| EP | 2948094 | 12/2015 |
| EP | 2948102 | 12/2015 |
| EP | 2964152 | 1/2016 |
| EP | 2967847 | 1/2016 |
| EP | 2967859 | 1/2016 |
| EP | 2967860 | 1/2016 |
| EP | 2967866 | 1/2016 |
| EP | 2968847 | 1/2016 |
| EP | 2976043 | 1/2016 |
| EP | 2981208 | 2/2016 |
| EP | 2982336 | 2/2016 |
| EP | 2999433 | 3/2016 |
| EP | 2999436 | 3/2016 |
| EP | 3003187 | 4/2016 |
| EP | 3003219 | 4/2016 |
| EP | 3003220 | 4/2016 |
| EP | 3010447 | 4/2016 |
| EP | 3013281 | 5/2016 |
| EP | 3017792 | 5/2016 |
| EP | 3021792 | 5/2016 |
| EP | 3023117 | 5/2016 |
| EP | 3027143 | 6/2016 |
| EP | 3027144 | 6/2016 |
| EP | 3033048 | 6/2016 |
| EP | 3037064 | 6/2016 |
| EP | 3079633 | 10/2016 |
| EP | 3082656 | 10/2016 |
| EP | 3110368 | 1/2017 |
| EP | 3110369 | 1/2017 |
| EP | 3132773 | 2/2017 |
| EP | 3184081 | 6/2017 |
| EP | 3191027 | 7/2017 |
| EP | 3206628 | 8/2017 |
| EP | 3223751 | 10/2017 |
| EP | 3229736 | 10/2017 |
| EP | 3245980 | 11/2017 |
| EP | 3250154 | 12/2017 |
| EP | 3256074 | 12/2017 |
| EP | 3256077 | 12/2017 |
| EP | 3258883 | 12/2017 |
| EP | 3270825 | 1/2018 |
| EP | 3273910 | 1/2018 |
| JP | 2002509756 | 4/2002 |
| JP | 2005280917 | 10/2005 |
| JP | H10258124 | 5/2006 |
| JP | 2008528117 | 7/2008 |
| JP | 2008541863 | 11/2008 |
| JP | 2009195712 | 9/2009 |
| JP | 2010518947 | 6/2010 |
| JP | 2012500665 A | 1/2012 |
| JP | 2012523894 A | 10/2012 |
| JP | 5219518 | 6/2013 |
| JP | 6504516 | 5/2016 |
| WO | WO 1992017118 | 10/1992 |
| WO | WO 1995011055 | 4/1995 |
| WO | WO 1995016407 | 6/1995 |
| WO | WO 1999004730 | 2/1999 |
| WO | WO 1999039648 | 8/1999 |
| WO | WO 1999049799 | 10/1999 |
| WO | WO 2001010343 | 2/2001 |
| WO | WO 2002003892 | 1/2002 |
| WO | WO 2002028421 | 4/2002 |
| WO | WO 2002039908 | 5/2002 |
| WO | WO 2003043685 | 5/2003 |
| WO | WO 2004084746 | 10/2004 |
| WO | WO 2004093728 | 11/2004 |
| WO | WO 2004096097 | 11/2004 |
| WO | WO 2004112657 | 12/2004 |
| WO | WO 2005002466 | 1/2005 |
| WO | WO 2005007219 | 1/2005 |
| WO | WO 2005009285 | 2/2005 |
| WO | WO 2005009506 | 2/2005 |
| WO | WO 2005087140 | 9/2005 |
| WO | WO 2006041877 | 4/2006 |
| WO | WO 2006063199 | 6/2006 |
| WO | WO 2007008371 | 1/2007 |
| WO | WO 2007067820 | 6/2007 |
| WO | WO 2007098232 | 8/2007 |
| WO | WO 2008022077 | 2/2008 |
| WO | WO 2008028569 | 3/2008 |
| WO | WO 2008035337 | 3/2008 |
| WO | WO 2008046593 | 4/2008 |
| WO | WO 2008103497 | 8/2008 |
| WO | WO 2008103722 | 8/2008 |
| WO | WO 2008129405 | 10/2008 |
| WO | WO 2009045338 | 4/2009 |
| WO | WO 2009091509 | 7/2009 |
| WO | WO 2010006627 | 1/2010 |
| WO | WO 2010008549 | 1/2010 |
| WO | WO 2010014420 | 2/2010 |
| WO | WO 2010022138 | 2/2010 |
| WO | WO 2010057262 | 5/2010 |
| WO | WO 2010080594 | 7/2010 |
| WO | WO 2010098857 | 9/2010 |
| WO | WO 2010099032 | 9/2010 |
| WO | WO 2010117680 | 10/2010 |
| WO | WO 2010121076 | 10/2010 |
| WO | WO 2011025981 | 3/2011 |
| WO | WO 2011047168 | 4/2011 |
| WO | WO 2011051043 | 5/2011 |
| WO | WO 2011057087 | 5/2011 |
| WO | WO 2011072084 | 6/2011 |
| WO | WO 2011106137 | 9/2011 |
| WO | WO 2011106544 | 9/2011 |
| WO | WO 2011111047 | 9/2011 |
| WO | WO 2011137531 | 11/2011 |
| WO | WO 2011139747 | 11/2011 |
| WO | WO 2012011018 | 1/2012 |
| WO | WO 2012011108 | 1/2012 |
| WO | WO 2012027487 | 3/2012 |
| WO | WO 2012035279 | 3/2012 |
| WO | WO 2012040655 | 3/2012 |
| WO | WO 2012047644 | 4/2012 |
| WO | WO 2012052718 | 4/2012 |
| WO | WO 2012055498 | 5/2012 |
| WO | WO 2012087842 | 6/2012 |
| WO | WO 2012095455 | 7/2012 |
| WO | WO 2012102928 | 8/2012 |
| WO | WO 2012106602 | 8/2012 |
| WO | WO 2012118508 | 9/2012 |
| WO | WO 2012118816 | 9/2012 |
| WO | WO 2012118894 | 9/2012 |
| WO | WO 2012152761 | 11/2012 |
| WO | WO 2012177942 | 12/2012 |
| WO | WO 2013021374 | 2/2013 |
| WO | WO 2013021375 | 2/2013 |
| WO | WO 2013028387 | 2/2013 |
| WO | WO 2013059743 | 4/2013 |
| WO | WO 2013059747 | 4/2013 |
| WO | WO 2013101830 | 7/2013 |
| WO | WO 2013114214 | 8/2013 |
| WO | WO 2013120082 | 8/2013 |
| WO | WO 2013120181 | 8/2013 |
| WO | WO 2013123059 | 8/2013 |
| WO | WO 2013128432 | 9/2013 |
| WO | WO 2013130641 | 9/2013 |
| WO | WO 2013131925 | 9/2013 |
| WO | WO 2013140318 | 9/2013 |
| WO | WO 2013148017 | 10/2013 |
| WO | WO 2013148018 | 10/2013 |
| WO | WO 2013148019 | 10/2013 |
| WO | WO 2013150512 | 10/2013 |
| WO | WO 2013152161 | 10/2013 |
| WO | WO 2013158613 | 10/2013 |
| WO | WO 2013169448 | 11/2013 |
| WO | WO 2013175468 | 11/2013 |
| WO | WO 2013176583 | 11/2013 |

(56) References Cited

FOREIGN PATENT DOCUMENTS

| | | |
|---|---|---|
| WO | WO 2013188077 | 12/2013 |
| WO | WO 2013192107 | 12/2013 |
| WO | WO 2014010169 | 1/2014 |
| WO | WO 2014036113 | 3/2014 |
| WO | WO 2014043527 | 3/2014 |
| WO | WO 2014047111 | 3/2014 |
| WO | WO 2014047325 | 3/2014 |
| WO | WO 2014055981 | 4/2014 |
| WO | WO 2014059432 | 4/2014 |
| WO | WO 2014064694 | 5/2014 |
| WO | WO 2014066365 | 5/2014 |
| WO | WO 2014089424 | 6/2014 |
| WO | WO 2014093861 | 6/2014 |
| WO | WO 2014110169 | 7/2014 |
| WO | WO 2014111918 | 7/2014 |
| WO | WO 2014114794 | 7/2014 |
| WO | WO 2014114795 | 7/2014 |
| WO | WO 2014114796 | 7/2014 |
| WO | WO 2014114798 | 7/2014 |
| WO | WO 2014116502 | 7/2014 |
| WO | WO 2014121280 | 8/2014 |
| WO | WO 2014128705 | 8/2014 |
| WO | WO 2014134277 | 9/2014 |
| WO | WO 2014138194 | 9/2014 |
| WO | WO 2014138284 | 9/2014 |
| WO | WO 2014138482 | 9/2014 |
| WO | WO 2014138868 | 9/2014 |
| WO | WO 2014143197 | 9/2014 |
| WO | WO 2014144100 | 9/2014 |
| WO | WO 2014144937 | 9/2014 |
| WO | WO 2014145338 | 9/2014 |
| WO | WO 2014147336 | 9/2014 |
| WO | WO 2014152306 | 9/2014 |
| WO | WO 2014152375 | 9/2014 |
| WO | WO 2014152503 | 9/2014 |
| WO | WO 2014153544 | 9/2014 |
| WO | WO 2014158617 | 10/2014 |
| WO | WO 2014162181 | 10/2014 |
| WO | WO 2014162306 | 10/2014 |
| WO | WO 2014163705 | 10/2014 |
| WO | WO 2014168655 | 10/2014 |
| WO | WO 2014179391 | 11/2014 |
| WO | WO 2014181336 | 11/2014 |
| WO | WO 2014189974 | 11/2014 |
| WO | WO 2014190329 | 11/2014 |
| WO | WO 2014191994 | 12/2014 |
| WO | WO 2014193951 | 12/2014 |
| WO | WO 2014194178 | 12/2014 |
| WO | WO 2014197924 | 12/2014 |
| WO | WO 2014200764 | 12/2014 |
| WO | WO 2014201384 | 12/2014 |
| WO | WO 2014201452 | 12/2014 |
| WO | WO 2014205064 | 12/2014 |
| WO | WO 2014205223 | 12/2014 |
| WO | WO 2014205234 | 12/2014 |
| WO | WO 2014207699 | 12/2014 |
| WO | WO 2014210124 | 12/2014 |
| WO | WO 2014210299 | 12/2014 |
| WO | WO 2015003183 | 1/2015 |
| WO | WO 2015006575 | 1/2015 |
| WO | WO 2015009503 | 1/2015 |
| WO | WO 2015013238 | 1/2015 |
| WO | WO 2015020971 | 2/2015 |
| WO | WO 2015028986 | 3/2015 |
| WO | WO 2015031898 | 3/2015 |
| WO | WO 2015051430 | 4/2015 |
| WO | WO 2015052663 | 4/2015 |
| WO | WO 2015057407 | 4/2015 |
| WO | WO 2015057735 | 4/2015 |
| WO | WO 2015057995 | 4/2015 |
| WO | WO 2015061378 | 4/2015 |
| WO | WO 2015061431 | 4/2015 |
| WO | WO 2015061463 | 4/2015 |
| WO | WO 2015061533 | 4/2015 |
| WO | WO 2015061558 | 4/2015 |
| WO | WO 2015075128 | 5/2015 |
| WO | WO 2015081775 | 6/2015 |
| WO | WO 2015089334 | 6/2015 |
| WO | WO 2015092554 | 6/2015 |
| WO | WO 2015120122 | 8/2015 |
| WO | WO 2015125024 | 8/2015 |
| WO | WO 2015127264 | 8/2015 |
| WO | WO 2015127283 | 8/2015 |
| WO | WO 2015128739 | 9/2015 |
| WO | WO 2015128741 | 9/2015 |
| WO | WO 2015128747 | 9/2015 |
| WO | WO 2015132667 | 9/2015 |
| WO | WO 2015132668 | 9/2015 |
| WO | WO 2015135050 | 9/2015 |
| WO | WO 2015142648 | 9/2015 |
| WO | WO 2015142834 | 9/2015 |
| WO | WO 2015148241 | 10/2015 |
| WO | WO 2015171190 | 11/2015 |
| WO | WO 2015171743 | 11/2015 |
| WO | WO 2015179181 | 11/2015 |
| WO | WO 2015191604 | 12/2015 |
| WO | WO 2015191839 | 12/2015 |
| WO | WO 2015195823 | 12/2015 |
| WO | WO 2016005803 | 1/2016 |
| WO | WO 2016011185 | 1/2016 |
| WO | WO 2016020918 | 2/2016 |
| WO | WO 2016027272 | 2/2016 |
| WO | WO 2016059533 | 4/2016 |
| WO | WO 2016065158 | 4/2016 |
| WO | WO 2016073741 | 5/2016 |
| WO | WO 2016077783 | 5/2016 |
| WO | WO 2016083551 | 6/2016 |
| WO | WO 2016093877 | 6/2016 |
| WO | WO 2016097337 | 6/2016 |
| WO | WO 2016108181 | 7/2016 |
| WO | WO 2016133950 | 8/2016 |
| WO | WO 2017062640 | 4/2017 |
| WO | WO 2017087701 | 5/2017 |
| WO | WO 2017096157 | 6/2017 |
| WO | WO 2017100927 | 6/2017 |
| WO | WO 2017101232 | 6/2017 |
| WO | WO 2017117388 | 7/2017 |
| WO | WO 2017127939 | 8/2017 |
| WO | WO 2017136287 | 8/2017 |
| WO | WO 2017136596 | 8/2017 |
| WO | WO 2017165810 | 9/2017 |
| WO | WO 2017189040 | 11/2017 |
| WO | WO 2017192960 | 11/2017 |
| WO | WO 2017196511 | 11/2017 |
| WO | WO 2017196909 | 11/2017 |
| WO | WO 2017196977 | 11/2017 |
| WO | WO 2017197064 | 11/2017 |
| WO | WO 2017197065 | 11/2017 |
| WO | WO 2017218671 | 12/2017 |
| WO | WO 2018017886 | 1/2018 |

OTHER PUBLICATIONS

Bernard et al., "Aortic Valve Area Evolution After Percutaneous Aortic Valvuloplasty," European Heart Journal, vol. 11, No. 2, Jul. 1990, pp. 98-107.

BlueCross BlueShield of Northern Carolina Corporate Medical Policy "Balloon valvuloplasty, Percutaneous", (Jun. 1994).

Cimino et al., "Physics of Ultrasonic Surgery using Tissue Fragmentation: Part I and Part II", Ultrasound in Medicine and Biology, vol. 22, No. 1, Jun. 1996, pp. 89-100, and pp. 101-117.

Cimino, "Ultrasonic surgery: power quantification and efficiency optimization", Aesthetic surgery journal, vol. 21, No. 3, May 2001, 233-241.

Cowell et al., "A randomized Trial of Intensive Lipid-Lowering Therapy in Calcific Aortic Stenosis," NEJM, vol. 352, No. 23, Jun. 9, 2005, pp. 2389-2397.

De Korte et al., "Characterization of Plaque Components and Vulnerability with Intravascular Ultrasound Elastography," Physics in Medicine & Biology, vol. 45, No. 6, Jun. 2000, pp. 1465-1475.

Feldman, "Restenosis Following Successful Balloon Valvuloplasty: Bone Formation in Aortic Valve Leaflets," Cathet Cardiovasc Diagn,

(56) References Cited

OTHER PUBLICATIONS vol. 29, No. 1, May 1993, pp. 1-7.
Fitzgerald et al., "Intravascular Sonotherapy Decreased Neointimal Hyperplasia After Stent Implantation in Swine," Circulation, vol. 103, No. 14, Apr. 10, 2001, pp. 1828-1831.
Freeman et al., "Ultrasonic Aortic Valve Decalcification: Serial Doppler Echocardiographic Follow Up," Journal of the American College of Cardiology, vol. 16, No. 3, Sep. 1990, pp. 623-630.
Greenleaf et al., "Selected Methods for Imaging Elastic Properties of Biological Tissues", Annual Review of Biomedical Engineering, vol. 5, Apr. 2003, pp. 57-78.
Gunn et al., "New Developments in Therapeutic Ultrasound-Assisted Coronary Angioplasty," Curr Interv Cardiol Rep., vol. 1, No. 4, Dec. 1990, pp. 281-290.
Guzman et al., "Bioeffects Caused by Changes in Acoustic Cavitation Bubble Density and Cell Concentration: A Unified Explanation Based on Cell-to-Bubble Ratio and Blast Radius," Ultrasound in Medicine & Biology, vol. 29, No. 8, Aug. 2003, pp. 1211-1222.
Hallgrimsson et al., "Chronic Non-Rheumatic Aortic Valvular Disease: a Population Study Based on Autopsies", Journal of Chronic Diseases, vol. 32, No. 5, Jan. 1979, pp. 355-363.
Isner et al., "Contrasting Histoarchitecture of Calcified Leaflets from Stenotic Bicuspid Versus Stenotic Tricuspid Aortic Valves", Journal of the American College of Cardiology, vol. 15, No. 5, Apr. 1990, pp. 1104-1108.
Lung et al., "A Prospective Survey of Patients with Valvular Heart Disease in Europe: The Euro Heart Survey on Valvular Heart Disease," European Heart Journal, vol. 24, No. 13, Mar. 2003, pp. 1231-1243.
McBride et al "Aortic Valve Decalcification," The Journal of Thoracic and Cardiovascular Surgery, vol. 100, No. 1, Jul. 1990, pp. 36-42.
Miller et al., "Lysis and Sonoporation of Epidermoid and Phagocytic Monolayer Cells by Diagnostic Ultrasound Activation of Contrast Agent Gas Bodies," Ultrasound in Medicine & Biology, vol. 27, No. 8, Aug. 2001, pp. 1107-1113.
Mohler, "Mechanisms of Aortic Valve Calcification," The American Journal of Cardiology, vol. 94, No. 11, Dec. 1, 2004, pp. 1396-1402, A6.
Otto et al., "Three-Year Outcome After Balloon Aortic Valvuloplasty. Insights into Prognosis of Valvular Aortic Stenosis," Circulation, vol. 89, Feb. 1994, pp. 642-650.
Passik et al., "Temporal Changes in the Causes of Aortic Stenosis: A Surgical Pathologic Study of 646 Cases," Mayo Clinic Proceedings, vol. 62, No. 2, Feb. 1987, pp. 119-123.
Quaden et al., "Percutaneous Aortic Valve Replacement: Resection Before Implantation," European Journal of Cardio-thorac Surgery, vol. 27, No. 5, Jan. 2005, pp. 836-840.
Riebman et al., Poster Session 1125—New Concepts in the Management of Patients with Aortic Valve Disease, 1125-135, "Valve Renovation in Calcific Aortic Stenosis: Safety and Feasibility of a Novel Endoaortic System for Native Valve Preservation," Abstracts—Valvular Heart Disease, Journal of the American College of Cardiology, vol. 43, No. 5, Supplement 2, Mar. 2004, p. 435A.
Rosenschein et al., "Percutaneous Transluminal Therapy of Occluded Saphenous Vein Grafts," Circulation, vol. 99, Jan. 1999, pp. 26-29.
Sakata et al., "Percutaneous Balloon Aortic Valvuloplasty: Antegrade Transseptal vs. Conventional Retrograde Transarterial Approach," Catheterization & Cardiovascular Interventions, vol. 64, No. 3, Mar. 2005, pp. 314-321.
Sasaki et al., "Scanning Electron Microscopy and Fourier Transformed Infrared Spectroscopy Analysis of Bone Removal Using Er:YAG and CO2 Lasers," Journal of Periodontalogy, vol. 73, No. 6, Jun. 2002, pp. 643-652.
The CoreValve System Medtronic, 2012, 4 Pages. (Applicant points out, in accordance with MPEP 609.04(a), that the year of publication, 2012, is sufficiently earlier than the effective U.S. filing date, so that the particular month of publication is not in issue.).
Van Den Brand et al., "Histological Changes in the Aortic Valve after Balloon Dilation: Evidence for a Delayed Healing Process", British Heart Journal, vol. 67, No. 6, Jun. 1992, pp. 445-449.
Verdaasdonck et al., "The Mechanism of Action of the Ultrasonic Tissue Resectors Disclosed Using High-Speed and Thermal Imaging Techniques," SPIE, vol. 3594, Jan. 1999, pp. 221-232.
Voelker et al., "Intraoperative Valvuloplasty in Calcific Aortic Stenosis: A Study Comparing the Mechanism of a Novel Expandable Device with conventional Balloon Dilation," American Heart Journal, vol. 122, No. 5, Nov. 1991, pp. 1327-1333.
Waller et al., "Catheter Balloon Valvuloplasty of Stenotic Aortic Valves—Part II: Balloon Valvuloplasty During Life Subsequent Tissue Examination," Clinical Cardiology, vol. 14, No. 11, Nov. 1991, pp. 924-930.
Wang et al., "Balloon Aortic Valvuloplasty," Progress in Cardiovascular Diseases, vol. 40, No. 1, Jul.-Aug. 1997, pp. 27-36.
Wilson et al., "Elastography—The Movement Begins," Physics in Medicine and Biology, vol. 45, No. 6, Jun. 2000, pp. 1409-1421.
Yock et al, "Catheter-Based Ultrasound Thrombolysis," Circulation, vol. 95, No. 6, Mar. 18, 1997, pp. 1360-1362.
Search Report and Written Opinion dated Apr. 19, 2014 PCT Application No. PCT/US2012/061215.
Search Report and Written Opinion dated Apr. 19, 2014 PCT Application No. PCT/US2012/061219.
International Search Report and Written Opinion dated Dec. 10, 2012; International Application No. PCT/US2012/043636; Applicant: Foundry Newco XII, Inc.; 21 pages.
Search Report and Written Opinion dated Dec. 6, 2016 for PCT Application No. PCT/US2016/047831.
International Search Report and Written Opinion dated Jul. 11, 2018 for PCT Application No. PCT/US2018/027990, 15 pages.
International Search Report and Written Opinion dated Jun. 28, 2018 for PCT Application No. PCT/US2018/027983, 15 pages.
International Search Report and Written Opinion for International Application No. PCT/US2014/029549, mailed Mar. 2, 2015, 20 pages.
International Search Report and Written Opinion dated May 1, 2012; International Application No. PCT/US2011/065627; Applicant: Foundry Newco XII, Inc.; 10 pages.
International Search report and Written Opinion for International App. No. PCT/US2005/044543, dated May 22, 2007, 8 pages.
International Search Report and Written Opinion for International Application No. PCT/US2014/038849, mailed Oct. 20, 2014, 14 pages.
International Search Report and Written Opinion for International App. No. PCT/US2014/014704, mailed Sep. 4, 2014, 18 pages.
Prosecution History from U.S. Appl. No. 15/490,008, dated Oct. 3, 2018 through Oct. 22, 2019, 89 pp.
European Office Action, EP Appl. No. 18 724 024.7, mailed Oct. 12, 2022, 5 pages.

* cited by examiner

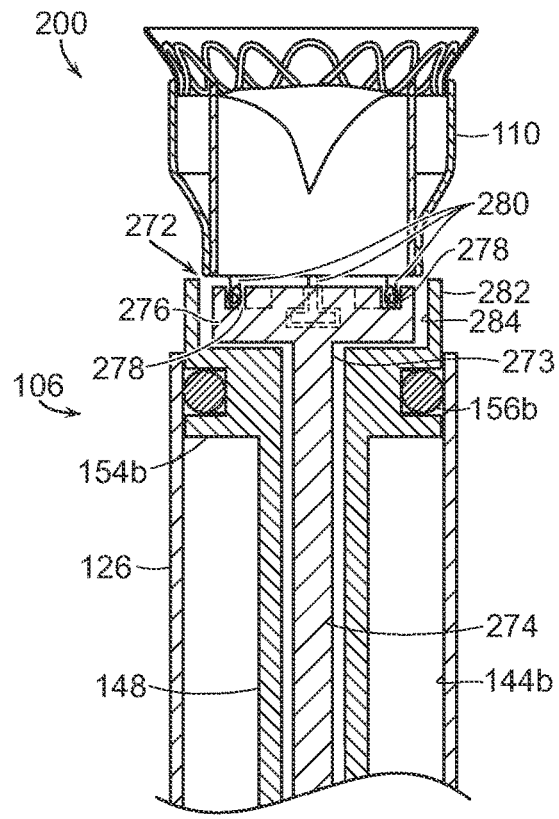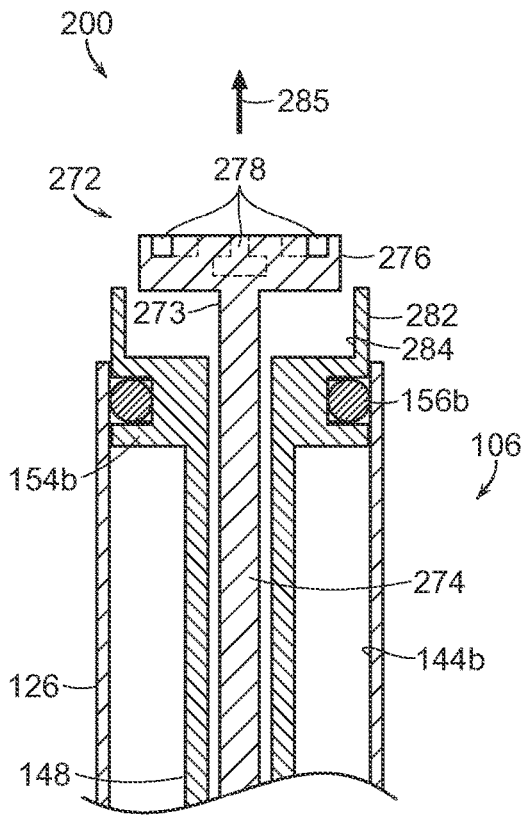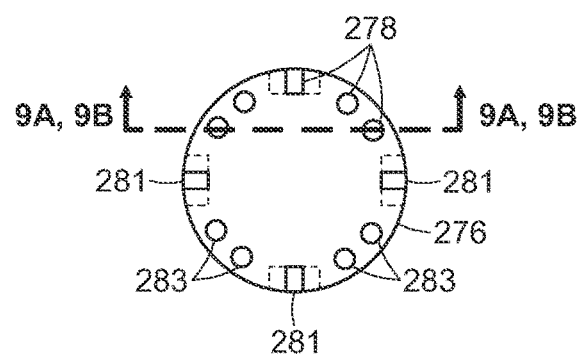

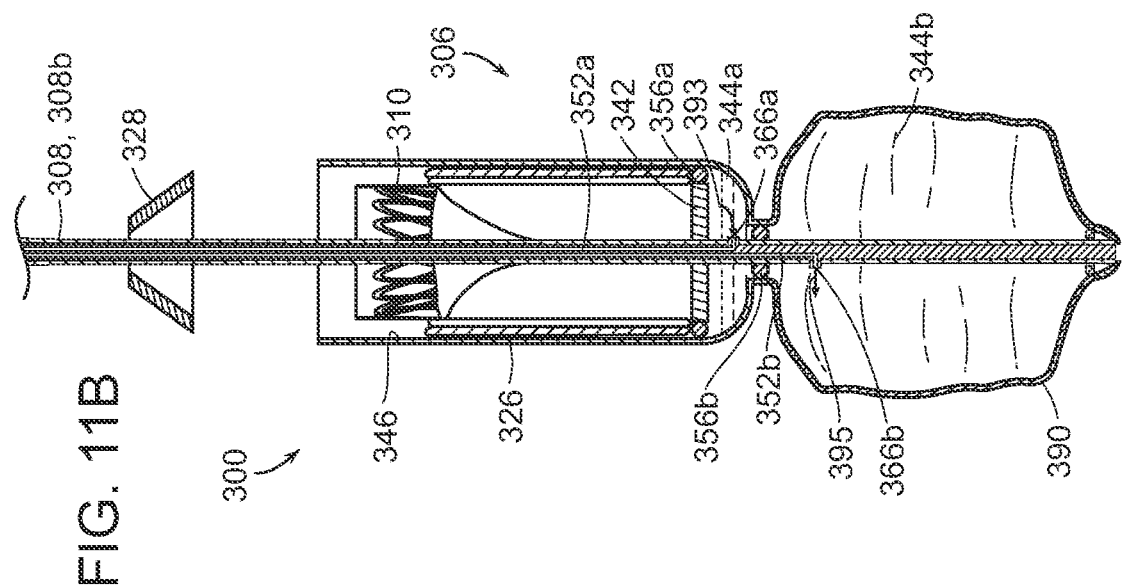
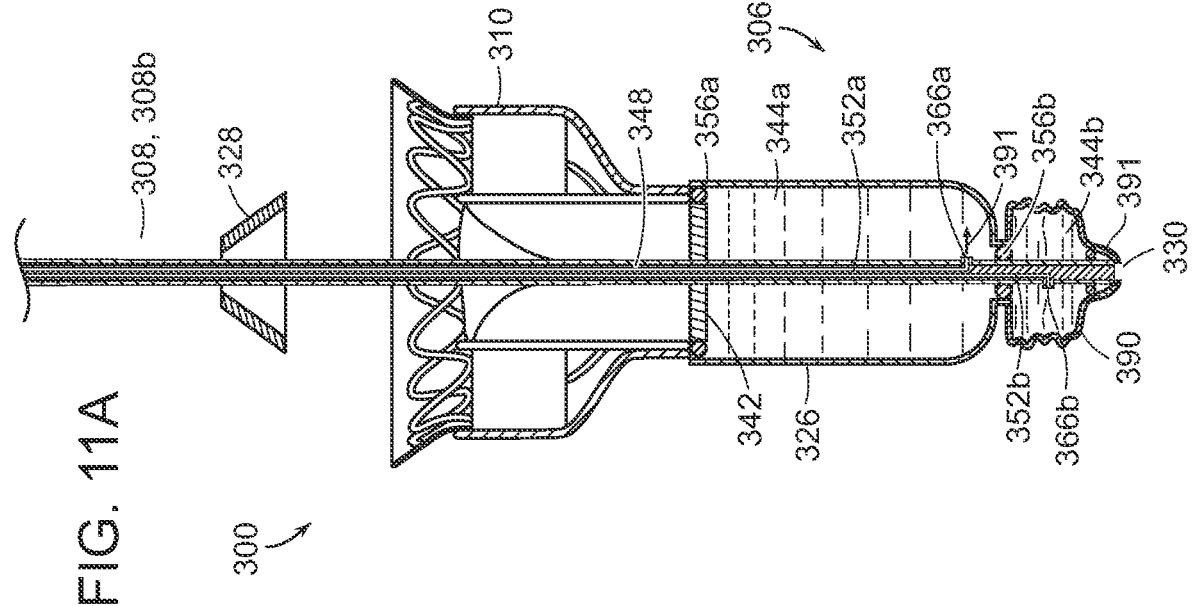

HYDRAULIC SYSTEMS FOR DELIVERING PROSTHETIC HEART VALVE DEVICES AND ASSOCIATED METHODS

CROSS-REFERENCE TO RELATED APPLICATIONS

This application is a continuation of U.S. patent application Ser. No. 16/752,137, filed Jan. 24, 2020, which is a divisional of U.S. patent application Ser. No. 15/490,008, filed Apr. 18, 2017, now U.S. Pat. No. 10,575,950, the entire contents of each of which is incorporated by reference herein.

The present application incorporates the subject matter of (1) International Patent Application No. PCT/US2014/029549, filed Mar. 14, 2014, (2) International Patent Application No. PCT/US2012/061219, filed Oct. 19, 2012, (3) International Patent Application No. PCT/US2012/061215, filed Oct. 19, 2012, (4) International Patent Application No. PCT/US2012/043636, filed Jun. 21, 2012. The present application also incorporates the subject matter of U.S. application Ser. No. 15/490,024, filed Apr. 18, 2017.

TECHNICAL FIELD

The present technology relates generally to systems for delivering prosthetic heart valve devices. In particular, several embodiments of the present technology are related to hydraulic systems for percutaneously delivering prosthetic heart valve devices into mitral valves and associated methods.

BACKGROUND

Heart valves can be affected by several conditions. For example, mitral valves can be affected by mitral valve regurgitation, mitral valve prolapse and mitral valve stenosis. Mitral valve regurgitation is abnormal leaking of blood from the left ventricle into the left atrium caused by a disorder of the heart in which the leaflets of the mitral valve fail to coapt into apposition at peak contraction pressures. The mitral valve leaflets may not coapt sufficiently because heart diseases often cause dilation of the heart muscle, which in turn enlarges the native mitral valve annulus to the extent that the leaflets do not coapt during systole. Abnormal backflow can also occur when the papillary muscles are functionally compromised due to ischemia or other conditions. More specifically, as the left ventricle contracts during systole, the affected papillary muscles do not contract sufficiently to effect proper closure of the leaflets.

Mitral valve prolapse is a condition when the mitral leaflets bulge abnormally up in to the left atrium. This can cause irregular behavior of the mitral valve and lead to mitral valve regurgitation. The leaflets may prolapse and fail to coapt because the tendons connecting the papillary muscles to the inferior side of the mitral valve leaflets (chordae tendineae) may tear or stretch. Mitral valve stenosis is a narrowing of the mitral valve orifice that impedes filling of the left ventricle in diastole.

Mitral valve regurgitation is often treated using diuretics and/or vasodilators to reduce the amount of blood flowing back into the left atrium. Surgical approaches (open and intravascular) for either the repair or replacement of the valve have also been used to treat mitral valve regurgitation. For example, typical repair techniques involve cinching or resecting portions of the dilated annulus. Cinching, for example, includes implanting annular or peri-annular rings that are generally secured to the annulus or surrounding tissue. Other repair procedures suture or clip the valve leaflets into partial apposition with one another.

Alternatively, more invasive procedures replace the entire valve itself by implanting mechanical valves or biological tissue into the heart in place of the native mitral valve. These invasive procedures conventionally require large open thoracotomies and are thus very painful, have significant morbidity, and require long recovery periods. Moreover, with many repair and replacement procedures, the durability of the devices or improper sizing of annuloplasty rings or replacement valves may cause additional problems for the patient. Repair procedures also require a highly skilled cardiac surgeon because poorly or inaccurately placed sutures may affect the success of procedures.

Less invasive approaches to aortic valve replacement have been implemented in recent years. Examples of pre-assembled, percutaneous prosthetic valves include, e.g., the CoreValve Revalving® System from Medtronic/Corevalve Inc. (Irvine, CA, USA) and the EdwardsSapien® Valve from Edwards Lifesciences (Irvine, CA, USA). Both valve systems include an expandable frame and a tri-leaflet bioprosthetic valve attached to the expandable frame. The aortic valve is substantially symmetric, circular, and has a muscular annulus. The expandable frames in aortic applications have a symmetric, circular shape at the aortic valve annulus to match the native anatomy, but also because tri-leaflet prosthetic valves require circular symmetry for proper coaptation of the prosthetic leaflets. Thus, aortic valve anatomy lends itself to an expandable frame housing a replacement valve since the aortic valve anatomy is substantially uniform, symmetric, and fairly muscular. Other heart valve anatomies, however, are not uniform, symmetric or sufficiently muscular, and thus transvascular aortic valve replacement devises may not be well suited for other types of heart valves.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. The headings provided herein are for convenience only.

FIGS. 9A and 9B are cross-sectional views of a distal portion of a delivery system for a prosthetic heart valve device in a partially retained state (FIG. 9A) and in a fully deployed state (FIG. 9B) in accordance with another embodiment of the present technology.

FIG. 9C is a top view of an engagement pedestal of the delivery system of FIGS. 9A and 9B configured in accordance with an embodiment of the present technology.

FIGS. 11A and 11B are enlarged, partially schematic cross-sectional views of a distal portion of a trans-septal delivery system in a partially expanded deployment configuration (FIG. 11A) and a containment configuration (FIG. 11B) in accordance with another embodiment of the present technology.

DETAILED DESCRIPTION

Figure 1:
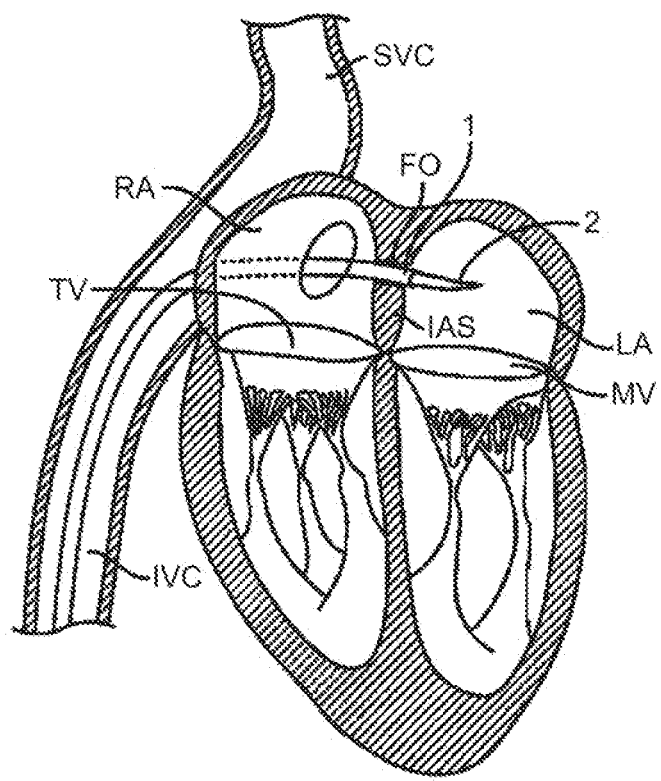
FIG. 1 is a schematic, cross-sectional illustration of the heart showing an antegrade approach to the native mitral valve from the venous vasculature in accordance with various embodiments of the present technology.

The present technology is generally directed to hydraulic systems for delivering prosthetic heart valve devices and associated methods. Specific details of several embodiments of the present technology are described herein with reference to FIGS. 1-25. Although many of the embodiments are described with respect to devices, systems, and methods for delivering prosthetic heart valve devices to a native mitral valve, other applications and other embodiments in addition to those described herein are within the scope of the present technology. For example, at least some embodiments of the present technology may be useful for delivering prosthetics to other valves, such as the tricuspid valve or the aortic valve. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

With regard to the terms "distal" and "proximal" within this description, unless otherwise specified, the terms can reference relative positions of portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a location where blood flows into the device (e.g., inflow region), and distal can refer to a downstream position or a location where blood flows out of the device (e.g., outflow region).

Overview

Several embodiments of the present technology are directed to delivery systems and mitral valve replacement devices that address the unique challenges of percutaneously replacing native mitral valves and are well-suited to be recaptured in a percutaneous delivery device after being partially deployed for repositioning or removing the device. Compared to replacing aortic valves, percutaneous mitral valve replacement faces unique anatomical obstacles that render percutaneous mitral valve replacement significantly more challenging than aortic valve replacement. First, unlike relatively symmetric and uniform aortic valves, the mitral valve annulus has a non-circular D-shape or kidney-like shape, with a non-planar, saddle-like geometry often lacking symmetry. The complex and highly variable anatomy of mitral valves makes it difficult to design a mitral valve prosthesis that conforms well to the native mitral annulus of specific patients. As a result, the prosthesis may not fit well with the native leaflets and/or annulus, which can leave gaps that allows backflow of blood to occur. For example, placement of a cylindrical valve prosthesis in a native mitral valve may leave gaps in commissural regions of the native valve through which perivalvular leaks may occur.

Current prosthetic valves developed for percutaneous aortic valve replacement are unsuitable for use in mitral valves. First, many of these devices require a direct, structural connection between the stent-like structure that contacts the annulus and/or leaflets and the prosthetic valve. In several devices, the stent posts which support the prosthetic valve also contact the annulus or other surrounding tissue. These types of devices directly transfer the forces exerted by the tissue and blood as the heart contracts to the valve support and the prosthetic leaflets, which in turn distorts the valve support from its desired cylindrical shape. This is a concern because most cardiac replacement devices use tri-leaflet valves, which require a substantially symmetric, cylindrical support around the prosthetic valve for proper opening and closing of the three leaflets over years of life. As a result, when these devices are subject to movement and forces from the annulus and other surrounding tissues, the prostheses may be compressed and/or distorted causing the prosthetic leaflets to malfunction. Moreover, a diseased mitral annulus is much larger than any available prosthetic aortic valve. As the size of the valve increases, the forces on the valve leaflets increase dramatically, so simply increasing the size of an aortic prosthesis to the size of a dilated mitral valve annulus would require dramatically thicker, taller leaflets, and might not be feasible.

In addition to its irregular, complex shape, which changes size over the course of each heartbeat, the mitral valve annulus lacks a significant amount of radial support from surrounding tissue. Compared to aortic valves, which are completely surrounded by fibro-elastic tissue that provides sufficient support for anchoring a prosthetic valve, mitral valves are bound by muscular tissue on the outer wall only. The inner wall of the mitral valve anatomy is bound by a thin vessel wall separating the mitral valve annulus from the inferior portion of the aortic outflow tract. As a result, significant radial forces on the mitral annulus, such as those imparted by an expanding stent prostheses, could lead to collapse of the inferior portion of the aortic tract. Moreover, larger prostheses exert more force and expand to larger dimensions, which exacerbates this problem for mitral valve replacement applications.

The chordae tendineae of the left ventricle may also present an obstacle in deploying a mitral valve prosthesis. Unlike aortic valves, mitral valves have a maze of cordage under the leaflets in the left ventricle that restrict the movement and position of a deployment catheter and the replacement device during implantation. As a result, deploying, positioning and anchoring a valve replacement device on the ventricular side of the native mitral valve annulus is complicated.

Embodiments of the present technology provide systems, methods and apparatus to treat heart valves of the body, such as the mitral valve, that address the challenges associated with the anatomy of the mitral valve and provide for repositioning and removal of a partially deployed device. The apparatus and methods enable a percutaneous approach using a catheter delivered intravascularly through a vein or artery into the heart, or through a cannula inserted through the heart wall. For example, the apparatus and methods are particularly well-suited for trans-septal and trans-apical approaches, but can also be trans-atrial and direct aortic delivery of a prosthetic replacement valve to a target location in the heart. Additionally, the embodiments of the devices and methods as described herein can be combined with many known surgeries and procedures, such as known methods of accessing the valves of the heart (e.g., the mitral valve or triscuspid valve) with antegrade or retrograde approaches, and combinations thereof.

The systems and methods described herein facilitate controlled delivery of a prosthetic heart valve device using trans-apical or trans-septal delivery approaches and allow resheathing of the prosthetic heart valve device after partial deployment of the device to reposition and/or remove the device. The delivery systems can include two independent fluid chambers that are interchangeably filled with fluid and drained of fluid to initiate deployment and resheathing of the prosthetic device. This facilitates hydraulic control and power for both proximal and distal movement of a capsule housing that provides for controlled delivery of the prosthetic heart valve device and inhibits uncontrolled movement of the delivery system resulting from forces associated with expansion of the prosthetic heart valve device (e.g., axial jumping, self-ejection, etc.). In addition, the hydraulic delivery systems disclosed herein can inhibit longitudinal translation of the prosthetic heart valve device relative to the treatment site while the prosthetic heart valve device moves between the containment configuration and the deployment configuration. This allows the clinician to position the sheathed prosthetic heart valve device at the desired target site for deployment, and then deploy the device at that target site without needing to compensate for any axial movement caused by deployment.

Access to the Mitral Valve

To better understand the structure and operation of valve replacement devices in accordance with the present technology, it is helpful to first understand approaches for implanting the devices. The mitral valve or other type of atrioventricular valve can be accessed through the patient's vasculature in a percutaneous manner. By percutaneous it is meant that a location of the vasculature remote from the heart is accessed through the skin, typically using a surgical cut down procedure or a minimally invasive procedure, such as using needle access through, for example, the Seldinger technique. The ability to percutaneously access the remote vasculature is well known and described in the patent and medical literature. Depending on the point of vascular access, access to the mitral valve may be antegrade and may rely on entry into the left atrium by crossing the inter-atrial septum (e.g., a trans-septal approach). Alternatively, access to the mitral valve can be retrograde where the left ventricle is entered through the aortic valve. Access to the mitral valve may also be achieved using a cannula via a trans-apical approach. Depending on the approach, the interventional tools and supporting catheter(s) may be advanced to the heart intravascularly and positioned adjacent the target cardiac valve in a variety of manners, as described herein.

FIG. 1 illustrates a stage of a trans-septal approach for implanting a valve replacement device. In a trans-septal approach, access is via the inferior vena cava IVC or superior vena cava SVC, through the right atrium RA, across the inter-atrial septum IAS, and into the left atrium LA above the mitral valve MV. As shown in FIG. 1, a catheter 1 having a needle 2 moves from the inferior vena cava IVC into the right atrium RA. Once the catheter 1 reaches the anterior side of the inter-atrial septum IAS, the needle 2 advances so that it penetrates through the septum, for example at the fossa ovalis FO or the foramen ovale into the left atrium LA. At this point, a guidewire replaces the needle 2 and the catheter 1 is withdrawn. FIG. 1 also shows the tricuspid valve TV between the right atrium RA and the right ventricle.

Figure 2:
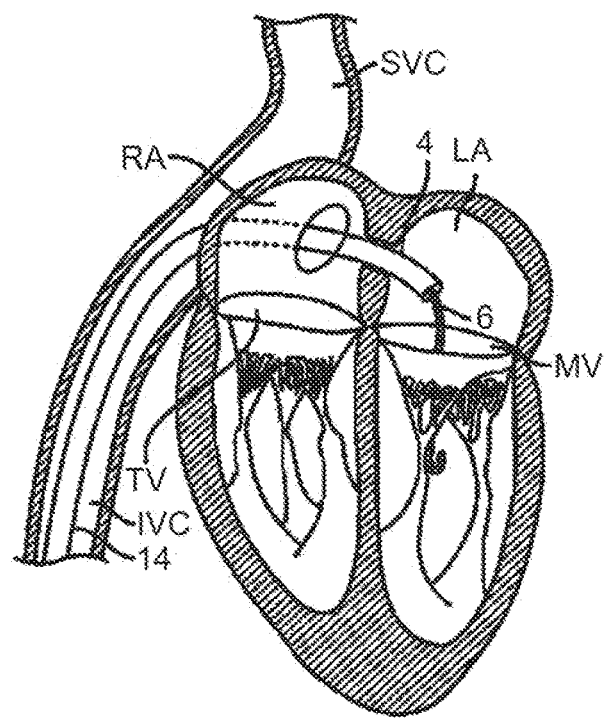
FIG. 2 is a schematic, cross-sectional illustration of the heart showing access through the inter-atrial septum (IAS) maintained by the placement of a guide catheter over a guidewire in accordance with various embodiments of the present technology.

FIG. 2 illustrates a subsequent stage of a trans-septal approach in which guidewire 6 and guide catheter 4 pass through the inter-atrial septum IAS. The guide catheter 4 provides access to the mitral valve for implanting a valve replacement device in accordance with the technology.

In an alternative antegrade approach (not shown), surgical access may be obtained through an intercostal incision, preferably without removing ribs, and a small puncture or incision may be made in the left atrial wall. A guide catheter passes through this puncture or incision directly into the left atrium, sealed by a purse string-suture.

The antegrade or trans-septal approach to the mitral valve, as described above, can be advantageous in many respects. For example, antegrade approaches will usually enable more precise and effective centering and stabilization of the guide catheter and/or prosthetic valve device. The antegrade approach may also reduce the risk of damaging the chordae tendinae or other subvalvular structures with a catheter or other interventional tool. Additionally, the antegrade approach may decrease risks associated with crossing the aortic valve as in retrograde approaches. This can be particularly relevant to patients with prosthetic aortic valves, which cannot be crossed at all or without substantial risk of damage.

Figure 3:
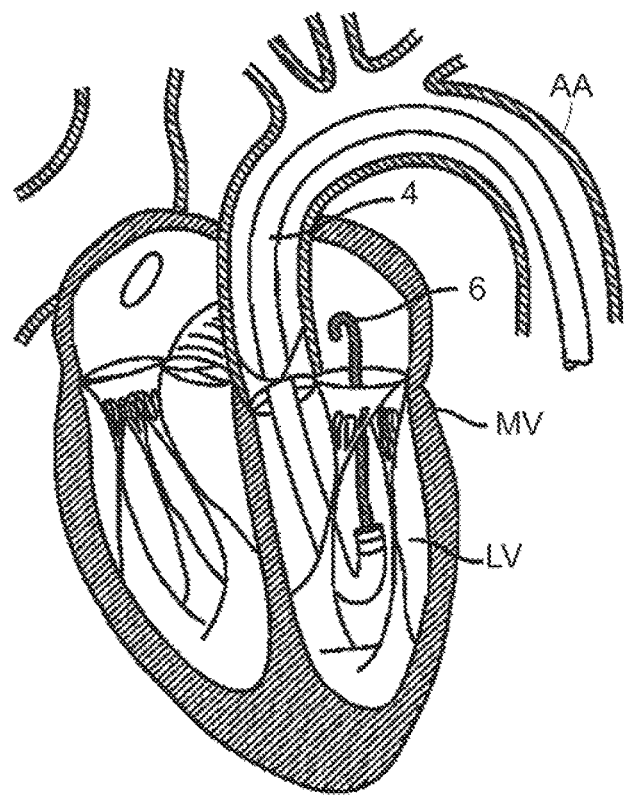
FIGS. 3 and 4 are schematic, cross-sectional illustrations of the heart showing retrograde approaches to the native mitral valve through the aortic valve and arterial vasculature in accordance with various embodiments of the present technology.
Figure 4:
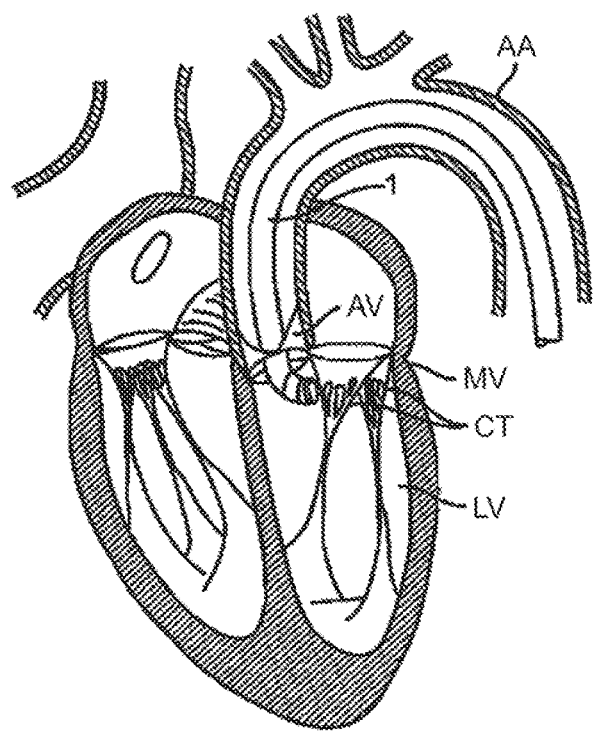

FIGS. 3 and 4 show examples of a retrograde approaches to access the mitral valve. Access to the mitral valve MV may be achieved from the aortic arch AA, across the aortic valve AV, and into the left ventricle LV below the mitral valve MV. The aortic arch AA may be accessed through a conventional femoral artery access route or through more direct approaches via the brachial artery, axillary artery, radial artery, or carotid artery. Such access may be achieved with the use of a guidewire 6. Once in place, a guide catheter 4 may be tracked over the guidewire 6. Alternatively, a surgical approach may be taken through an incision in the chest, preferably intercostally without removing ribs, and placing a guide catheter through a puncture in the aorta itself. The guide catheter 4 affords subsequent access to permit placement of the prosthetic valve device, as described in more detail herein. Retrograde approaches advantageously do not need a trans-septal puncture. Cardiologists also more commonly use retrograde approaches, and thus retrograde approaches are more familiar.

Figure 5:
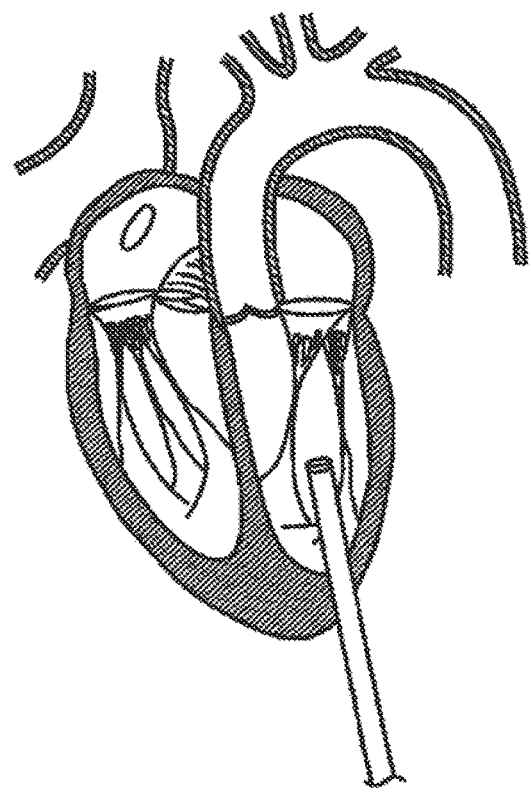
FIG. 5 is a schematic, cross-sectional illustration of the heart showing an approach to the native mitral valve using a trans-apical puncture in accordance with various embodiments of the present technology.

FIG. 5 shows a trans-apical approach via a trans-apical puncture. In this approach, access to the heart is via a thoracic incision, which can be a conventional open thoracotomy or sternotomy, or a smaller intercostal or sub-xyphoid incision or puncture. An access cannula is then placed through a puncture in the wall of the left ventricle at or near the apex of the heart. The catheters and prosthetic devices of the invention may then be introduced into the left ventricle through this access cannula. The trans-apical approach provides a shorter, straighter, and more direct path to the mitral or aortic valve. Further, because it does not involve intravascular access, the trans-apical approach does not require training in interventional cardiology to perform the catheterizations required in other percutaneous approaches.

Selected Embodiments of Delivery Systems for Prosthetic Heart Valve Devices

Figure 6:
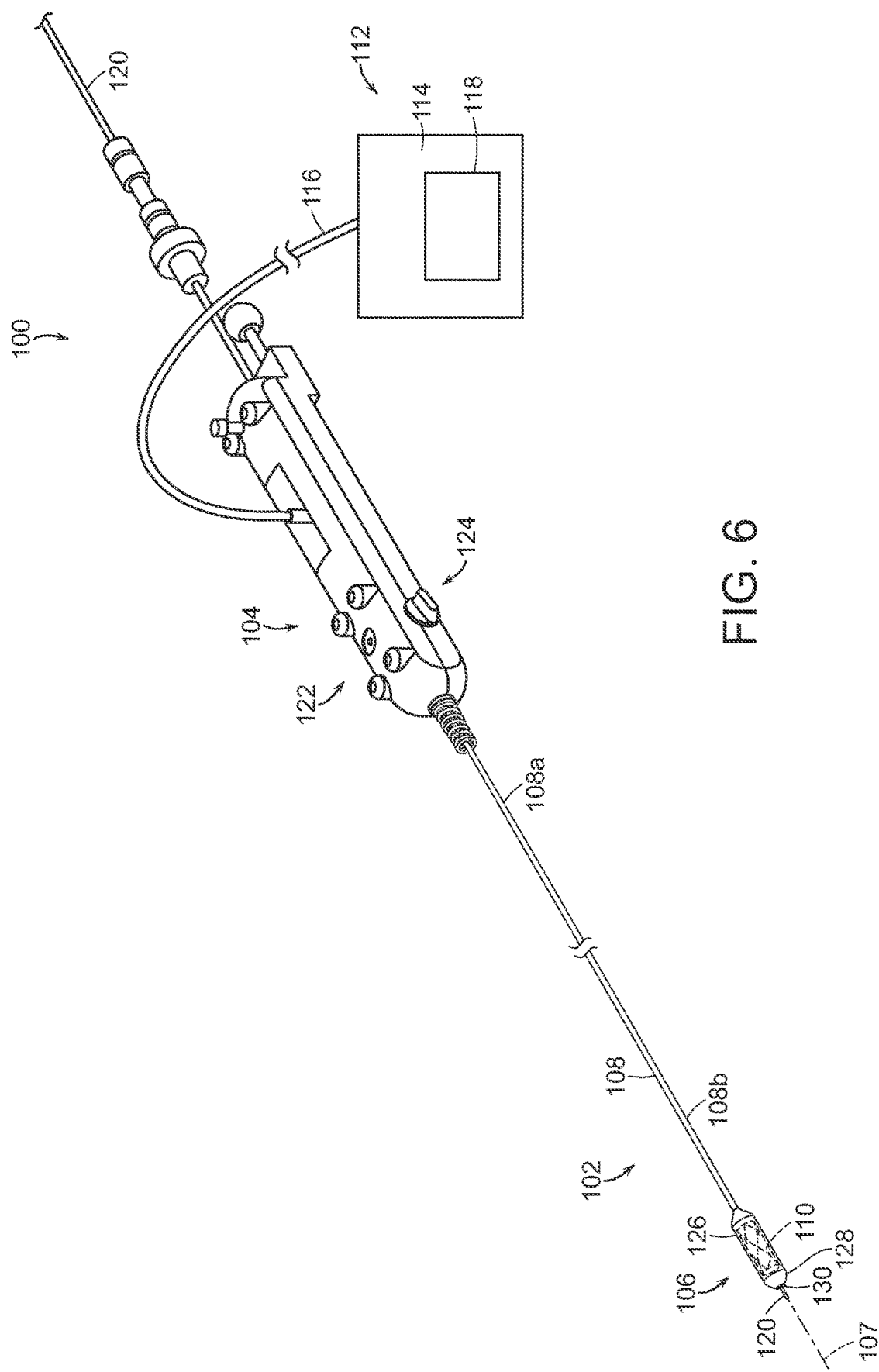
FIG. 6 is an isometric view of a system for delivering a prosthetic heart valve device configured in accordance with an embodiment of the present technology.

FIG. 6 is an isometric view of a hydraulic system 100 ("system 100") for delivering a prosthetic heart valve device configured in accordance with an embodiment of the present technology. The system 100 includes a catheter 102 having an elongated catheter body 108 ("catheter body 108") and a delivery capsule 106. The catheter body 108 can include a proximal portion 108a coupled to a hand held control unit 104 ("control unit 104") and a distal portion 108b carrying the delivery capsule 106. The delivery capsule 106 can be configured to contain a prosthetic heart valve device 110 (shown schematically in broken lines). The control unit 104 can provide steering capability (e.g., 360 degree rotation of the delivery capsule 106, 180 degree rotation of the delivery capsule 106, 3-axis steering, 2-axis steering, etc.) used to deliver the delivery capsule 106 to a target site (e.g., to a native mitral valve) and deploy the prosthetic heart valve device 110 at the target site. The catheter 102 can be configured to travel over a guidewire 120, which can be used to guide the delivery capsule 106 into the native heart valve. The system 100 can also include a fluid assembly 112 configured to supply fluid to and receive fluid from the catheter 102 to hydraulically move the delivery capsule 106 and deploy the prosthetic heart valve device 110.

The fluid assembly 112 includes a fluid source 114 and a fluid line 116 fluidically coupling the fluid source 114 to the catheter 102. The fluid source 114 may contain a flowable substance (e.g., water, saline, etc.) in one or more reservoirs. The fluid line 116 can include one or more hoses, tubes, or other components (e.g., connectors, valves, etc.) through which the flowable substance can pass from the fluid source 114 to the catheter 102 and/or through which the flowable substance can drain from the catheter 102 to the fluid source 114. In other embodiments, the fluid line 116 can deliver the flowable substance to the catheter 102 from a first reservoir of the fluid source 114 and drain the flowable substance from the catheter 102 to a separate reservoir. The fluid assembly 112 can also include one or more pressurization devices (e.g., a pump), fluid connectors, fittings, valves, and/or other fluidic components that facilitate moving the fluid to and/or from the fluid source 114. As explained in further detail below, the movement of the flowable substance to and from the fluid assembly 112 can be used to deploy the prosthetic heart valve device 110 from the delivery capsule 106 and/or resheathe the prosthetic heart valve device 110 after at least partial deployment.

In certain embodiments, the fluid assembly 112 may comprise a controller 118 that controls the movement of fluid to and from the catheter 102. The controller 118 can include, without limitation, one or more computers, central processing units, processing devices, microprocessors, digital signal processors (DSPs), and/or application-specific integrated circuits (ASICs). To store information, for example, the controller 118 can include one or more storage elements, such as volatile memory, non-volatile memory, read-only memory (ROM), and/or random access memory (RAM). The stored information can include, pumping programs, patient information, and/or other executable programs. The controller 118 can further include a manual input device (e.g., a keyboard, a touch screen, etc.) and/or an automated input device (e.g., a computer, a data storage device, servers, network, etc.). In still other embodiments, the controller 118 may include different features and/or have a different arrangement for controlling the flow of fluid into and out of the fluid source 114.

The control unit 104 can include a control assembly 122 and a steering mechanism 124. For example, the control assembly 122 can include rotational elements, such as a knob, that can be rotated to rotate the delivery capsule 106 about its longitudinal axis 107. The control assembly 122 can also include features that allow a clinician to control the hydraulic deployment mechanisms of the delivery capsule 106 and/or the fluid assembly 112. For example, the control assembly 122 can include buttons, levers, and/or other actuators that initiate unsheathing and/or resheathing the prosthetic heart valve device 110. The steering mechanism 124 can be used to steer the catheter 102 through the anatomy by bending the distal portion 108b of the catheter body 108 about a transverse axis. In other embodiments, the control unit 104 may include additional and/or different features that facilitate delivering the prosthetic heart valve device 110 to the target site.

The delivery capsule 106 includes a housing 126 configured to carry the prosthetic heart valve device 110 in the containment configuration and, optionally, an end cap 128 that extends distally from the housing 126 and encloses the prosthetic heart valve device 110 in the housing 126. The end cap 128 can have an opening 130 at its distal end through which the guidewire 120 can be threaded to allow for guidewire delivery to the target site. As shown in FIG. 6, the end cap 128 can also have an atraumatic shape (e.g., a partially spherical shape, a frusto-conical shape, blunt configuration, rounded configuration, etc.) to facilitate atraumatic delivery of the delivery capsule 106 to the target site. In certain embodiments, the end cap 128 can also house a portion of the prosthetic heart valve device 110. The housing 126 and/or the end cap 128 can be made of metal, polymers, plastic, composites, combinations thereof, or other materials capable of holding the prosthetic heart valve device 110. As discussed in further detail below, the delivery capsule 106 is hydraulically driven via the control unit 104 and/or the fluid assembly 112 between a containment configuration for holding the prosthetic heart valve device 110 and a deployment configuration for at least partially deploying the prosthetic heart valve device 110 at the target site. The delivery capsule 106 also allows for resheathing of the prosthetic heart valve device 110 after it has been partially deployed.

Figure 7A:
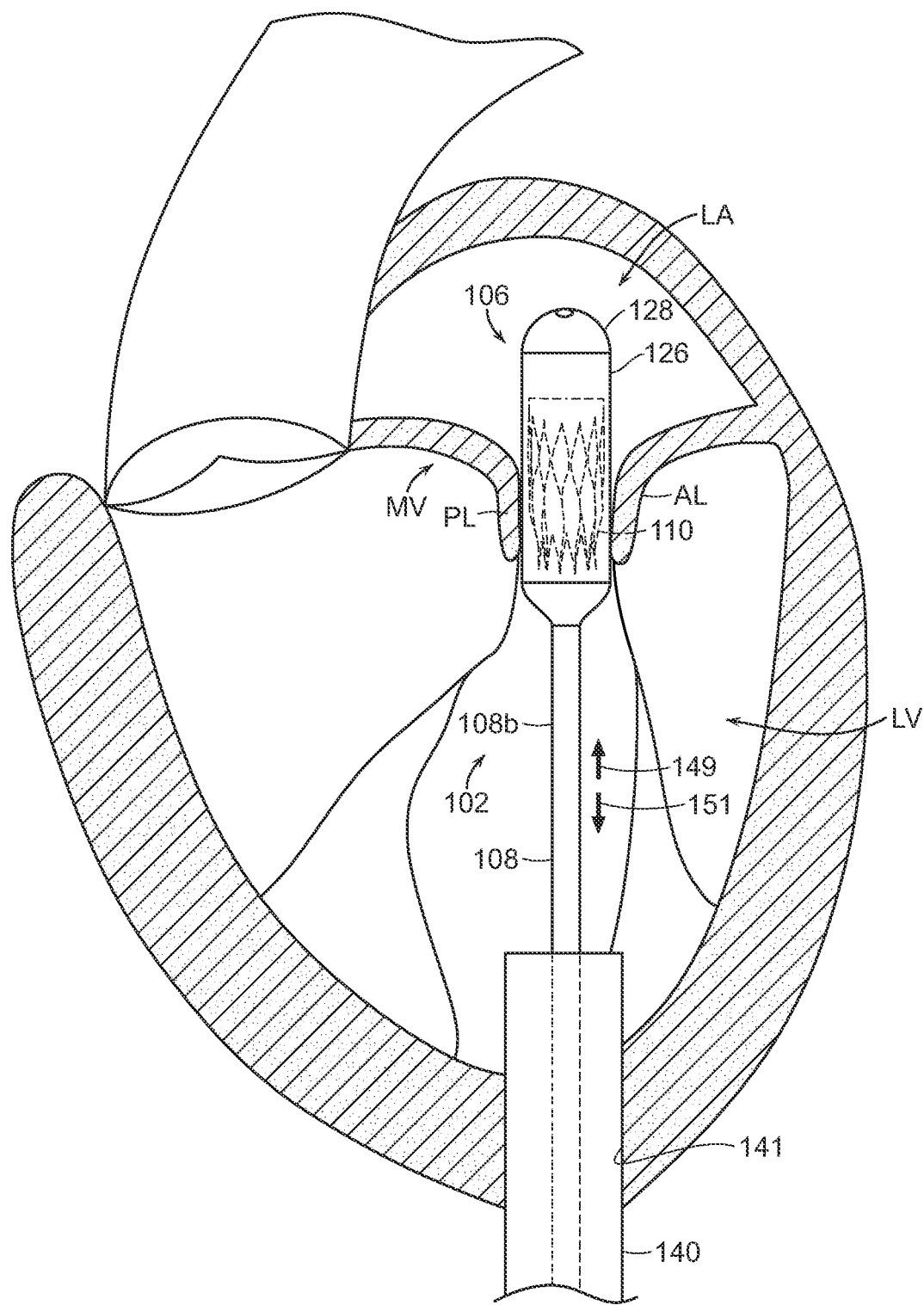
FIG. 7A is a partially schematic illustration of a distal portion of the system of FIG. 6 positioned in a native mitral valve of a heart using a trans-apical delivery approach in accordance with embodiments of the present technology.
Figure 7B:
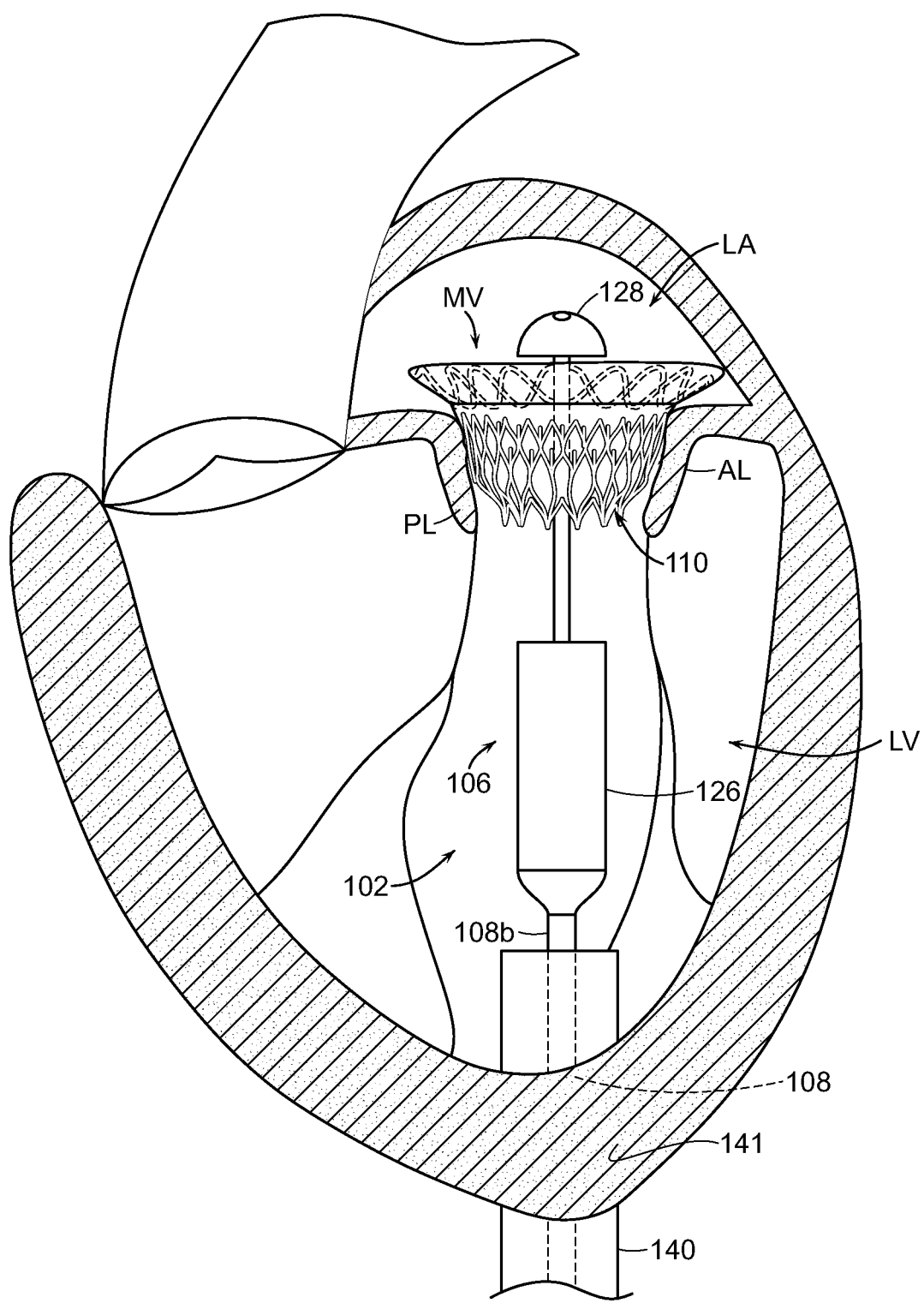
FIG. 7B is a partially schematic illustration of the distal portion of the system of FIG. 7A in a deployment configuration and a deployed prosthetic heart valve device in accordance with embodiments of the present technology.

FIG. 7A is a partially schematic illustration of a distal portion of the system 100 of FIG. 6 in the containment configuration positioned in a native mitral valve of a heart using a trans-apical delivery approach in accordance with embodiments of the present technology, and FIG. 7B is a partially schematic illustration of the system 100 in the deployment configuration. Referring to FIG. 7A, a guide catheter 140 can be positioned in a trans-apical opening 141 in the heart to provide access to the left ventricle LV, and the catheter 102 can extend through the guide catheter 140 such that the distal portion 108b of the catheter body 108 projects beyond the distal end of the guide catheter 140. The delivery capsule 106 is then positioned between a posterior leaflet PL and an anterior leaflet AL of a mitral valve MV. Using the control unit 104 (FIG. 6), the catheter body 108 can be moved in the superior direction (as indicated by arrow 149), the inferior direction (as indicated by arrow 151), and/or rotated along the longitudinal axis of the catheter body 108 to position the delivery capsule 106 at a desired location and orientation within the opening of the mitral valve MV.

Once at a target location, the delivery capsule 106 can be hydraulically driven from the containment configuration (FIG. 7A) towards the deployment configuration (FIG. 7B) to partially or fully deploy the prosthetic heart valve device 110 from the delivery capsule 106. For example, as explained in further detail below, the delivery capsule 106 can be hydraulically driven towards the deployment configuration by supplying a flowable liquid to a chamber of the delivery capsule 106 while also removing a flowable liquid from a separate chamber of the delivery capsule 106. The hydraulically controlled movement of the delivery capsule 106 is expected to reduce, limit, or substantially eliminate uncontrolled deployment of the prosthetic heart valve device 110 caused by forces associated with expansion of the prosthetic heart valve device 110, such as jumping, self-ejection, and/or other types of uncontrolled movement. For example, the delivery capsule 106 is expected to inhibit or prevent translation of the prosthetic heart valve device 110 relative to the catheter body 108 while at least a portion of the prosthetic heart valve device 110 expands.

Referring to FIG. 7B, in trans-apical delivery approaches, the prosthetic heart valve device 110 is deployed from the delivery capsule 106 by drawing the housing 126 proximally (i.e., further into the left ventricle LV) and, optionally, moving the end cap 128 distally (i.e., further into the left atrium LA). As the prosthetic heart valve device 110 exits the housing 126, the device 110 expands and presses against tissue on an inner surface of the annulus of the mitral valve MV to secure the device 110 in the mitral valve MV. The catheter 102 is also configured to partially or fully resheathe the prosthetic heart valve device 110 after partial deployment from the delivery capsule 106. For example, the delivery capsule 106 can be hydraulically driven back towards the containment configuration by transferring fluid into one chamber of the delivery capsule 106 and removing fluid from another chamber of the delivery capsule 106 in an opposite manner as that used for deployment. This resheathing ability allows the clinician to reposition the prosthetic heart valve device 110, in vivo, for redeployment within the mitral valve MV or remove the prosthetic heart valve device 110 from the patient after partial deployment. After full deployment of the prosthetic heart valve device 110, the end cap 128 can be drawn through the deployed prosthetic heart valve device 110 to again close the delivery capsule 106 and draw the catheter 102 proximally through the guide catheter 140 for removal from the patient. After removing the catheter 102, it can be cleaned and used to deliver additional prosthetic devices or it can be discarded.

Figure 8A:
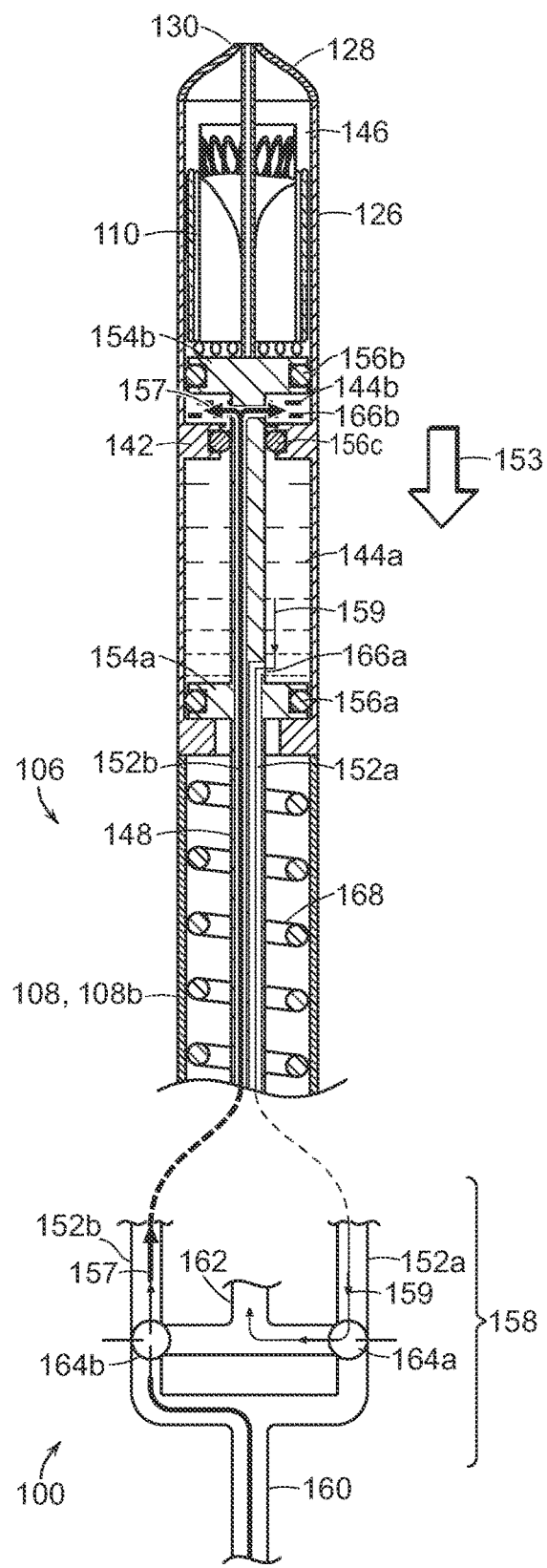
FIGS. 8A and 8B are partially schematic cross-sectional views of the delivery system of FIG. 6 in a containment configuration (FIG. 8A) and a deployment configuration (FIG. 8B) in accordance with an embodiment of the present technology.
Figure 8B:
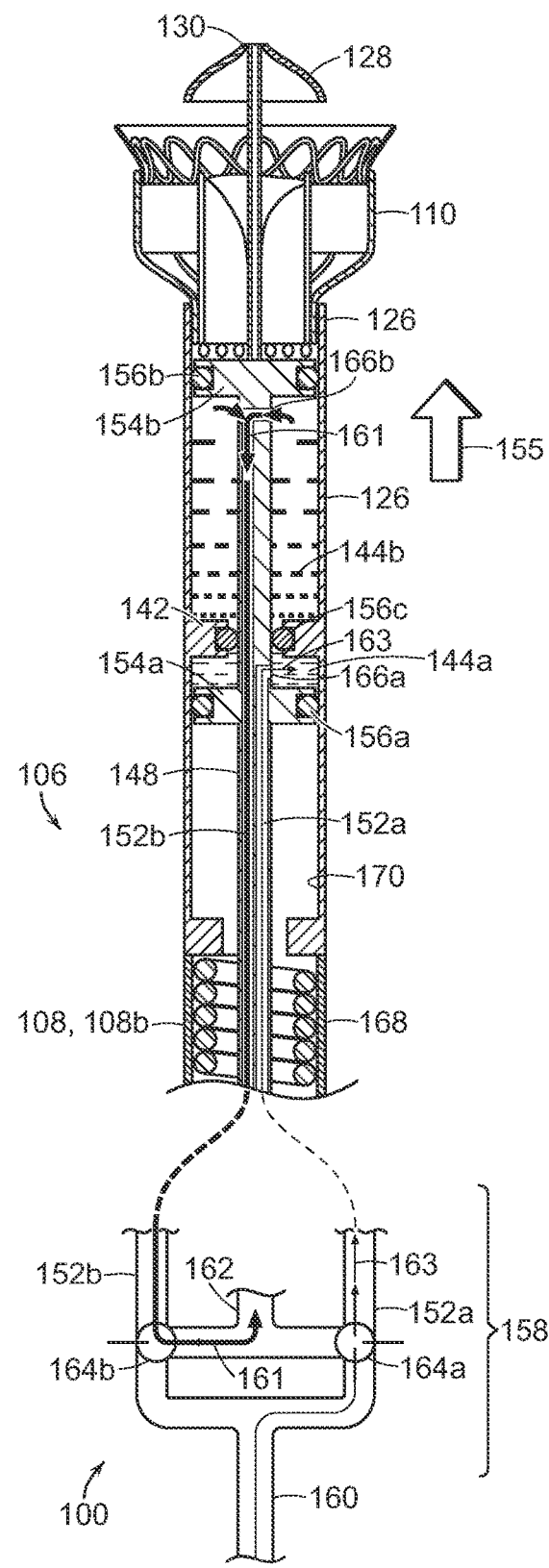

FIGS. 8A and 8B are partially schematic cross-sectional views of the delivery system 100 of FIG. 6 in the containment configuration (FIG. 8A) and the deployment configuration (FIG. 8B) in accordance with an embodiment of the present technology. As shown in FIGS. 8A and 8B, the distal portion 108b of the elongated catheter body 108 carries the delivery capsule 106. The delivery capsule 106 includes the housing 126 and a platform 142 that together define, at least in part, a first chamber 144a and a second chamber 144b (referred to collectively as "the chambers 144"). The first chamber 144a and the second chamber 144b are fluidically sealed from each other and from a compartment 146 in the housing 126 that is configured to contain the prosthetic heart valve device 110. The chambers 144 can be filled and drained to hydraulically drive the delivery capsule 106 between the containment configuration (FIG. 8A) for holding the prosthetic heart valve device 110 and the deployment configuration (FIG. 8B) for at least partially deploying the prosthetic heart valve device 100. As shown in FIG. 8A, for example, the housing 126 of the delivery capsule 106 is urged proximally (in the direction of arrow 153) towards the deployment configuration when fluid is at least partially drained from the first chamber 144a (as indicated by arrow 159) while fluid is being delivered to the second chamber 144b (as indicated by arrow 157). The proximal translation of the housing 126 allows the prosthetic heart valve device 110 to at least partially deploy from the housing 126 (FIG. 8B) and expand such that it may engage surrounding tissue of a native mitral valve. As shown in FIG. 8B, the housing 126 is urged distally back towards the containment configuration to resheathe at least a portion of the prosthetic heart valve device 110 when fluid is at least partially drained from the second chamber 144b (as indicated by arrow 161) while fluid is being delivered into the first chamber 144b (as indicated by arrow 163).

The platform 142 extends at least partially between the inner wall of the housing 126 to divide the housing 126 into the first chamber 144a and the second chamber 144b. The platform 142 can be integrally formed as a part of the housing 126, such as an inwardly extending flange. Thus, the platform 142 can be made from the same material as the housing 126 (e.g., metal, polymers, plastic, composites, combinations thereof, or other). In other embodiments, the platform 142 may be a separate component that at least partially separates the two chambers 144 from each other.

As shown in FIGS. 8A and 8B, a fluid delivery shaft 148 ("shaft 148") extends through the catheter body 108, into the housing 126 of the delivery capsule 106, and through the platform 142. At its proximal end (not shown), the shaft 148 is coupled to a fluid source (e.g., the fluid source 114 of FIG. 6) and includes one or more fluid lines 152 (identified individually as a first line 152a and a second line 152b) that can deliver and/or drain fluid to and/or from the chambers 144. The fluid lines 152 can be fluid passageways or lumens integrally formed within the shaft 148, such as channels through the shaft itself, or the fluid lines 152 may be tubes or hoses positioned within one or more hollow regions of the shaft 148. The first line 152a is in fluid communication with the first chamber 144a via a first opening 166a in the first fluid line 152a, and the second line 152b is in fluid communication with the second chamber 144b via a second opening 166b in the second fluid line 152b. In other embodiments, the first and second chambers 144a and 144b can be in fluid communication with more than one fluid line. For example, each chamber 144 may have a dedicated fluid delivery line and dedicated fluid drain line.

The shaft 148 can also include a first flange or pedestal 154a and a second flange or pedestal 154b (referred to together as "flanges 154") that extend outwardly from the shaft 148 to define the proximal and distal ends of the first and second chambers 144a and 144b, respectively. Accordingly, the first chamber 144a is defined at a distal end by a proximal-facing surface of the platform 142, at a proximal end by a distally-facing surface of the first flange 154a, and by the interior wall of the housing 126 extending therebetween. The second chamber 144b is defined at a proximal end by a distal-facing surface of the platform 142, at a distal end by a proximally-facing surface of the second flange 154b, and by the interior wall of the housing 126 extending therebetween. The compartment 146 containing the prosthetic heart valve device 110 can be defined by a distal-facing surface of the second flange 154b, the end cap 128, and the interior wall of the housing 126 extending therebetween. The shaft 148 and the flanges 154 can be integrally formed or separate components, and can be made from metal, polymers, plastic, composites, combinations thereof, and/or other suitable materials for containing fluids. The flanges 148 are fixed with respect to the shaft 148. Sealing members 156 (identified individually as first through third sealing members 156a-c, respectively), such as O-rings, can be positioned around or within the flanges 154 and/or the platform 142 to fluidically seal the chambers 144 from other portions of the delivery capsule 106. For example, the first and second sealing members 156a and 156b can be positioned in recesses of the corresponding first and second flanges 154a and 154b to fluidically seal the flanges 154 against the interior wall of the housing 126, and the third sealing member 156c can be positioned within a recess of the platform 142 to fluidically seal the platform 142 to the shaft 148. In other embodiments, the system 100 can include additional and/or differently arranged sealing members to fluidically seal the chambers 144.

The fluid lines 152 are in fluid communication with a manifold 158 at a proximal portion of the system 100 and in communication with the fluid assembly 112 (FIG. 6). The manifold 158 may be carried by the control unit 104 (FIG. 6) or it may be integrated with the fluid assembly 112 (FIG. 6). As shown in FIGS. 8A and 8B, the manifold 158 can include a fluid delivery lumen 160 that bifurcates to allow for delivery of fluid to the first and second fluid lines 152a and 152b and a drain lumen 162 that bifurcates to allow for removal of fluid from the first and second fluid lines 152a and 152b. The delivery lumen 160 and the drain lumen 162 can be placed in fluid communication with the fluid source 114 (FIG. 6) to allow fluid to move between the fluid source 114 to the chambers 144. In other embodiments, each fluid line 152 can have a dedicated delivery lumen and a dedicated drain lumen, which are in turn fluidly coupled to separate fluid reservoirs in the fluid source 114 (FIG. 6).

The manifold 158 further includes one or more valves 164 (referred to individually as a first valve 164a and a second valve 164b) that regulate fluid flow to and from the chambers 144. The first valve 164a is in fluid communication with the first fluid line 152a, the delivery lumen 160 (or a portion thereof), and the drain line 162 (or a portion thereof) to regulate fluid to and from the first chamber 144a. The second valve 164b is in fluid communication with the second fluid line 152b, the delivery lumen 160 (or a portion thereof), and the drain line 162 (or a portion thereof) to regulate fluid to and from the second chamber 144b. The valves 164 can be three-way valves and/or other suitable valves for regulating fluid to and from the fluid lines 152.

As shown in FIG. 8A, in the initial containment configuration, the first chamber 144a is at least partially filled with fluid and the second chamber 144b includes little to no fluid. To fully or partially unsheathe the prosthetic heart valve device 110, the second valve 164b opens the second fluid line 152b and closes the drain line 162. This allows fluid to flow from the delivery lumen 160, through the second fluid line 152b, and into the second chamber 144b via the second opening 166b (as indicated by arrows 157), while simultaneously blocking fluid from draining into the drain line 162. As fluid is delivered to the second chamber 144b, fluid also drains from the first chamber 144a. To do this, the first valve 164a closes the first line 152a proximal to the first valve 164a (i.e., such that the first line 152a is not in fluid communication with the delivery lumen 160) and opens the drain lumen 162 so that fluid exits the first chamber 144a via the first opening 166a, travels along the first fluid line 152a, and into the drain lumen 162 via the first valve 164a (as indicated by arrows 159). In certain embodiments, fluid is transferred to the second chamber 144b and from the first chamber 144a simultaneously and, optionally, in equal quantities so that the same amount of fluid transferred out of the first chamber 144a is transferred into the second chamber 144b. In other embodiments, different amounts of fluid are drained from and transferred to the chambers 144. This concurrent transfer of fluid into the second chamber 144b while draining fluid from the first chamber 144a drives the housing 126 proximally in the direction of arrow 153, which unsheathes the prosthetic heart valve device 110 and allows it to at least partially expand. As shown in FIG. 8B, this proximal movement of the housing 126 creates an open chamber 170 defined by the distal facing surface of the housing 126 and the proximal-facing surface of the flange 154a.

As shown in FIG. 8B, during deployment of the prosthetic heart valve device 110, the delivery capsule 106 axially restrains an outflow portion of the prosthetic heart valve device 110 while an inflow portion of the prosthetic heart valve device 110 is deployed from the delivery capsule 106. After at least partial deployment, the fluid chambers 144 can be pressurized and drained in an inverse manner to move the housing 126 distally (in the direction of arrow 155) back toward the containment configuration and at least partially resheathe the prosthetic heart valve device 110. For resheathing, the second valve 164b is placed in fluid communication with the drain lumen 162 and closes the second fluid line 152b proximal to the second valve 164b so that fluid drains from the second chamber 144b via the second opening 166b, through the second fluid line 152b, and into the drain lumen 162 (as indicated by arrows 161). As fluid exits the second chamber 144b, fluid is also delivered to the first chamber 144a. That is, the first valve 164a is placed in fluid communication with the delivery lumen 160 to deliver fluid into the first chamber 144a via the first opening 166a of the first fluid line 152a (as indicated by arrows 163). Again, the fluid can be transferred simultaneously and/or in equal proportions from the second chamber 144b and to the first chamber 144a. This transfer of fluid into the first chamber 144a and from the second chamber 144b drives the housing 126 distally in the direction of arrow 155 to controllably resheathe the prosthetic heart valve device 110 such that at least a portion of the prosthetic heart valve device 110 is again positioned within the compartment 146. This partial or full resheathing of the prosthetic heart valve device 110 allows a clinician to reposition or remove the prosthetic heart valve device 110 after partial deployment. The hydraulic movement of the housing 126 is expected to provide controlled deployment and resheathing of the prosthetic heart valve device 110.

As the delivery capsule 106 moves between the containment configuration and the deployment configuration, the housing 126 moves slideably with respect to the longitudinal axis of the shaft 148, while the prosthetic heart valve device 110 at least substantially maintains its longitudinal position relative to the catheter body 108. That is, the delivery capsule 106 can substantially prevent longitudinal translation of the prosthetic heart valve device 110 relative to the catheter body 108 while the prosthetic heart valve device 110 moves between the containment configuration (FIG. 8A) and the deployment configuration (FIG. 8B). This allows the clinician to position the sheathed prosthetic heart valve device 110 at the desired target site for deployment, and then deploy the device 110 at that target site without needing to compensate for any axial movement of the device 110 as it reaches full expansion (e.g., as would need to be taken into account if the device 110 was pushed distally from the housing 126).

As further shown in FIGS. 8A and 8B, the system 100 may also include a biasing device 168 that acts on the housing 126 to urge the housing 126 toward the containment configuration. The biasing device 168 compresses as the housing 126 moves to the deployment configuration (FIG. 8B) to apply more force on the housing 126 in a distal direction toward the containment configuration. In certain embodiments, the biasing device 168 acts continuously on the housing 126 urging it toward the containment configuration, and in other embodiments the biasing device 168 only acts on the housing 126 as it is compressed during deployment. In the illustrated embodiment, the biasing device 168 is a spring, but in other embodiments the biasing device can include other features that urge the housing 126 toward the containment configuration. The biasing device 168 limits or substantially prevents opening of the delivery capsule 106 attributable to the forces produced by the expanding prosthetic heart valve device 110. For example, an unsheathed portion of the prosthetic heart valve device 110 can expand outwardly from the partially opened delivery capsule 106 while the biasing device 168 inhibits further opening of the delivery capsule 106.

The system 100 shown in FIGS. 8A and 8B allows for delivery of the prosthetic heart valve device 110 to a mitral valve from the left ventricle (e.g., via a trans-apical approach shown in FIGS. 7A and 7B). For example, the hydraulic delivery mechanism moves the housing 126 proximally toward the distal portion 108b of the catheter body 108 to deploy the prosthetic heart valve device 110 (e.g., as shown in FIG. 7A), and once the prosthetic heart valve device 110 is fully deployed, the end cap 128 can be moved proximally from the left atrium and into the left ventricle through the deployed device 110.

FIGS. 9A and 9B are side cross-sectional views of a distal portion of a delivery system 200 for a prosthetic heart valve device 110 in a retained state (FIG. 9A) and in a fully deployed state (FIG. 9B) in accordance with another embodiment of the present technology. The delivery system 200 can include various features at least generally similar to the features of the system 100 described above with reference to FIGS. 6-8B. For example, the delivery system 200 can be hydraulically driven by moving fluid to and from two separate chambers 144 (only the second chamber 144b shown in FIGS. 9A and 9B) to move the housing 126 between deployment and containment configurations. The delivery system 200 also includes the fluid delivery shaft 148 with flanges 154 that define the outer bounds of the chambers 144.

The delivery system 200 of FIGS. 9A and 9B further includes an engagement device 272 that is configured to maintain engagement between the delivery capsule 106 and the prosthetic heart valve device 110 after the prosthetic heart valve device 110 has been at least partially expanded. The engagement device 272 includes a shaft 274 that extends through (e.g., coaxially within) or alongside at least a portion of the fluid delivery shaft 148 and is controllable by a clinician from a proximal portion of the delivery system 200 (e.g., via the control unit 104 of FIG. 6). The shaft 274 can be a central or engagement shaft that includes a distal region 273 having a pedestal 276 with one or more engagement or attachment elements 278 that releasably mate with corresponding attachment features 280 extending from the outflow region of the prosthetic heart valve device 110.

The attachment elements 278 can be recesses or pockets that retain correspondingly shaped attachment features 280 (e.g., pins or projections) on an outflow region of the prosthetic heart valve device 110. For example, the attachment elements 278 can be circular pockets that receive eyelet-shaped attachment features 280 extending from the outflow region of the prosthetic heart valve device 110 and/or the attachment elements 278 can be T-shaped recesses that receive corresponding T-shaped attachment features 280 extending from the outflow region of the prosthetic heart valve device 110.

FIG. 9C is a top view of the pedestal 276 illustrating one arrangement of the attachment elements 278. The illustrated pedestal 276 includes four T-shaped recesses 281 spaced 90° apart from each other around the periphery of the pedestal 276 and circular pockets 283 spaced between the T-shaped recesses 281. The T-shaped recesses 281 may extend deeper into the pedestal 276 than the circular pockets 283 (e.g., as shown in FIGS. 9A and 9B), or the attachment elements 278 can have similar depths. In other embodiments, the pedestal 276 has different quantities and/or arrangements of T-shaped recesses 281 and/or the circular pockets 283 across the face of the pedestal 276. In further embodiments, the pedestal 276 can include differently shaped recesses and pockets that releasably mate with correspondingly-shaped attachment features on the prosthetic heart valve device 110. In still further embodiments, the engagement device 272 includes other features that releasably attach the prosthetic heart valve device 110 to the delivery system 200 before final release from the delivery system 200.

In the embodiment illustrated in FIGS. 9A and 9B, the second flange 154b includes a projection 282 that forms a recess 284 facing the prosthetic heart valve device 110, and the recess 284 at least partially receives the pedestal 276 to retain the attachment features 280 with the attachment elements 278. The projection 282 may extend toward the prosthetic heart valve device 110 beyond the surface of the pedestal 276 positioned therein such that the projection 282 at least partially constrains an end region of the prosthetic heart valve device 110 before full deployment. In other embodiments, the second flange 154b does not include the projection 282, and the pedestal 276 abuts an end surface of the second flange 154b and/or other outward-facing feature of the delivery capsule 106.

In operation, a clinician moves the delivery capsule 106 to the target site (e.g., in a native mitral valve) and hydraulically moves the housing 126 to unsheathe and at least partially expand the prosthetic heart valve device 110. When the prosthetic heart valve device 110 is substantially expanded (FIG. 9A), the engagement device 272 holds the prosthetic heart valve device 110 to the delivery system 200 in case the device 110 needs to be resheathed for repositioning or redeployment. This allows the clinician to again partially or fully resheathe the prosthetic heart valve device 110 to adjust its position or orientation with respect to the native valve. Referring to FIG. 9B, after the prosthetic heart valve device 110 is partially deployed at the appropriate location, the clinician can move the engagement shaft 274 in the direction of arrow 285 away from the remainder of the delivery capsule 106 and out of the recess 284 (e.g., in a distal direction when deployed trans-apically). This movement releases the mateably received attachment features 280 on the prosthetic heart valve device 110 from the corresponding attachment elements 278 to fully release the prosthetic heart valve device 110 from the delivery system 200. For example, the expansion of the previously restrained proximal-most portion of the prosthetic heart valve device 110 (e.g., restrained by the projection 282 of the flange 154b) results in a force that disengages the attachment features 280 from the attachment elements 278 and allows the device 110 to fully expand. In other embodiments, the engagement shaft 274 can remain stationary with respect to the prosthetic heart valve device 110 and the delivery capsule 106 (e.g., the housing 126, the flange 154b, etc.) can be moved away from the prosthetic heart valve device 110 (e.g., in a proximal direction when the device is deployed trans-apically) to disengage the attachment features 280 from the attachment elements 278.

Figure 10A:
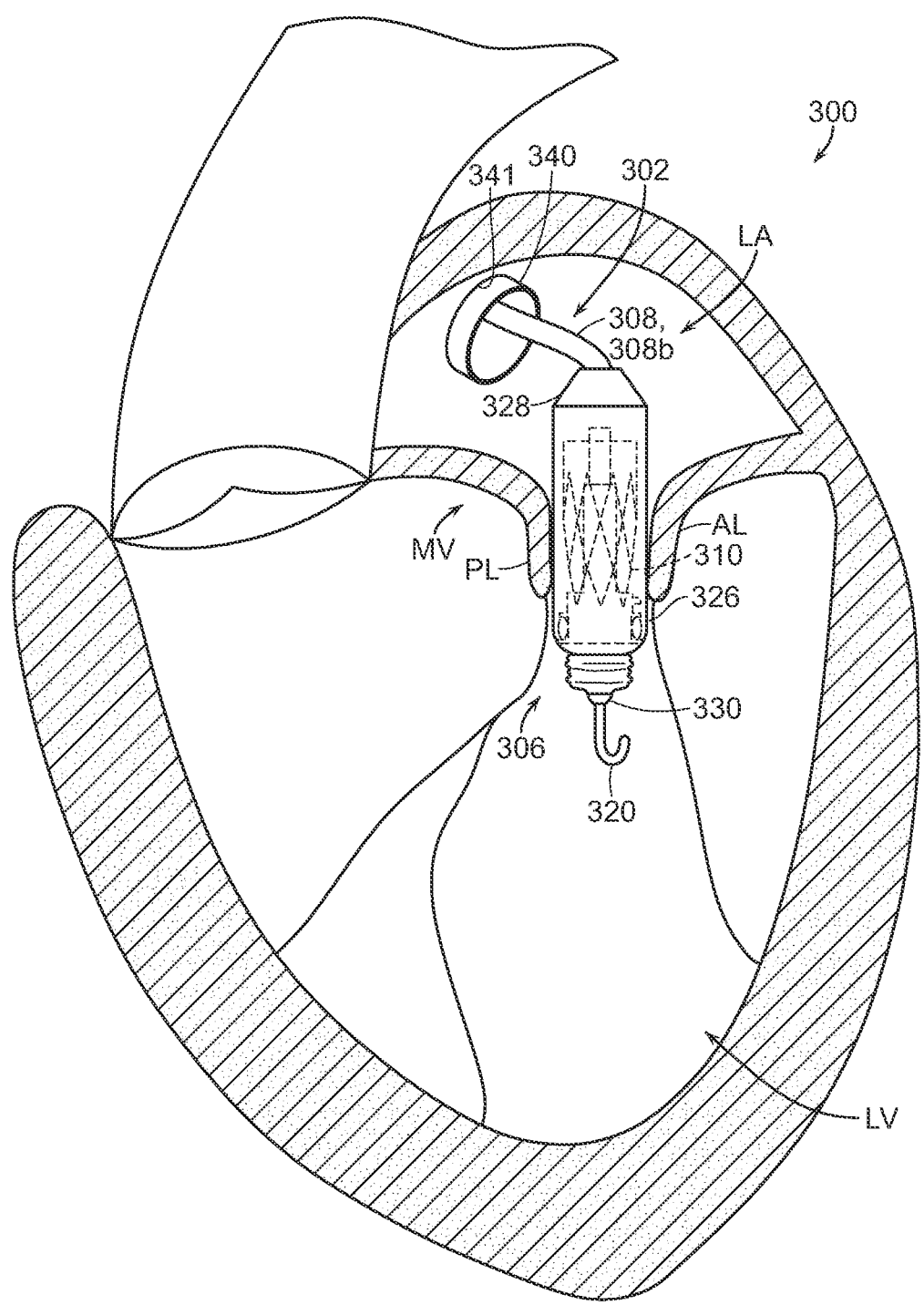
FIGS. 10A-10C are a series of partially schematic illustrations of a distal portion of a delivery system deploying a prosthetic a prosthetic heart valve device within a native mitral valve of a heart using a trans-septal approach in accordance with further embodiments of the present technology.
Figure 10B:
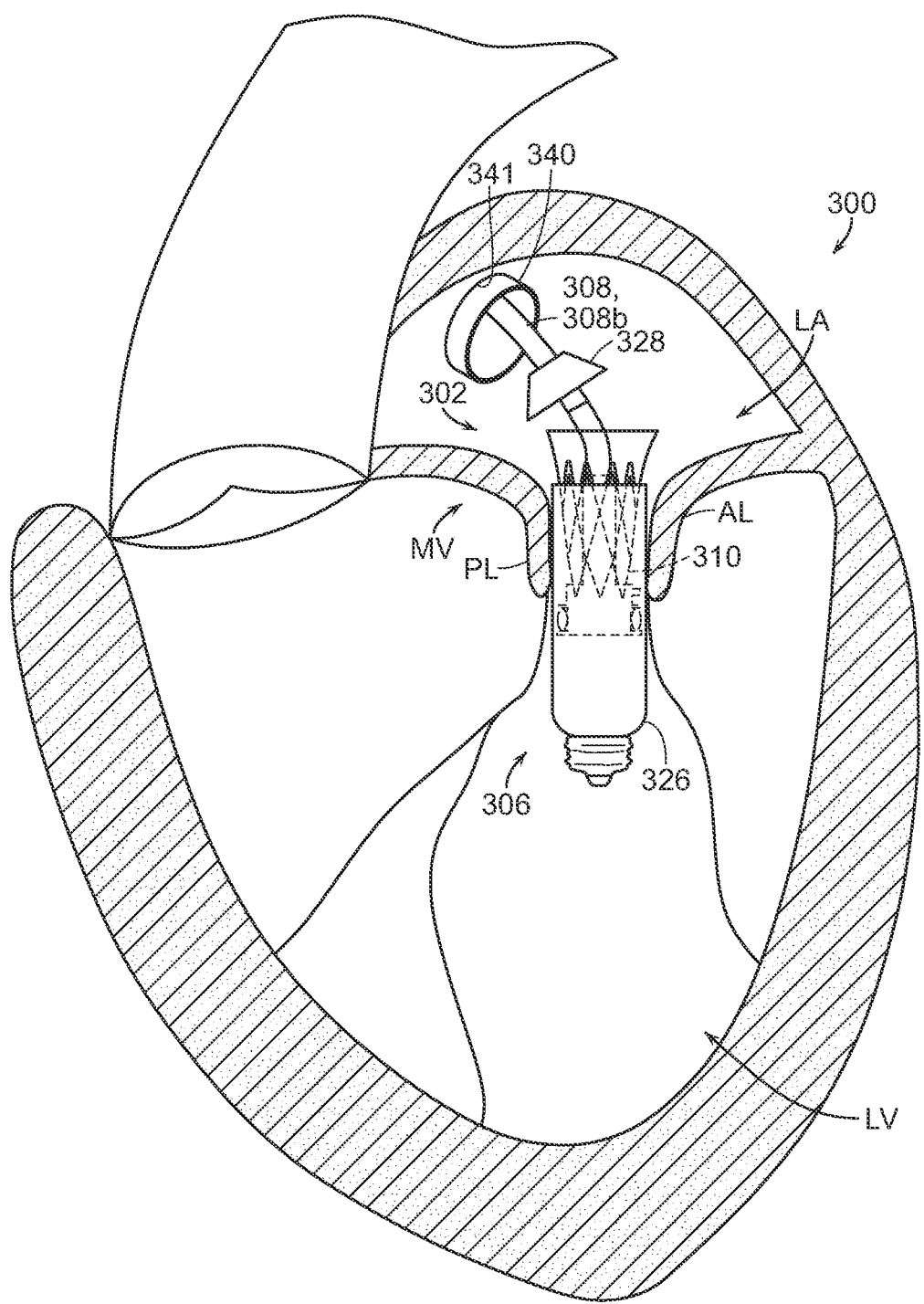
Figure 10C:
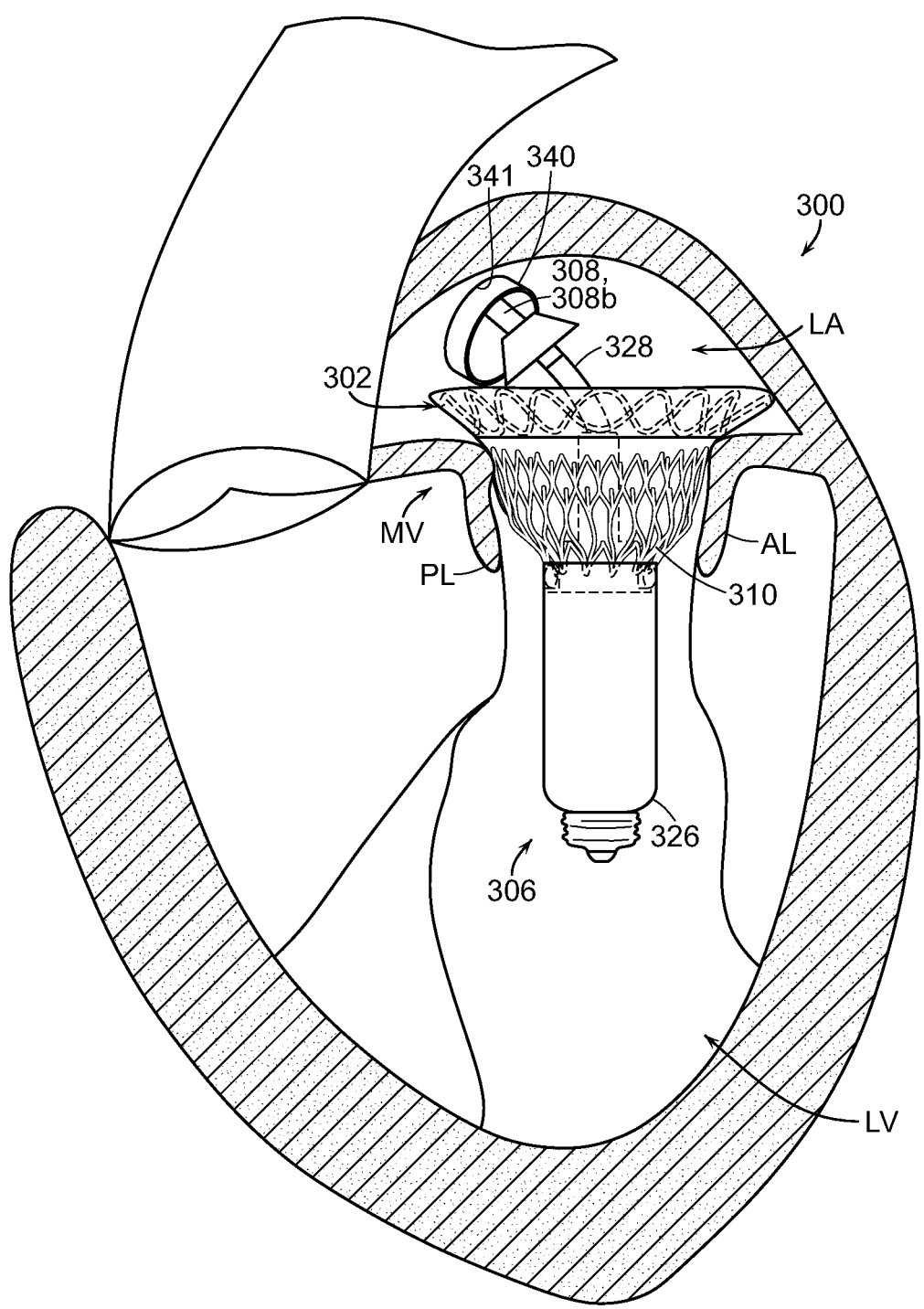

FIGS. 10A-10C are a series of partially schematic illustrations of a distal portion of a hydraulic delivery system 300 deploying a prosthetic a prosthetic heart valve device 310 within a native mitral valve of a heart using a trans-septal approach in accordance with further embodiments of the present technology. The hydraulic delivery system 300 can include certain features generally similar the delivery systems 100, 200 described above with reference to FIGS. 6-9C. For example, the delivery system 300 includes a catheter 302 having an elongated catheter body 308 and a delivery capsule 306 at a distal portion 308b of the catheter body 308. The proximal portion of the catheter 302 can be coupled to a fluid system (e.g., the fluid assembly 112 of FIG. 6) and/or a manifold (e.g., the manifold 158 of FIGS. 8A and 8B) to hydraulically move the delivery capsule 306 between a containment configuration and a deployment configuration. The delivery system 300 facilitates trans-septal delivery of the prosthetic heart valve device 310 to the native mitral valve MV.

Referring to FIG. 10A, a puncture or opening 341 can be formed in an atrial region of a septum of the heart to access the left atrium LA. A guide catheter 340 can be positioned through the opening 341, and a guidewire 320 can extend through the guide catheter 340, through the mitral valve MV, and into the left ventricle LV. A delivery capsule 306 at a distal portion 308b of the elongated catheter body 308 can then be delivered to the left atrium LA from the guide catheter 340, advanced along the guidewire 320, and positioned at a target site between the posterior and anterior leaflets PL and AL of the mitral valve MV.

As shown in FIG. 10B, once at the target site in the mitral valve MV, the prosthetic heart valve device 310 can be deployed by removing a proximally positioned end cap 328 and moving a housing 326 of the delivery capsule 306 in a distal direction (i.e., downstream further into the left ventricle LV). In certain embodiments, fluid can be delivered and removed to/from chambers (not shown) of the delivery capsule 306 to hydraulically move the housing 326 toward the deployment configuration. This distal movement unsheathes the upstream or inflow portion of the prosthetic heart valve device 310 while the downstream or ventricular end of the prosthetic heart valve device 310 remains constrained within the housing 326. The unsheathed inflow portion can expand outward to contact tissue of the mitral valve MV. If the clinician elects to adjust the positioning of the prosthetic heart valve device 310, fluid can be delivered to and removed from the delivery capsule chambers in an opposite manner to hydraulically move the housing 326 toward the containment configuration and at least partially resheathe the prosthetic heart valve device 310. After the deployed inflow portion of the prosthetic heart valve device 310 is appropriately seated in the mitral valve MV, fluid can again be delivered to and removed from the delivery capsule chambers to again move the housing 326 distally toward the deployment configuration. As shown in FIG. 10C, fluid can be delivered/removed until the housing 326 fully unsheathes the prosthetic heart valve device 310 and the prosthetic heart valve device 310 expands against the mitral valve MV. In the fully deployed state, the delivery capsule 306 can then be returned to the containment configuration (e.g., with the housing 326 and the end cap 328 joined together), pulled through the left atrium LA, and removed from the heart.

In other embodiments, the system 100 of FIGS. 6-8B can be reconfigured to allow for deployment from the left atrium (e.g., via the trans-septal approach shown in FIGS. 10A-10C) in which case the housing 126 with the first and second chambers 144a and 144b has the opposite orientation shown in FIGS. 8A and 8B. That is, the end cap 128 is positioned adjacent to the distal portion 108b of the catheter body 108 and the housing 126 is located distally from the end cap 128 with the shaft 148 extending through or adjacent to the device 110 to allow fluid delivery to the chambers 144. To deploy the prosthetic heart valve device 110, fluid is removed from the first fluid chamber 144a while fluid is delivered to the second fluid chamber 144b, which moves the housing 126 distally (further into the left ventricle) to at least partially unsheathe the prosthetic heart valve device 110. To resheathe the prosthetic heart valve device 110, fluid is removed from the second fluid chamber 144b while fluid is delivered to the first fluid chamber 144a, moving the housing 126 proximally (toward the catheter body 108) toward the containment configuration.

FIGS. 11A and 11B are enlarged, partially schematic cross-sectional views of a distal portion of the trans-septal delivery system 300 in a partially expanded deployment configuration (FIG. 11A) and a resheathing or containment configuration (FIG. 11B) in accordance with an embodiment of the present technology. As discussed above, the delivery system 300 includes the delivery capsule 306 coupled to the distal portion 308b of the catheter body 308. The delivery capsule 306 includes the housing 326 and a platform 342 that define, at least in part, a first or deployment chamber 344a. The delivery system 300 further includes expandable member 390 coupled to the catheter body 308 and distal to the delivery capsule 306. The interior of the expandable member 390 defines a second or resheathing chamber 344b. The expandable member 390 can be a balloon or other expandable component in which a fluid can be contained and removed. The delivery system 300 can also include sealing features 356 (identified individually as a first sealing features 356a and a second sealing feature 356b), such as O-rings, to fluidically seal the deployment chamber 344a from a containment compartment 346 (FIG. 11B) in the housing 326 that carries the prosthetic heart valve device 310 and the expandable member 390. In other embodiments, the delivery system 300 can include additional sealing features for fluidically sealing the deployment chamber 344a and the resheathing chamber 344b.

As further shown in FIGS. 11A and 11B, a fluid delivery shaft 348 extends through the housing 326 and into the expandable member 390. The fluid delivery shaft 348 includes at least a first fluid line 352a in fluid communication with the deployment chamber 344a via a first opening 366a and a second fluid line 352b in fluid communication with the resheathing chamber 344b via a second opening 366b. The proximal portions of the fluid lines 352 can be in fluid communication with a manifold (not shown; e.g., the manifold 158 of FIGS. 8A and 8B) and/or a fluid system (not shown; e.g., the fluid assembly 112 of FIG. 6) to allow fluid to be delivered to and removed from the deployment and resheathing chambers 344a and 344b. In other embodiments, the first fluid line 352a and the second fluid line 352b can be separate components, such as two fluid delivery/removal shafts, one in fluid communication with the deployment chamber 344a and one in fluid communication with the resheathing chamber 344b. The fluid delivery shaft 348 can extend through the catheter body 308, adjacent to the catheter body 308. In other embodiments, the fluid delivery shaft 348 is omitted and the fluid lines 352 can be separate components that extend through the catheter body 308.

In various embodiments, the delivery system 300 can further include a distal end cap 392 positioned distal to the expandable member 390 and coupled to the distal portion 308b of the catheter body 308 and/or the fluid delivery shaft 348. The distal end cap 392 can be configured to seal the distal end of the expandable member 390 and/or may have an atraumatic shape (e.g., frusto-conical, partially spherical, etc.) to facilitate atraumatic delivery of the delivery capsule 306 to the target site. As shown in FIGS. 11A and 11B, the distal end cap 392 can also include an opening 330 that allows for guidewire delivery of the delivery capsule 306 to the target site.

The delivery capsule 306 can be hydraulically driven between a containment configuration in which the prosthetic heart valve device 310 is held in the compartment 346 of the housing 326 and the deployment configuration in which at least a portion of the prosthetic heart valve device 310 expands from the compartment 346. More specifically, in an initial containment state (e.g., as the delivery capsule 306 is delivered to the target site), the prosthetic heart valve device 310 is held in the compartment 346 of the housing 326 and the expandable member 390 is at least substantially empty (e.g., the configuration of the expandable member 390 shown in FIG. 11A). To begin deployment, fluid is delivered to the deployment chamber 344a via the first line 352a (e.g., as indicated by arrows 391 in FIG. 11A). Providing fluid to the deployment chamber 344a increases the pressure therein, thereby moving the housing 326 distally relative to the platform 342 and unsheathing the prosthetic heart valve device 310 (beginning with the atrial or inflow portion of the device 310). This unsheathing mechanism at least substantially prevents translation of the prosthetic heart valve device 310 relative to the catheter body 308 and the surrounding anatomy to facilitate positioning and deployment of the device 310.

As shown in FIG. 11B, the prosthetic heart valve device 310 can be at least partially resheathed after at least partial deployment. To resheathe the device 310, fluid is drained or removed from deployment chamber 344a (as indicated by arrows 393), while fluid is delivered to the expandable member 390 via the second line 352b (as indicated by arrows 395). The expansion of the expandable member 390 urges the housing 326 towards the containment configuration such that the prosthetic heart valve device 310 is at least partially resheathed and again positioned at least partially in the compartment 346 of the housing 326 (FIG. 11B). Accordingly, the delivery system 300 provides for controlled, hydraulic delivery of the prosthetic heart valve device 310 via a trans-septal delivery approach and also inhibits translation of the prosthetic heart valve device 310 during deployment and resheathing to facilitate accurate delivery to the target site.

Selected Embodiments of Prosthetic Heart Valve Devices

The hydraulic delivery systems 100, 200, 300 described above with reference to FIGS. 6-11B can be configured to deliver various prosthetic heart valve devices, such as prosthetic valve devices for replacement of the mitral valve and/or other valves (e.g., a bicuspid or tricuspid valve) in the heart of the patient. Examples of these prosthetic heart valve devices, system components, and associated methods are described in this section with reference to FIGS. 12A-25. Specific elements, substructures, advantages, uses, and/or other features of the embodiments described with reference to FIGS. 12A-25 can be suitably interchanged, substituted or otherwise configured with one another. Furthermore, suitable elements of the embodiments described with reference to FIGS. 12A-25 can be used as stand-alone and/or self-contained devices.

Figure 12A:
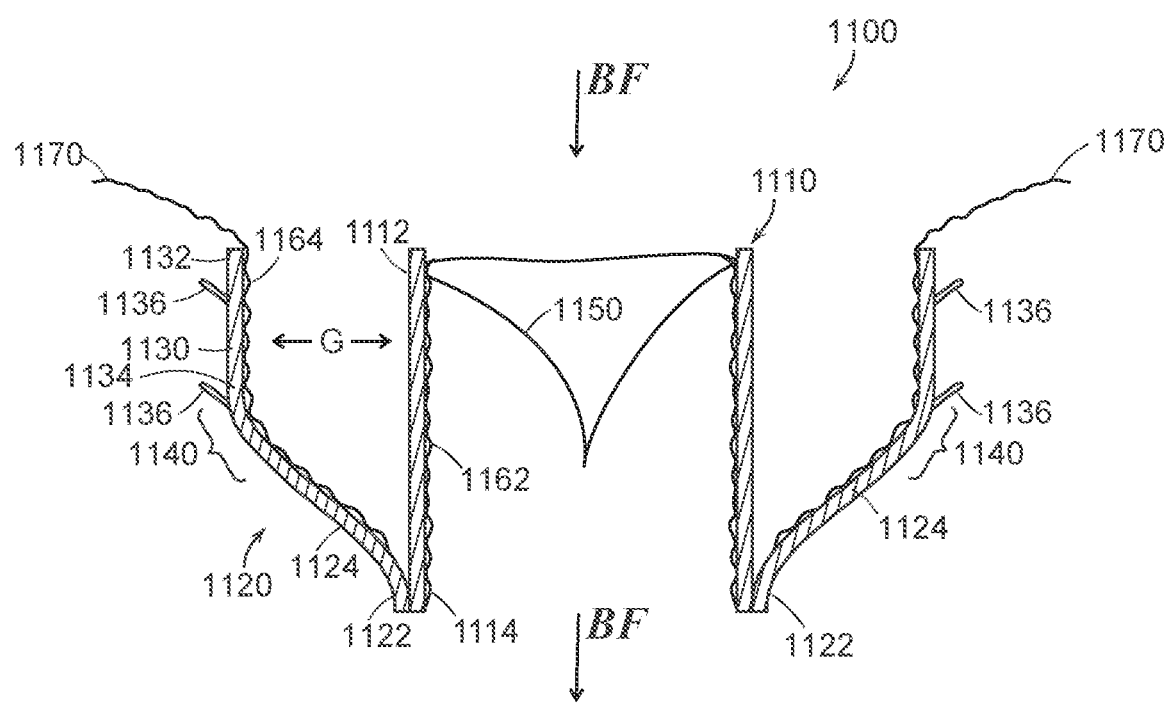
FIG. 12A is a cross-sectional side view and FIG. 12B is a top view schematically illustrating a prosthetic heart valve device in accordance with an embodiment of the present technology.
Figure 12B:
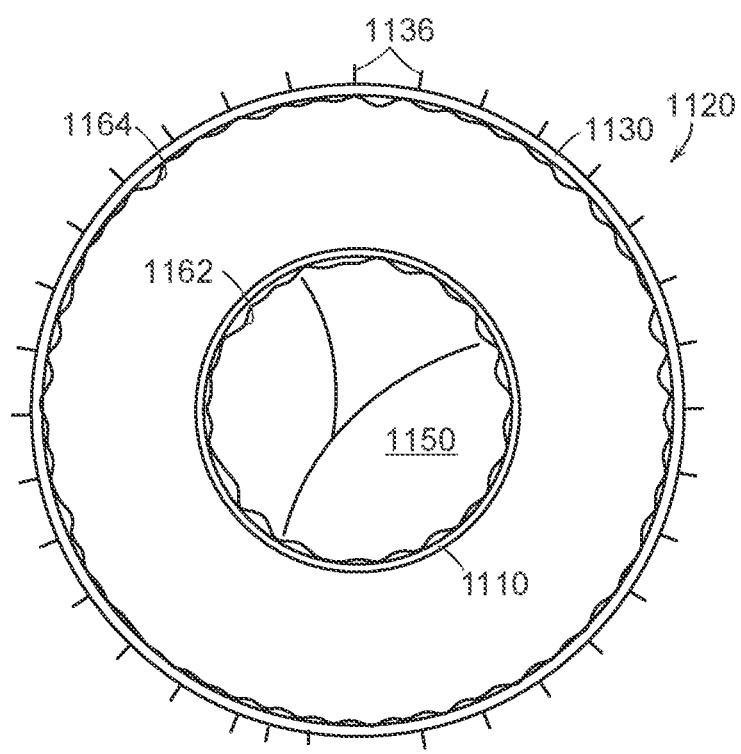

FIG. 12A is a side cross-sectional view and FIG. 12B is a top plan view of a prosthetic heart valve device ("device") 1100 in accordance with an embodiment of the present technology. The device 1100 includes a valve support 1110, an anchoring member 1120 attached to the valve support 1110, and a prosthetic valve assembly 1150 within the valve support 1110. Referring to FIG. 12A, the valve support 1110 has an inflow region 1112 and an outflow region 1114. The prosthetic valve assembly 1150 is arranged within the valve support 1110 to allow blood to flow from the inflow region 1112 through the outflow region 1114 (arrows BF), but prevent blood from flowing in a direction from the outflow region 1114 through the inflow region 1112.

In the embodiment shown in FIG. 12A, the anchoring member 1120 includes a base 1122 attached to the outflow region 1114 of the valve support 1110 and a plurality of arms 1124 projecting laterally outward from the base 1122. The anchoring member 1120 also includes a fixation structure 1130 extending from the arms 1124. The fixation structure 1130 can include a first portion 1132 and a second portion 1134. The first portion 1132 of the fixation structure 1130, for example, can be an upstream region of the fixation structure 1130 that, in a deployed configuration as shown in FIG. 12A, is spaced laterally outward apart from the inflow region 1112 of the valve support 1110 by a gap G. The second portion 1134 of the fixation structure 1130 can be a downstream-most portion of the fixation structure 1130. The fixation structure 1130 can be a cylindrical ring (e.g., straight cylinder or conical), and the outer surface of the fixation structure 1130 can define an annular engagement surface configured to press outwardly against a native annulus of a heart valve (e.g., a mitral valve). The fixation structure 1130 can further include a plurality of fixation elements 1136 that project radially outward and are inclined toward an upstream direction. The fixation elements 1136, for example, can be barbs, hooks, or other elements that are inclined only in the upstream direction (e.g., a direction extending away from the downstream portion of the device 1100).

Referring still to FIG. 12A, the anchoring member 1120 has a smooth bend 1140 between the arms 1124 and the fixation structure 1130. For example, the second portion 1134 of the fixation structure 1130 extends from the arms 1124 at the smooth bend 1140. The arms 1124 and the fixation structure 1130 can be formed integrally from a continuous strut or support element such that the smooth bend 1140 is a bent portion of the continuous strut. In other embodiments, the smooth bend 1140 can be a separate component with respect to either the arms 1124 or the fixation structure 1130. For example, the smooth bend 1140 can be attached to the arms 1124 and/or the fixation structure 1130 using a weld, adhesive or other technique that forms a smooth connection. The smooth bend 1140 is configured such that the device 1100 can be recaptured in a capsule or other container after the device 1100 has been at least partially deployed.

The device 1100 can further include a first sealing member 1162 on the valve support 1110 and a second sealing member 1164 on the anchoring member 1120. The first and second sealing members 1162, 1164 can be made from a flexible material, such as Dacron® or another type of polymeric material. The first sealing member 1162 can cover the interior and/or exterior surfaces of the valve support 1110. In the embodiment illustrated in FIG. 12A, the first sealing member 1162 is attached to the interior surface of the valve support 1110, and the prosthetic valve assembly 1150 is attached to the first sealing member 1162 and commissure portions of the valve support 1110. The second sealing member 1164 is attached to the inner surface of the anchoring member 1120. As a result, the outer annular engagement surface of the fixation structure 1130 is not covered by the second sealing member 1164 so that the outer annular engagement surface of the fixation structure 1130 directly contacts the tissue of the native annulus.

The device 1100 can further include an extension member 1170. The extension member 1170 can be an extension of the second sealing member 1164, or it can be a separate component attached to the second sealing member 1164 and/or the first portion 1132 of the fixation structure 1130. The extension member 1170 can be a flexible member that, in a deployed state (FIG. 12A), flexes relative to the first portion 1132 of the fixation structure 1130. In operation, the extension member 1170 provides tactile feedback or a visual indicator (e.g., on echocardiographic or fluoroscopic imaging systems) to guide the device 1100 during implantation such that the device 1100 is located at a desired elevation and centered relative to the native annulus. As described below, the extension member 1170 can include a support member, such as a metal wire or other structure, that can be visualized via fluoroscopy or other imaging techniques during implantation. For example, the support member can be a radiopaque wire.

Figure 13A:
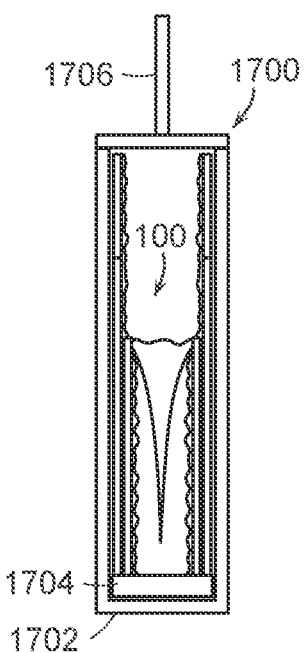
FIGS. 13A and 13B are cross-sectional side views schematically illustrating aspects of delivering a prosthetic heart valve device in accordance with an embodiment of the present technology.
Figure 13B:
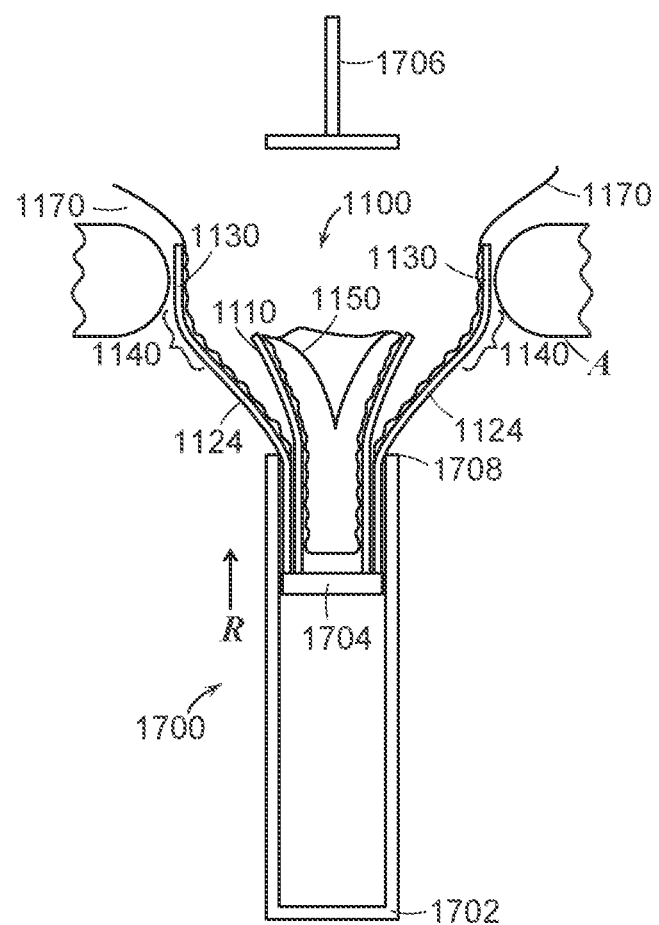

FIGS. 13A and 13B are cross-sectional views illustrating an example of the operation of the smooth bend 1140 between the arms 1124 and the fixation structure 1130 in the recapturing of the device 1100 after partial deployment. FIG. 13A schematically shows the device 1100 loaded into a capsule 1700 of a delivery system in a delivery state, and FIG. 13B schematically shows the device 1100 in a partially deployed state. Referring to FIG. 13A, the capsule 1700 has a housing 1702, a pedestal or support 1704, and a top 1706. In the delivery state shown in FIG. 13A, the device 1100 is in a low-profile configuration suitable for delivery through a catheter or cannula to a target implant site at a native heart valve.

Referring to FIG. 13B, the housing 1702 of the capsule 1700 has been moved distally such that the extension member 1170, fixation structure 1130 and a portion of the arms 1124 have been released from the housing 1702 in a partially deployed state. This is useful for locating the fixation structure 1130 at the proper elevation relative to the native valve annulus A such that the fixation structure 1130 expands radially outward into contact the inner surface of the native annulus A. However, the device 1100 may need to be repositioned and/or removed from the patient after being partially deployed. To do this, the housing 1702 is retracted (arrow R) back toward the fixation structure 1130. As the housing 1702 slides along the arms 1124, the smooth bend 1140 between the arms 1124 and the fixation structure 1130 allows the edge 1708 of the housing 1702 to slide over the smooth bend 1140 and thereby recapture the fixation structure 1130 and the extension member 1170 within the housing 1702. The device 1100 can then be removed from the patient or repositioned for redeployment at a better location relative to the native annulus A. Further aspects of prosthetic heart valve devices in accordance with the present technology and their interaction with corresponding delivery devices are described below with reference to FIGS. 14-25.

Figure 14:
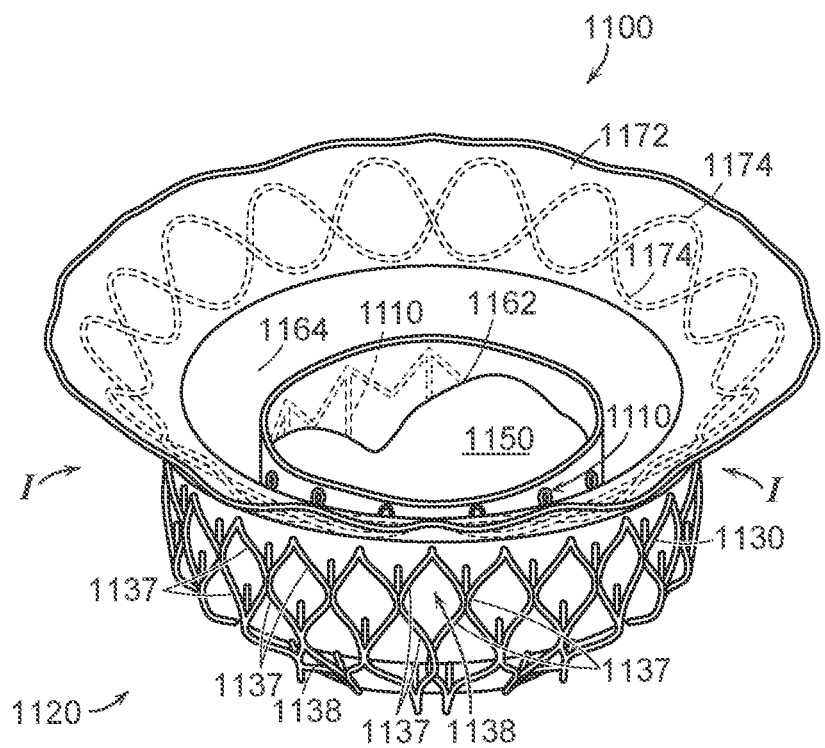
FIG. 14 is a top isometric view of a prosthetic heart valve device in accordance with an embodiment of the present technology.

FIG. 14 is a top isometric view of an example of the device 1100. In this embodiment, the valve support 1110 defines a first frame (e.g., an inner frame) and fixation structure 1130 of the anchoring member 1120 defines a second frame (e.g., an outer frame) that each include a plurality of structural elements. The fixation structure 1130, more specifically, includes structural elements 1137 arranged in diamond-shaped cells 1138 that together form at least a substantially cylindrical ring when freely and fully expanded as shown in FIG. 14. The structural elements 1137 can be struts or other structural features formed from metal, polymers, or other suitable materials that can self-expand or be expanded by a balloon or other type of mechanical expander.

In several embodiments, the fixation structure 1130 can be a generally cylindrical fixation ring having an outwardly facing engagement surface. For example, in the embodiment shown in FIG. 14, the outer surfaces of the structural elements 1137 define an annular engagement surface configured to press outwardly against the native annulus in the deployed state. In a fully expanded state without any restrictions, the walls of the fixation structure 1130 are at least substantially parallel to those of the valve support 1110. However, the fixation structure 1130 can flex inwardly (arrow I) in the deployed state when it presses radially outwardly against the inner surface of the native annulus of a heart valve.

The embodiment of the device 1100 shown in FIG. 14 includes the first sealing member 1162 lining the interior surface of the valve support 1110, and the second sealing member 1164 along the inner surface of the fixation structure 1130. The extension member 1170 has a flexible web 1172 (e.g., a fabric) and a support member 1174 (e.g., metal or polymeric strands) attached to the flexible web 1172. The flexible web 1172 can extend from the second sealing member 1164 without a metal-to-metal connection between the fixation structure 1130 and the support member 1174. For example, the extension member 1170 can be a continuation of the material of the second sealing member 1164. Several embodiments of the extension member 1170 are thus a malleable or floppy structure that can readily flex with respect to the fixation structure 1130. The support member 1174 can have a variety of configurations and be made from a variety of materials, such as a double-serpentine structure made from Nitinol.

Figure 15:
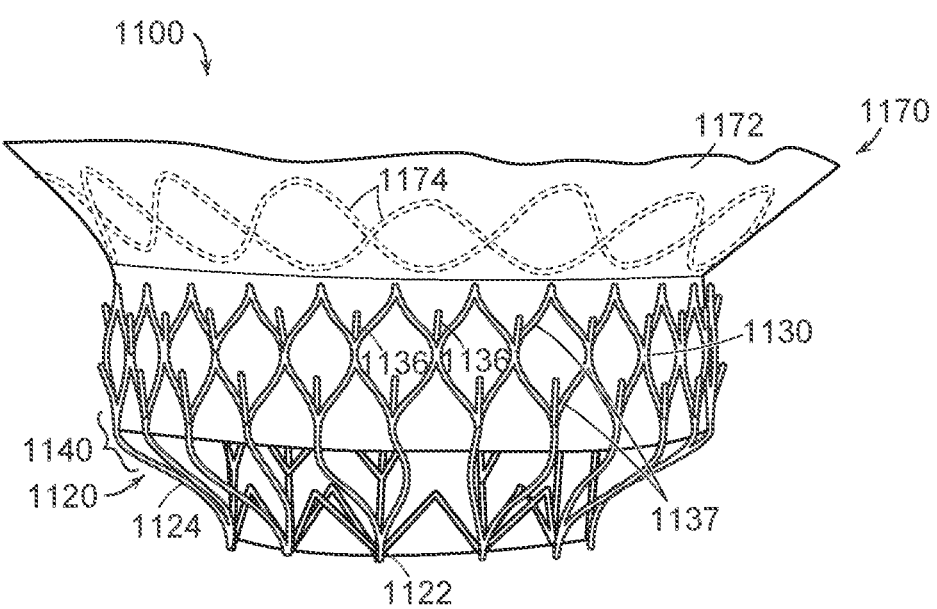
FIG. 15 is a side view and FIG. 16 is a bottom isometric view of the prosthetic heart valve device of FIG. 14.
Figure 16:
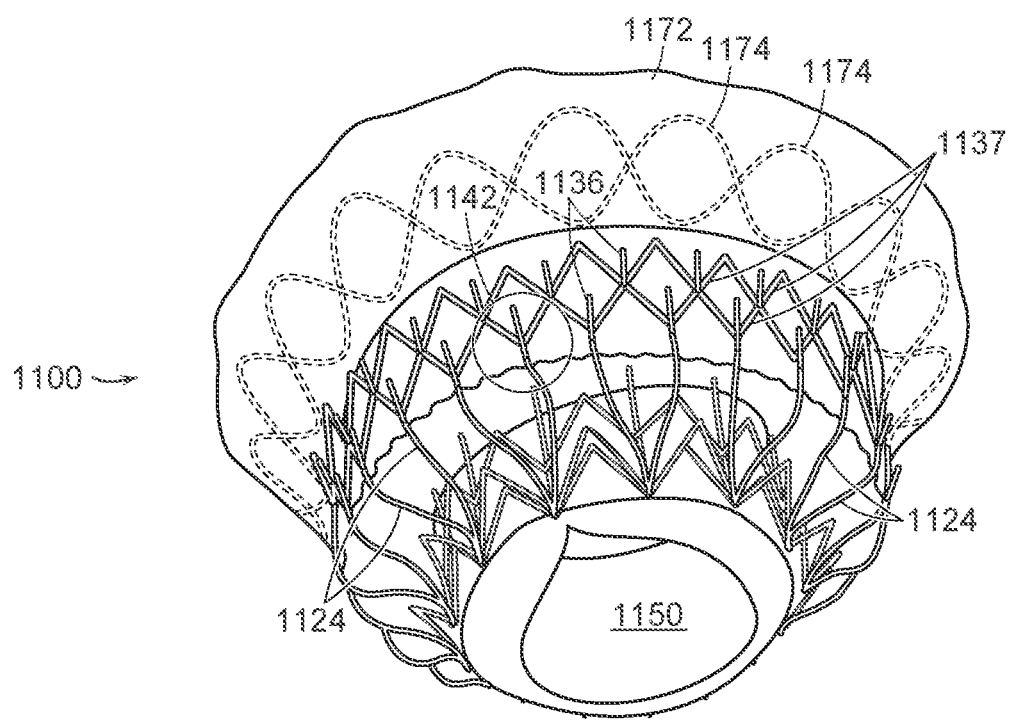

FIG. 15 is a side view and FIG. 16 is a bottom isometric view of the device 1100 shown in FIG. 14. Referring to FIG. 15, the arms 1124 extend radially outward from the base portion 1122 at an angle α selected to position the fixation structure 1130 radially outward from the valve support 1110 (FIG. 14) by a desired distance in a deployed state. The angle α is also selected to allow the edge 1708 of the delivery system housing 1702 (FIG. 13B) to slide from the base portion 1122 toward the fixation structure 1130 during recapture. In many embodiments, the angle α is 15°-75°, or more specifically 15°-60°, or still more specifically 30°-45°. The arms 1124 and the structural elements 1137 of the fixation structure 1130 can be formed from the same struts (i.e., formed integrally with each other) such that the smooth bend 1140 is a continuous, smooth transition from the arms 1124 to the structural elements 1137. This is expected to enable the edge 1708 of the housing 1702 to more readily slide over the smooth bend 1140 in a manner that allows the fixation structure 1130 to be recaptured in the housing 1702 of the capsule 1700 (FIG. 13B). Additionally, by integrally forming the arms 1124 and the structural elements 1137 with each other, it inhibits damage to the device 1100 at a junction between the arms 1124 and the structural elements 1137 compared to a configuration in which the arms 1124 and structural elements 1137 are separate components and welded or otherwise fastened to each other.

Referring to FIGS. 15 and 16, the arms 1124 are also separated from each other along their entire length from where they are connected to the base portion 1122 through the smooth bend 1140 (FIG. 15) to the structural elements 1137 of the fixation structure 1130. The individual arms 1124 are thus able to readily flex as the edge 1708 of the housing 1702 (FIG. 13B) slides along the arms 1124 during recapture. This is expected to reduce the likelihood that the edge 1708 of the housing 1702 will catch on the arms 1124 and prevent the device 1100 from being recaptured in the housing 1702.

In one embodiment, the arms 1124 have a first length from the base 1122 to the smooth bend 1140, and the structural elements 1137 of the fixation structure 1130 at each side of a cell 1138 (FIG. 14) have a second length that is less than the first length of the arms 1124. The fixation structure 1130 is accordingly less flexible than the arms 1124. As a result, the fixation structure 1130 is able to press outwardly against the native annulus with sufficient force to secure the device 1100 to the native annulus, while the arms 1124 are sufficiently flexible to fold inwardly when the device is recaptured in a delivery device.

In the embodiment illustrated in FIGS. 14-16, the arms 1124 and the structural elements 1137 are configured such that each arm 1124 and the two structural elements 1137 extending from each arm 1124 formed a Y-shaped portion 1142 (FIG. 16) of the anchoring member 1120. Additionally, the right-hand structural element 1137 of each Y-shaped portion 1142 is coupled directly to a left-hand structural element 1137 of an immediately adjacent Y-shaped portion 1142. The Y-shaped portions 1142 and the smooth bends 1140 are expected to further enhance the ability to slide the housing 1702 along the arms 1124 and the fixation structure 1130 during recapture.

Figure 17:
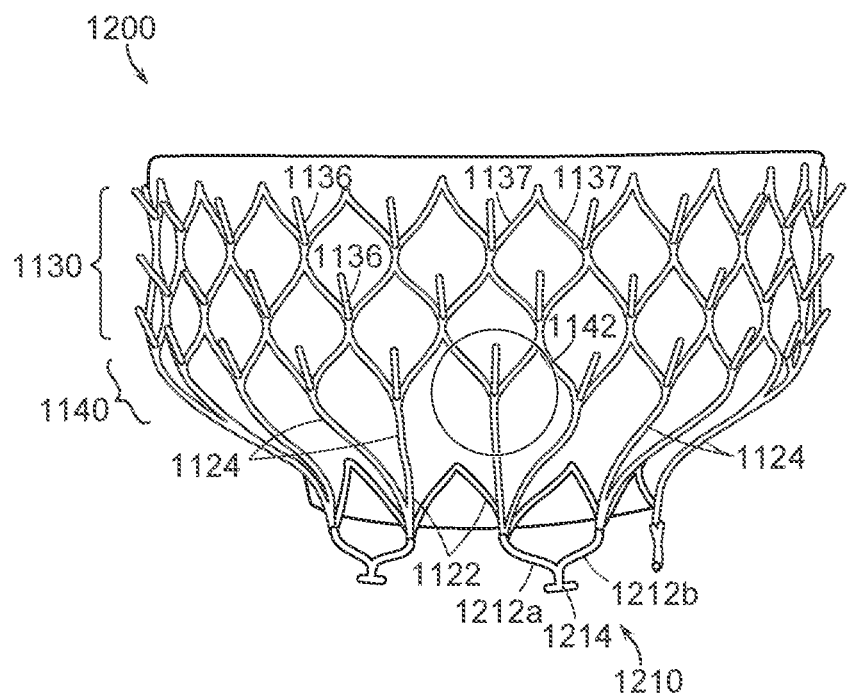
FIG. 17 is a side view and FIG. 18 is a bottom isometric view of a prosthetic heart valve device in accordance with an embodiment of the present technology.
Figure 18:
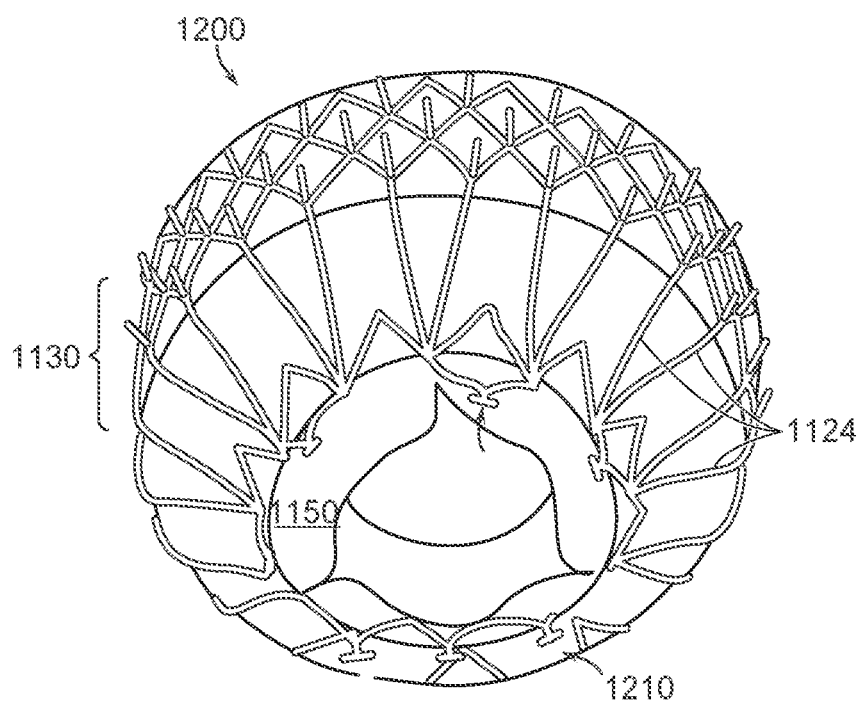

FIG. 17 is a side view and FIG. 18 is a bottom isometric view of a prosthetic heart valve device ("device") 1200 in accordance with another embodiment of the present technology. The device 1200 is shown without the extension member 1170 (FIGS. 14-16), but the device 1200 can further include the extension member 1170 described above. The device 1200 further includes extended connectors 1210 projecting from the base 1122 of the anchoring member 1120. Alternatively, the extended connectors 1210 can extend from the valve support 1110 (FIGS. 12A-16) in addition to or in lieu of extending from the base 1122 of the anchoring member 1120. The extended connectors 1210 can include a first strut 1212a attached to one portion of the base 1122 and a second strut 1212b attached to another portion of the base 1122. The first and second struts 1212a-b are configured to form a V-shaped structure in which they extend toward each other in a downstream direction and are connected to each other at the bottom of the V-shaped structure. The V-shaped structure of the first and second struts 1212a-b causes the extension connector 1210 to elongate when the device 1200 is in a low-profile configuration within the capsule 1700 (FIG. 13A) during delivery or partial deployment. When the device 1200 is fully released from the capsule 1700 (FIG. 13A) the extension connectors 1210 foreshorten to avoid interfering with blood flow along the left ventricular outflow tract.

The extended connectors 1210 further include an attachment element 1214 configured to releasably engage a delivery device. The attachment element 1214 can be a T-bar or other element that prevents the device 1200 from being released from the capsule 1700 (FIG. 13A) of a delivery device until desired. For example, a T-bar type attachment element 1214 can prevent the device 1200 from moving axially during deployment or partial deployment until the housing 1702 (FIG. 13A) moves beyond the portion of the delivery device engaged with the attachment elements 1214. This causes the attachment elements 1214 to disengage from the capsule 1700 (FIG. 13A) as the outflow region of the valve support 1110 and the base 1122 of the anchoring member 1120 fully expand to allow for full deployment of the device 1200.

Figure 19:
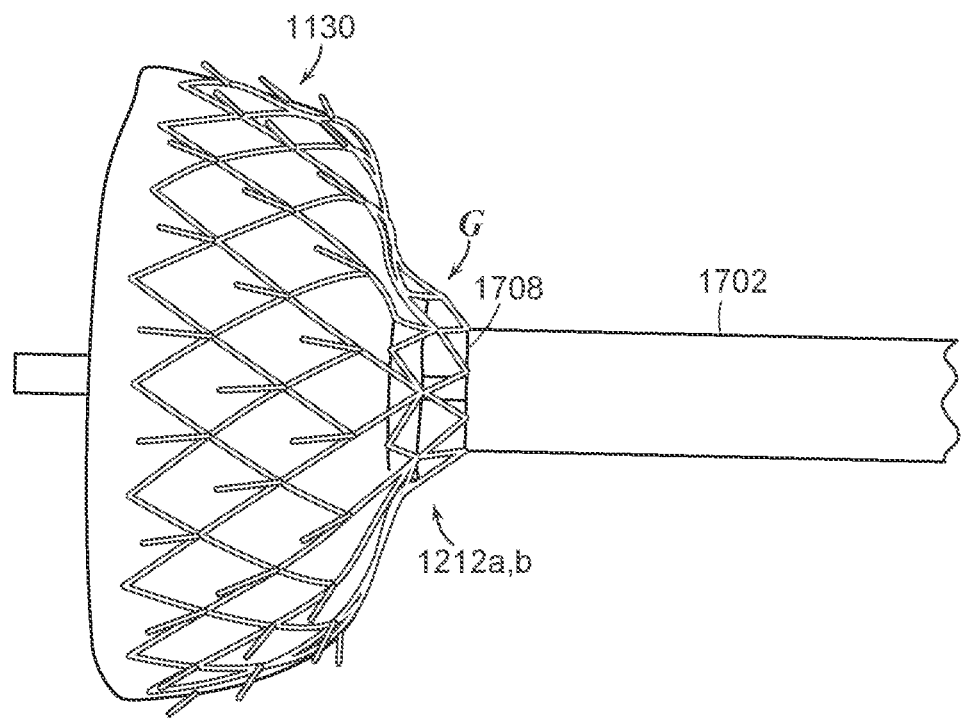
FIG. 19 is a side view and FIG. 20 is a bottom isometric view of the prosthetic heart valve device of FIGS. 17 and 18 at a partially deployed state with respect to a delivery device.
Figure 20:
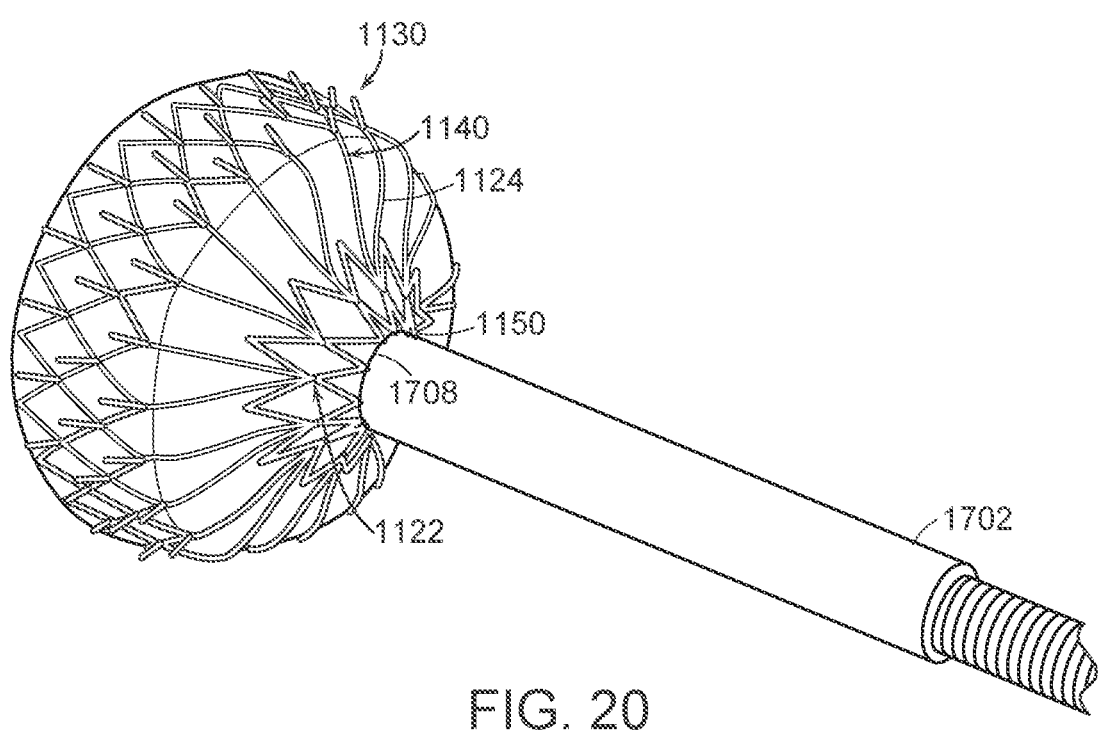

FIG. 19 is a side view and FIG. 20 is a bottom isometric view of the device 1200 in a partially deployed state in which the device 1200 is still capable of being recaptured in the housing 1702 of the delivery device 1700. Referring to FIG. 19, the device 1200 is partially deployed with the fixation structure 1130 substantially expanded but the attachment elements 1214 (FIG. 17) still retained within the capsule 1700. This is useful for determining the accuracy of the position of the device 1200 and allowing blood to flow through the functioning replacement valve during implantation while retaining the ability to recapture the device 1200 in case it needs to be repositioned or removed from the patient. In this state of partial deployment, the elongated first and second struts 1212a-b of the extended connectors 1210 space the base 1122 of the anchoring member 1120 and the outflow region of the valve support 1110 (FIG. 12A) apart from the edge 1708 of the capsule 1700 by a gap G.

Referring to FIG. 20, the gap G enables blood to flow through the prosthetic valve assembly 1150 while the device 1200 is only partially deployed. As a result, the device 1200 can be partially deployed to determine (a) whether the device 1200 is positioned correctly with respect to the native heart valve anatomy and (b) whether proper blood flow passes through the prosthetic valve assembly 1150 while the device 1200 is still retained by the delivery system 1700. As such, the device 1200 can be recaptured if it is not in the desired location and/or if the prosthetic valve is not functioning properly. This additional functionality is expected to significantly enhance the ability to properly position the device 1200 and assess, in vivo, whether the device 1200 will operate as intended, while retaining the ability to reposition the device 1200 for redeployment or remove the device 1200 from the patient.

Figure 21:
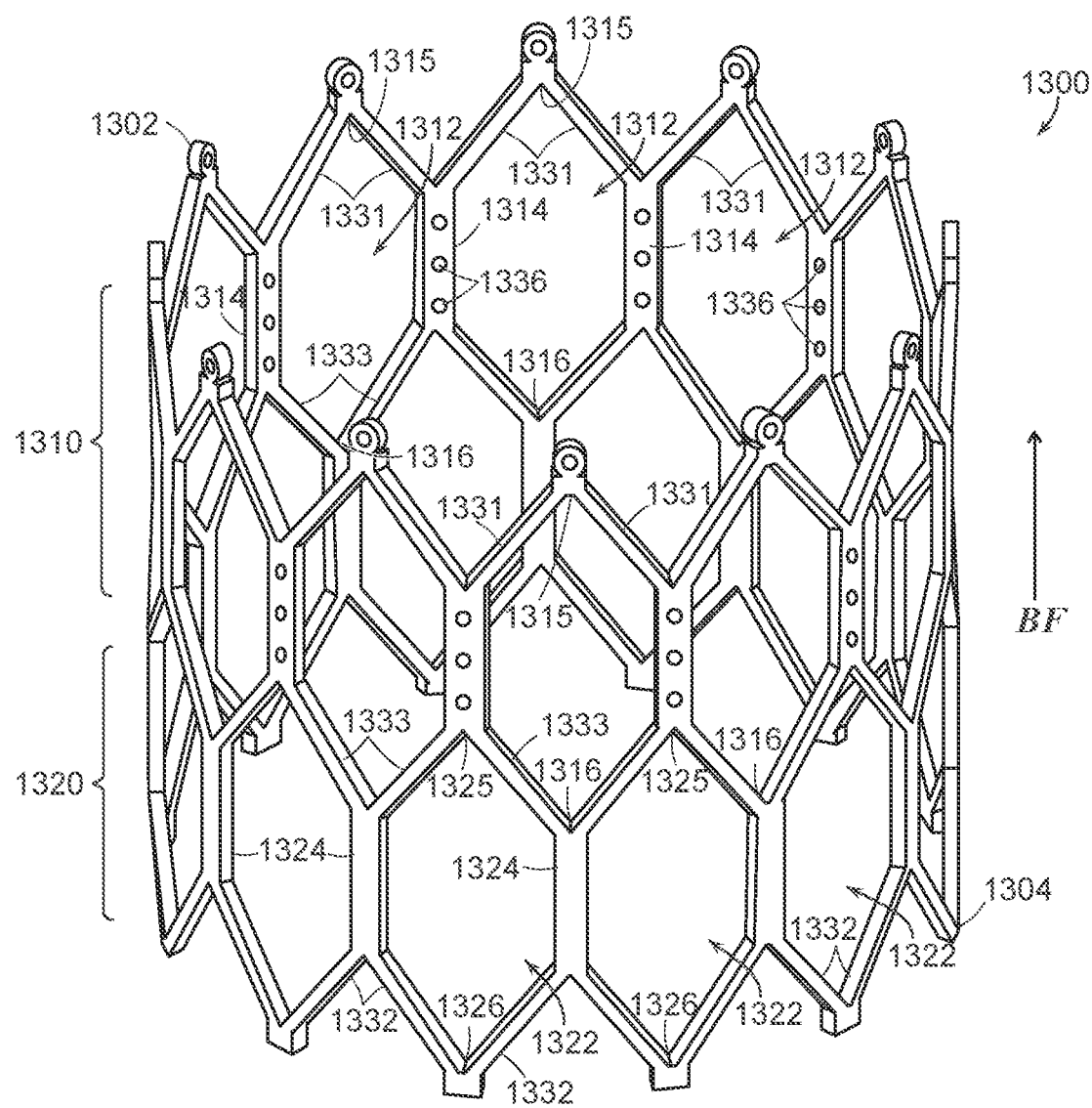
FIG. 21 is an isometric view of a valve support for use with prosthetic heart valve devices in accordance with the present technology.

FIG. 21 is an isometric view of a valve support 1300 in accordance with an embodiment of the present technology. The valve support 1300 can be an embodiment of the valve support 1110 described above with respect to FIGS. 12A-20. The valve support 1300 has an outflow region 1302, an inflow region 1304, a first row 1310 of first hexagonal cells 1312 at the outflow region 1302, and a second row 1320 of second hexagonal cells 1322 at the inflow region 1304. For purposes of illustration, the valve support shown in FIG. 21 is inverted compared to the valve support 1110 shown in FIGS. 12A-20 such that the blood flows through the valve support 1300 in the direction of arrow BF. In mitral valve applications, the valve support 1300 would be positioned within the anchoring member 1120 (FIG. 12A) such that the inflow region 1304 would correspond to orientation of the inflow region 1112 in FIG. 12A and the outflow region 1302 would correspond to the orientation of the outflow region 1114 in FIG. 12A.

Each of the first hexagonal cells 1312 includes a pair of first longitudinal supports 1314, a downstream apex 1315, and an upstream apex 1316. Each of the second hexagonal cells 1322 can include a pair of second longitudinal supports 1324, a downstream apex 1325, and an upstream apex 1326. The first and second rows 1310 and 1312 of the first and second hexagonal cells 1312 and 1322 are directly adjacent to each other. In the illustrated embodiment, the first longitudinal supports 1314 extend directly from the downstream apexes 1325 of the second hexagonal cells 1322, and the second longitudinal supports 1324 extend directly from the upstream apexes 1316 of the first hexagonal cells 1312. As a result, the first hexagonal cells 1312 are offset from the second hexagonal cells 1322 around the circumference of the valve support 1300 by half of the cell width.

In the embodiment illustrated in FIG. 21, the valve support 1300 includes a plurality of first struts 1331 at the outflow region 1302, a plurality of second struts 1332 at the inflow region 1304, and a plurality of third struts 1333 between the first and second struts 1331 and 1332. Each of the first struts 1331 extends from a downstream end of the first longitudinal supports 1314, and pairs of the first struts 1331 are connected together to form first downstream V-struts defining the downstream apexes 1315 of the first hexagonal cells 1312. In a related sense, each of the second struts 1332 extends from an upstream end of the second longitudinal supports 1324, and pairs of the second struts 1332 are connected together to form second upstream V-struts defining the upstream apexes 1326 of the second hexagonal cells 1322. Each of the third struts 1333 has a downstream end connected to an upstream end of the first longitudinal supports 1314, and each of the third struts 1333 has an upstream end connected to a downstream end of one of the second longitudinal supports 1324. The downstream ends of the third struts 1333 accordingly define a second downstream V-strut arrangement that forms the downstream apexes 1325 of the second hexagonal cells 1322, and the upstream ends of the third struts 1333 define a first upstream V-strut arrangement that forms the upstream apexes 1316 of the first hexagonal cells 1312. The third struts 1333, therefore, define both the first upstream V-struts of the first hexagonal cells 1312 and the second downstream V-struts of the second hexagonal cells 1322.

The first longitudinal supports 1314 can include a plurality of holes 1336 through which sutures can pass to attach a prosthetic valve assembly and/or a sealing member. In the embodiment illustrated in FIG. 21, only the first longitudinal supports 1314 have holes 1336. However, in other embodiments the second longitudinal supports 1324 can also include holes either in addition to or in lieu of the holes 1336 in the first longitudinal supports 1314.

Figure 23:
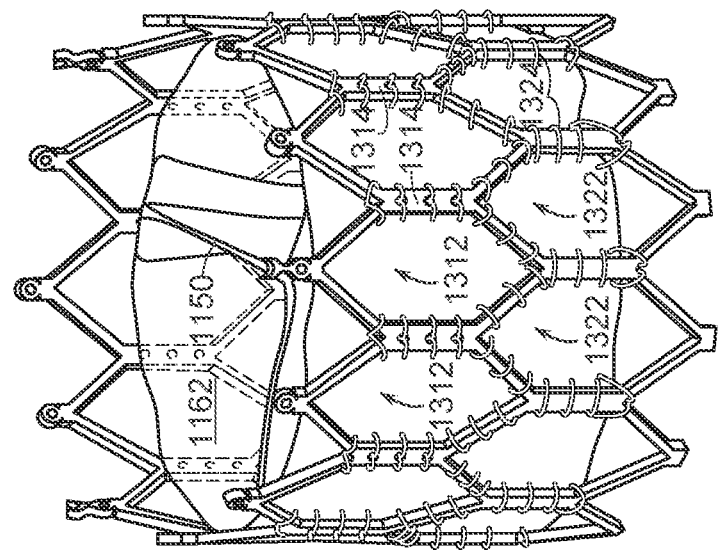
FIGS. 22 and 23 are side and bottom isometric views, respectively, of a prosthetic heart valve attached to the valve support of FIG. 21.
Figure 22:
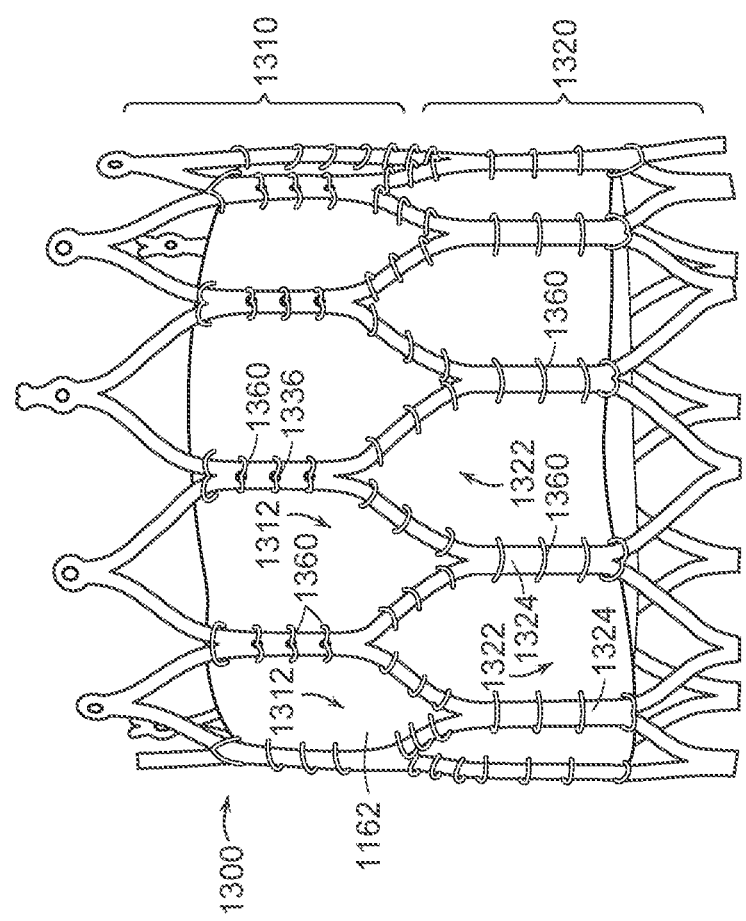

FIG. 22 is a side view and FIG. 23 is a bottom isometric view of the valve support 1300 with a first sealing member 1162 attached to the valve support 1300 and a prosthetic valve 1150 within the valve support 1300. The first sealing member 1162 can be attached to the valve support 1300 by a plurality of sutures 1360 coupled to the first longitudinal supports 1314 and the second longitudinal supports 1324. At least some of the sutures 1360 coupled to the first longitudinal supports 1314 pass through the holes 1336 to further secure the first sealing member 1162 to the valve support 1300.

Referring to FIG. 23, the prosthetic valve 1150 can be attached to the first sealing member 1162 and/or the first longitudinal supports 1314 of the valve support 1300. For example, the commissure portions of the prosthetic valve 1150 can be aligned with the first longitudinal supports 1314, and the sutures 1360 can pass through both the commissure portions of the prosthetic valve 1150 and the first sealing member 1162 where the commissure portions of the prosthetic valve 1150 are aligned with a first longitudinal support 1314. The inflow portion of the prosthetic valve 1150 can be sewn to the first sealing member 1162.

The valve support 1300 illustrated in FIGS. 21-23 is expected to be well suited for use with the device 1200 described above with reference to FIGS. 17-20. More specifically, the first struts 1331 cooperate with the extended connectors 1210 (FIGS. 17-20) of the device 1200 to separate the outflow portion of the prosthetic valve 1150 from the capsule 1700 (FIGS. 19-20) when the device 1200 is in a partially deployed state. The first struts 1331, for example, elongate when the valve support 1300 is not fully expanded (e.g., at least partially contained within the capsule 1700) and foreshorten when the valve support is fully expanded. This allows the outflow portion of the prosthetic valve 1150 to be spaced further apart from the capsule 1700 in a partially deployed state so that the prosthetic valve 1150 can at least partially function when the device 1200 (FIGS. 17-20) is in the partially deployed state. Therefore, the valve support 1300 is expected to enhance the ability to assess whether the prosthetic valve 1150 is fully operational in a partially deployed state.

Figure 24:
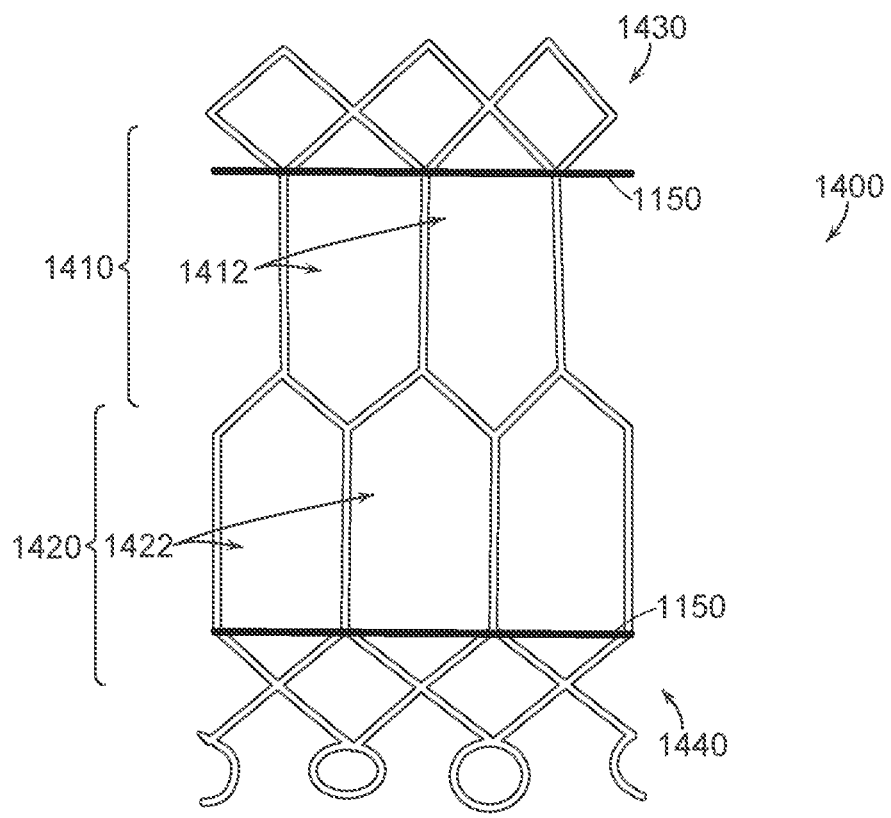
FIGS. 24 and 25 are side views schematically showing valve supports in accordance with additional embodiments of the present technology.
Figure 25:
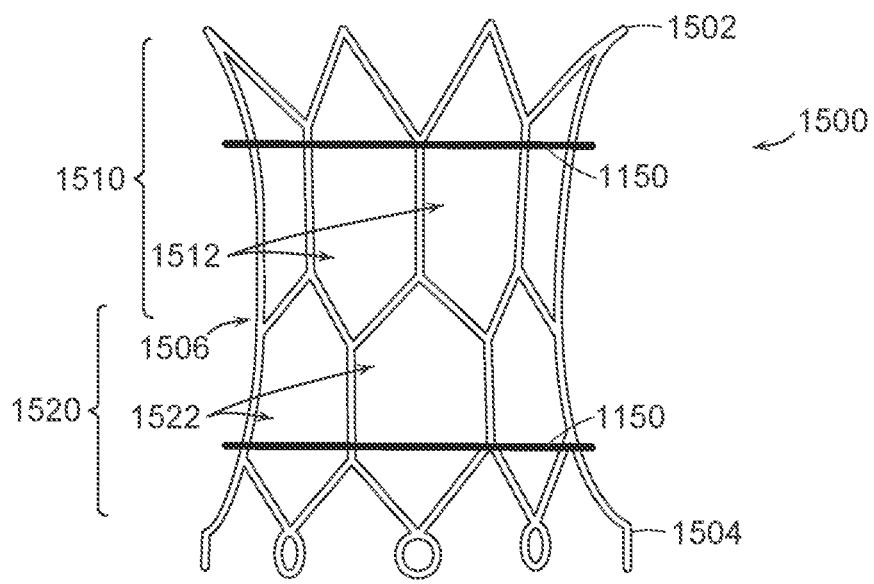

FIGS. 24 and 25 are schematic side views of valve supports 1400 and 1500, respectively, in accordance with other embodiments of the present technology. Referring to FIG. 24, the valve support 1400 includes a first row 1410 of first of hexagonal cells 1412 and a second row 1420 of second hexagonal cells 1422. The valve 1400 can further include a first row 1430 of diamond-shaped cells extending from the first hexagonal cells 1412 and a second row 1440 of diamond-shaped cells extending from the second hexagonal cells 1422. The additional diamond-shaped cells elongate in the low-profile state, and thus they can further space the prosthetic valve 1150 (shown schematically) apart from a capsule of a delivery device. Referring to FIG. 25, the valve support 1500 includes a first row 1510 of first hexagonal cells 1512 at an outflow region 1502 and a second row 1520 of second hexagonal cells 1522 at an inflow region 1504. The valve support 1500 is shaped such that an intermediate region 1506 (between the inflow and outflow regions 1502 and 1504) has a smaller cross-sectional area than that of the outflow region 1502 and/or the inflow region 1504. As such, the first row 1510 of first hexagonal cells 1512 flares outwardly in the downstream direction and the second row 1520 of second hexagonal cells 1522 flares outwardly in the upstream direction.

Examples

Several aspects of the present technology are set forth in the following examples.

1. A system for delivering a prosthetic heart valve device into a heart of a patient, the system comprising:
an elongated catheter body; and
a delivery capsule carried by the elongated catheter body and configured to be hydraulically driven between a containment configuration for holding the prosthetic heart valve device and a deployment configuration for at least partially deploying the prosthetic heart valve device,
wherein the delivery capsule includes a housing and a platform, and wherein—
the housing and the platform define, at least in part, a first chamber and a second chamber,
at least a portion of the delivery capsule is urged towards the deployment configuration when fluid is at least partially drained from the first chamber while fluid is delivered into the second chamber, and
at least a portion of the delivery capsule is urged towards the containment configuration to resheathe at least a portion of the prosthetic heart valve device when fluid is at least partially drained from the second chamber and delivered into the first chamber.

2. The system of example 1, further comprising a manifold at a proximal end region of the elongated catheter body and configured to receive the fluid for delivery to the first and/or second chambers, wherein the manifold comprises a first fluid lumen and first valve in fluid communication with the first chamber, and a second fluid lumen and a second valve in fluid communication with the second chamber.

3. The system of example 2 wherein the first and second valves are three-way valves.

4. The system of example 2 wherein the manifold is configured to be external to the patient during a implantation procedure.

5. The system of example 2 wherein the first fluid lumen is fluidly isolated from the second fluid lumen.

6. The system of any one of examples 1-5 wherein the delivery capsule is configured to axially restrain the prosthetic heart valve device while a first portion of the prosthetic heart valve device is deployed from the delivery capsule and to release an axially restrained portion of the prosthetic heart valve device while the first portion of the prosthetic heart valve device contacts tissue of a native valve of the heart of the patient.

7. The system of any one of examples 1-6 wherein the delivery capsule is configured to substantially prevent translation of the prosthetic heart valve device relative to the elongated catheter body while the prosthetic heart valve device moves between the containment configuration and the deployment configuration.

8. The system of any one of examples 1-7, further comprising a biasing device positioned along the catheter body and configured to urge the delivery capsule towards the containment configuration.

9. The system of example 8 wherein the biasing device comprises a spring positioned to be compressed as the delivery capsule moves towards the deployment configuration to deploy the prosthetic heart valve device when fluid is transferred to the first chamber.

10. The system of any one of examples 1-9, further comprising an engagement shaft extending through at least a portion of the elongated catheter body, wherein a distal end region of the engagement shaft is releasably coupled to the prosthetic heart valve device via one or more attachment elements, and wherein the one or attachment elements comprise pockets configured to mate with corresponding attachment features of the prosthetic heart valve device.

11. The system of example 10 wherein the attachment features comprise eyelet shaped projections configured to releasably engage corresponding pockets at the distal end region of the engagement shaft.

12. The system of example 10 wherein the attachment features comprise T-shaped projections configured to releasably mate with corresponding T-shaped pockets at the distal end region of the engagement shaft.

13. A system for delivering a prosthetic heart valve device for implantation at a native heart valve of a patient, the system comprising:
an elongated catheter body;
a delivery capsule coupled to the elongated catheter body and configured to contain the prosthetic heart valve device, wherein—
the delivery capsule is configured to be hydraulically driven between a containment configuration for holding the prosthetic heart valve device and a deployment configuration for deploying at least a portion of the prosthetic heart valve device,
the delivery capsule includes a housing and a platform that define, at least in part, a deployment chamber; and
an expandable member coupled to the elongated catheter body and distal to the delivery capsule, wherein the expandable member is configured to urge the delivery capsule towards the containment configuration and resheathe at least a portion of the prosthetic heart valve device when fluid is at least partially drained from the deployment chamber while fluid is delivered to the expandable member.

14. The system of example 13 wherein the delivery capsule is configured to substantially prevent translation of the prosthetic heart valve device relative to the elongated catheter body while the prosthetic heart valve device is at least partially resheathed.

15. The system of example 13 or 14 wherein the delivery capsule further comprises a containment chamber configured to contain the prosthetic heart valve device, and wherein the containment chamber is fluidically sealed from the deployment chamber via the platform1.

16. The system of any one of examples 13-15 wherein the expandable member is a balloon.

17. A method for delivering a prosthetic heart valve device to a native mitral valve of a heart of a human patient, the method comprising:
positioning a delivery capsule of an elongated catheter body within the heart, the delivery capsule carrying the prosthetic heart valve device;
delivering fluid to a first chamber within the delivery capsule to move the prosthetic heart valve device from a containment configuration within the delivery capsule to a deployment configuration, wherein the first chamber is proximal to the prosthetic heart valve device;
while fluid is delivered to the first chamber, draining fluid from a second chamber within the delivery capsule, wherein the second chamber is proximal to the prosthetic heart valve device; and
allowing the prosthetic heart valve device to radially expand to engage tissue of the native mitral valve when the delivery capsule moves from the containment configuration towards the deployment configuration.

18. The method of example 17, further comprising:
urging the delivery capsule toward the containment configuration to resheathe the prosthetic heart valve device after allowing the prosthetic heart valve device to at least partially radially expand, wherein urging the delivery capsule toward the containment configuration comprises—
draining fluid from the first chamber; and
while draining fluid from the first chamber, delivering fluid to the second chamber.

19. The method of example 17 or 18 wherein:
delivering fluid to the first chamber comprises delivering fluid from a manifold at a proximal portion of the elongated catheter body via a first fluid lumen; and
draining fluid from the second chamber comprises removing fluid via a second fluid lumen to the manifold.

20. The method of any one of examples 17-19 wherein delivering fluid to the first chamber and draining fluid from the second chamber at least substantially prevents translation of the prosethetic heart valve device relative to the elongated catheter body while the prosthetic heart valve device moves from the containment configuration to the deployment configuration.

21. The method of any one of examples 17-20, further comprising restraining a distal portion of the prosthetic heart valve device as the prosthetic heart valve device moves between the containment and deployment configurations, wherein the distal portion of the prosthetic heart valve device comprises attachment elements that releasably couple to pockets at a distal end region of an engagement shaft that extends through the elongated catheter body.

22. The method of example 21, further comprising moving the engagement shaft distally relative to the delivery capsule to release the restrained distal portion of the distal end region of the engagement shaft and fully expand the prosthetic heart valve device.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A system for delivering a prosthetic heart valve device into a heart of a patient, the system comprising:
an elongated catheter body;
a delivery capsule carried by the elongated catheter body and configured to be hydraulically driven between a containment configuration for holding the prosthetic heart valve device and a deployment configuration for at least partially deploying the prosthetic heart valve device;
a first chamber at least partially defined by a first surface of a platform and a housing of the capsule;
a second chamber at least partially defined by the housing of the capsule and a second surface of the platform opposite the first surface, the first chamber and the second chamber configured to receive and drain fluid; and
a manifold at a proximal end region of the elongated catheter body and configured to receive fluid for delivery to at least one of the first or second chambers, wherein the manifold comprises a first fluid lumen and first valve in fluid communication with the first chamber, and a second fluid lumen and a second valve in fluid communication with the second chamber, wherein in the containment configuration the first chamber is at least partially filled with fluid and the second chamber is at least partially drained of fluid, and wherein in the deployment configuration the second chamber is at least partially filled with fluid and the first chamber is at least partially drained of fluid.

2. The system of claim 1 wherein the first and second valves are three-way valves.

3. The system of claim 1 wherein the manifold is configured to be external to the patient during an implantation procedure.

4. The system of claim 1 wherein the first fluid lumen is fluidly isolated from the second fluid lumen.

5. The system of claim 1 wherein the delivery capsule is configured to axially restrain the prosthetic heart valve device while a first portion of the prosthetic heart valve device is deployed from the delivery capsule and to release an axially restrained portion of the prosthetic heart valve device while the first portion of the prosthetic heart valve device contacts tissue of a native valve of the heart of the patient.

6. The system of claim 1, further comprising a biasing device positioned along the elongated catheter body and configured to urge the delivery capsule towards the containment configuration.

7. The system of claim 6 wherein the biasing device comprises a spring positioned to be compressed as the delivery capsule moves towards the deployment configuration to deploy the prosthetic heart valve device when fluid is transferred to the first chamber.

8. The system of claim 1 wherein the delivery capsule is configured to move distally towards the deployment configuration.

9. The system of claim 1 wherein the delivery capsule is configured to move proximally towards the deployment configuration.

10. The system of claim 1, further comprising:
an engagement device coupled to a portion of the prosthetic heart valve device, wherein in the deployment configuration the portion of the prosthetic heart valve device is disposed within the capsule such that the prosthetic heart valve device is partially deployed, wherein in a fully deployed configuration, the engagement device is advanced such that the portion of the prosthetic heart valve device is not disposed within the capsule.

11. The system of claim 10, wherein the engagement device includes shaped recesses configured to receive shaped attachment features of the prosthetic heart valve device.

12. A method for delivering a prosthetic heart valve device to a native valve of a heart of a human patient, the method comprising:
positioning a delivery capsule of an elongated catheter body within the heart, the delivery capsule carrying the prosthetic heart valve device; and
delivering fluid from a first fluid lumen of a manifold to a first chamber at least partially defined by a first surface of a platform and a housing of the capsule and simultaneously draining fluid from a second chamber at least partially defined by the housing of the capsule and a second surface of the platform opposite the first surface into a second fluid lumen of the manifold to move the delivery capsule from a containment configuration with the prosthetic heart valve device disposed within the delivery capsule towards a deployment configuration with the prosthetic heart valve device at least partially released from the delivery capsule.

13. The method of claim 12, further comprising: delivering fluid from the second fluid lumen of the manifold to the second chamber and draining fluid from the first chamber into the first fluid lumen of the manifold to move the delivery capsule from the deployment configuration towards the containment configuration to resheathe at least a portion of the prosthetic heart valve device within the delivery capsule.

14. The method of claim 12 wherein moving the delivery capsule towards the deployment configuration comprises moving the delivery capsule distally.

15. The method of claim 12 wherein moving the delivery capsule towards the deployment configuration comprises moving the delivery capsule proximally.

16. The method of claim 12, further comprising:
with the capsule in the deployment configuration and the prosthetic heart valve device partially expanded, advancing an engagement device coupled to the prosthetic heart valve device to fully deploy the prosthetic heart valve device.

17. The method of claim 16, wherein with the capsule in the deployment configuration, the engagement device and a portion of the prosthetic heart valve device coupled to the engagement device are disposed within the capsule, and wherein advancing the engagement device releases the portion of the prosthetic heart valve device from the capsule to fully deploy the prosthetic heart valve device.

18. The method of claim 16, wherein the engagement device is coupled to a shaft, wherein advancing the engagement device comprises advancing the shaft.

* * * * *